US012637443B2

(12) United States Patent
Nakahara

(10) Patent No.: US 12,637,443 B2
(45) Date of Patent: May 26, 2026

(54) CYCLIC AMINE DERIVATIVES HAVING SEROTONIN RECEPTOR BINDING ACTIVITY

(71) Applicant: Shionogi & Co., Ltd., Osaka (JP)

(72) Inventor: Kenji Nakahara, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 408 days.

(21) Appl. No.: 18/269,692

(22) PCT Filed: Dec. 27, 2021

(86) PCT No.: PCT/JP2021/048476
§ 371 (c)(1),
(2) Date: Jun. 26, 2023

(87) PCT Pub. No.: WO2022/145408
PCT Pub. Date: Jul. 7, 2022

(65) Prior Publication Data
US 2024/0083872 A1 Mar. 14, 2024

(30) Foreign Application Priority Data
Dec. 28, 2020 (JP) ................................ 2020-218179

(51) Int. Cl.
*C07D 401/12* (2006.01)
*C07D 403/12* (2006.01)
(Continued)

(52) U.S. Cl.
CPC ......... *C07D 401/12* (2013.01); *C07D 403/12* (2013.01); *C07D 405/12* (2013.01);
(Continued)

(58) Field of Classification Search
CPC .. C07D 401/12; C07D 403/12; C07D 405/12; C07D 405/14; C07D 409/12;
(Continued)

(56) References Cited

U.S. PATENT DOCUMENTS 8,377,959 B2 2/2013 Weiner et al.
11,576,897 B2 2/2023 Kato et al.
(Continued)

FOREIGN PATENT DOCUMENTS

CN 109111385 1/2019
CN 113214141 8/2021
(Continued)

OTHER PUBLICATIONS

CN113549006A ('006, English translation) Oct. 26, 2021.*
(Continued)

*Primary Examiner* — Robert H Havlin
(74) *Attorney, Agent, or Firm* — Wenderoth, Lind & Ponack, L.L.P.

(57) ABSTRACT

Provided are a compound having serotonin 5-HT2A receptor antagonism and/or inverse agonism, a pharmaceutically acceptable salt thereof, and a composition for serotonin 5-HT2A receptor antagonism and/or inverse agonism comprising them.
A compound represented by Formula (I):

(I)

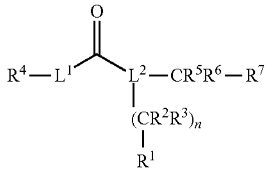

wherein $R^1$ is substituted or unsubstituted aromatic heterocyclyl or the like; $R^2$ is each independently a hydrogen atom or the like; $R^3$ is each independently a hydrogen atom or the like; n is 1 or the like; a combination of ($L^1$, $L^2$) is (NH, N) or the like; $R^4$ is a group represented by Formula:

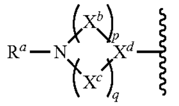

wherein p and q are each independently 2 or the like; $R^a$ is substituted or unsubstituted alkyl or the like; $X^b$ is each independently $CR^bR^{b'}$; $R^b$ is each independently a hydrogen atom or the like; $R^{b'}$ is each independently a hydrogen atom or the like; $X^c$ is each independently $CR^cR^{c'}$; $R^c$ is each independently a hydrogen atom or the like; $R^{c'}$ is each independently a hydrogen atom or the like; $X^d$ is $CR^d$ or the like; and $R^d$ is a hydrogen atom or the like; $R^5$ and $R^6$ are each independently a hydrogen atom or the like; and $R^7$ is a group represented by Formula:

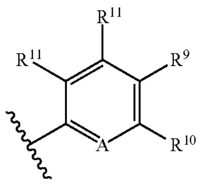

wherein A is $CR^{11}$ or the like; $R^9$ is substituted or unsubstituted alkyloxy or the like; $R^{10}$ is a hydrogen atom or the like; and $R^{11}$ is each independently a hydrogen atom or the like; or a pharmaceutically acceptable salt thereof.

18 Claims, 2 Drawing Sheets

(51) Int. Cl.

| | |
|---|---|
| ***C07D 405/12*** | (2006.01) |
| ***C07D 405/14*** | (2006.01) |
| ***C07D 409/12*** | (2006.01) |
| ***C07D 413/12*** | (2006.01) |
| ***C07D 417/12*** | (2006.01) |
| ***C07D 471/08*** | (2006.01) |

(52) U.S. Cl.
CPC ......... *C07D 405/14* (2013.01); *C07D 409/12* (2013.01); *C07D 413/12* (2013.01); *C07D 417/12* (2013.01); *C07D 471/08* (2013.01)

(58) Field of Classification Search
CPC .. C07D 413/12; C07D 417/12; C07D 471/08; C07D 261/08; C07D 471/04; A61K 31/4155; A61K 31/4535; A61K 31/454; A61K 31/4545; A61K 31/497; A61K 31/506; A61K 31/55; A61P 25/14; A61P 25/16; A61P 25/28; A61P 43/00
See application file for complete search history.

(56) References Cited

U.S. PATENT DOCUMENTS

| | | | | |
|---|---|---|---|---|
| 2023/0143664 | A1 | 5/2023 | Nakahara et al. | |
| 2023/0348421 | A1* | 11/2023 | Zhang .................. | C07D 413/12 |

FOREIGN PATENT DOCUMENTS

| | | |
|---|---|---|
| CN | 113214231 | 8/2021 |
| CN | 113214289 | 8/2021 |
| CN | 113549006 | 10/2021 |
| EP | 3 569 233 | 11/2019 |
| EP | 4144725 | 3/2023 |
| WO | 01/66521 | 9/2001 |
| WO | 2003/057698 | 7/2003 |
| WO | 2004/000808 | 12/2003 |
| WO | 2004/000840 | 12/2003 |
| WO | 2004/064738 | 8/2004 |
| WO | 2007/124136 | 11/2007 |
| WO | 2009/039461 | 3/2009 |
| WO | 2010/111353 | 9/2010 |
| WO | 2018/131672 | 7/2018 |
| WO | 2019/040104 | 2/2019 |
| WO | 2019/040105 | 2/2019 |
| WO | 2019/040106 | 2/2019 |
| WO | 2019/040107 | 2/2019 |
| WO | 2021/147818 | 7/2021 |
| WO | 2021/147909 | 7/2021 |
| WO | 2021/193790 | 9/2021 |
| WO | 2021/218863 | 11/2021 |
| WO | 2022/017440 | 1/2022 |

OTHER PUBLICATIONS

International Search Report issued Feb. 22, 2022 in International (PCT) Application No. PCT/JP2021/048476.

Pievani, M., et al, "Brain connectivity in neurodegenerative diseases-from phenotype to proteinopathy", Nature Reviews Neurology, Nov. 2014, vol. 10, pp. 620-633.

Mishriky, R. S. L., et al., "Pharmacological alternatives to antipsychotics to manage BPSD", Progress in Neurology and Psychiatry, 2018, vol. 22, Issue 1, pp. 30-35.

Barone, P., et al., "The Priamo Study: A Multicenter Assessment of Nonmotor Symptoms and Their Impact on Quality of Life in Parkinson's Disease", Movement Disorders, 2009, vol. 24, No. 11, pp. 1641-1649.

Postuma, R.B., et al., "Predicting Parkinson's disease—why, when, and how?", Parkinsonism and Related Disorders 15S3, 2009, pp. S105-S109.

Marsh, L., et al., "Psychiatric comorbidities in patients with Parkinson disease and psychosis", Neurology, 2004; vol. 63, No. 2, pp. 293-300.

Weintraub, D., et al., "Association of Antipsychotic Use With Mortality Risk in Patients With Parkinson Disease", JAMA Neurol., May 1, 2016, vol. 73, No. 5, pp. 535-541.

Cummings, J., et al., "Pimavanserin for patients with Parkinson's disease psychosis: a randomised, placebo-controlled phase 3 trial", The Lancet, 2014, vol. 383, pp. 533-540.

Vanover, K.E., et al., "Pharmacological and Behavioral Profile of N-(4-Fluorophenylmethyl)-N-(1-methylpiperidin-4-yl)-N'-(4-(2-methylpropyloxy)phenylmethyl) Carbamide (2R,3R)-Dihydroxybutanedioate(2:1)(ACP-103), a Novel 5-Hydroxytryptamine$_{2A}$ Receptor Inverse Agonist", Journal of Pharmacology and Experimental Therapeutics, May 2006, vol. 317, No. 2, pp. 910-918.

Stahl, S.M., "Mechanism of action of pimavanserin in Parkinson's disease psychosis: targeting serotonin 5HT2A and 5HT2C receptors", CNS Spectrums, 2016, vol. 21, pp. 271-275.

English translation of International Preliminary Report on Patentability mailed Jul. 13, 2023 in corresponding International (PCT) Application No. PCT/JP2021/048476.

* cited by examiner

One-way ANOVA;
* p<0.05
** p<0.01
*** P<0.001

One-way ANOVA;
* p<0.05
** p<0.01
*** P<0.001

CYCLIC AMINE DERIVATIVES HAVING SEROTONIN RECEPTOR BINDING ACTIVITY

TECHNICAL FIELD

The present invention relates to a compound having serotonin 5-HT2A receptor antagonism and/or inverse agonism and useful in the treatment and/or prevention of a disease caused by a serotonin 5-HT2A receptor or a pharmaceutically acceptable salt thereof, and a pharmaceutical composition comprising them.

BACKGROUND ART

Neurodegenerative disorder (ND) is a group ωf related human diseases that exhibit a common pathophysiological feature, namely progressive degeneration of selective neuronal populations that occurs over time. These neurodegenerative diseases include, but are not limited to, for example, Alzheimer's disease and related dementia, Parkinson's disease, Huntington's disease, Lewy bodies disease, and related movement disorders. Each of these disorders has its own unique clinical aspects, such as age of onset, time course of progression, neurologic signs and symptoms, neuropsychiatric symptoms, and susceptibility to known therapeutic agents. In addition, the pathophysiological basis of each of these disorders is caused by a genetic mechanism peculiar to each disease (Non-patent Document 1).

Despite the considerable progress in elucidating the genetic causes underlying these essentially different disorders, comparatively little is known about the biochemical mechanisms that cause selective neuronal degeneration that are common to all of them. In addition, for the most common disorders of these ones, including Parkinson's disease and Alzheimer's disease, genetic factors that cause these rare familial diseases have been discovered, but for the majority of sporadic cases, the pathophysiological basis is not known yet. Therefore, there is currently no specific therapeutic agent capable of directly altering the progression of the disease. Instead, clinicians utilize a variety of existing agents to achieve symptom relief of the motional manifestations, cognitive manifestations, and neuropsychiatric manifestations that characterize these disorders (Non-patent Documents 2 and 3).

Of the various neurological symptoms that characterize ND, the appearances of neuropsychiatric symptoms, including slow motion, abnormal motor function, including dyskinesia and chorea, and emotional symptoms such as psychosis and anxiety and depression, are common symptoms, seriously affects the functional status and quality of life of patients (Non-patent Documents 4 and 5). Most existing therapeutic agents, including antipsychotics and antidepressants, are often effective in these patients, but their tolerability is significantly poor (Non-patent Document 6). Also, available Parkinson's disease therapeutic agents, including L-dopa and dopamine agonists, are generally effective, but cause the emergence of treatment-restricting side effects that are currently too severe to be addressed by drug therapy.

Although there has been no ND-specific approved drug for a long time, the 5-HT2A receptor inverse agonist pimavanserin was first approved in the United States in 2016 for the indication of Parkinson's disease-related hallucinations and delusions (Non-patent Document 7). Unlike existing antipsychotic drugs, this drug has not been reported to have side effects of worsening motor symptoms or cognitive decline. The main pharmacological action of pimavanserin is serotonin 5-HT2A receptor inverse agonism/antagonism, but it also has serotonin 5-HT2C receptor inverse agonism (Non-patent Document 8). The results of 5-HT2A occupancy measured in the PET test of pimavanserin in humans and the results of clinical trials of pimavanserin suggest that pimavanserin exerts its medicinal effect via 5-HT2A and 5-HT2C (Non-patent Document 9). In addition, pimavanserin has a large adverse effect on the cardiovascular system, and its use is restricted.

These findings require the development of novel therapeutic agents specifically designed to be not only effective for these specific symptoms which cause physical disability, but also tolerated in these specific patient populations. This can be achieved by improving the selectivity of drug-target interactions of new therapeutic agents. Specifically, it can be achieved by having strong activity and selectivity for target 5-HT2A, preferably 5-HT2A and 5-HT2C, and reducing adverse effects on the cardiovascular system.

Patent Documents 3 to 14 and 16 to 22 describe compounds having serotonin 5-HT2A receptor antagonism and/or inverse agonism, but any of the documents does not describe or suggest the compounds related to the present invention.

Quinuclidine derivatives having muscarinic $M_3$ receptor inhibitory activity are disclosed in Patent Document 15, but serotonin 5-HT2A receptor antagonism and/or inverse agonism and therapeutic effects on hallucinations and delusions are not described, and the compounds related to the present invention are not described or suggested.

PRIOR ART REFERENCES

Patent Documents

[Patent Document 1] International Publication WO2018/131672

[Patent Document 2] Publication U.S. Pat. No. 8,377,959

[Patent Document 3] International Publication WO2001/066521

[Patent Document 4] International Publication WO2004/064738

[Patent Document 5] International Publication WO2019/040104

[Patent Document 6] International Publication WO2019/040105

[Patent Document 7] International Publication WO2019/040106

[Patent Document 8] International Publication WO2019/040107

[Patent Document 9] International Publication WO2010/111353

[Patent Document 10] International Publication WO2004/000808

[Patent Document 11] International Publication WO2003/057698

[Patent Document 12] China Patent Application Publication CN109111385

[Patent Document 13] International Publication WO2009/039461

[Patent Document 14] International Publication WO2007/124136

[Patent Document 15] International Publication WO2004/000840

[Patent Document 16] International Publication WO2021/147818

[Patent Document 17] International Publication WO2021/147909

[Patent Document 18] China Patent Application Publication CN109111385

[Patent Document 19] China Patent Application Publication CN113214141

[Patent Document 20] China Patent Application Publication CN113214231

[Patent Document 21] China Patent Application Publication CN113214289

[Patent Document 22] International Publication WO2021/218863

Non-Patent Documents

[Non-patent Document 1] Nature Reviews Neurology volume 10, pages 620-633 (2014)

[Non-patent Document 2] Progress in Neurology and Psychiatry I Vol. 22 Iss. 1, 30-35, 2018

[Non-patent Document 3] Movement Disorders Vol. 24, No. 11, 2009, pp. 1641-1649

[Non-patent Document 4] Parkinsonism and Related Disorders, 1553, 2009, S105-S109.

[Non-patent Document 5] Neurology. 2004; 63 (2): 293-300.

[Non-patent Document 6] JAMA Neurol. 2016; 73 (5): 535-541.

[Non-patent Document 7] Lancet; 383: 533-540 (2014)

[Non-patent Document 8] Journal of Pharmacology and Experimental Therapeutics May 2006, 317 (2) 910-918

[Non-patent Document 9] CNS Spectrums (2016), 21, 271-275

SUMMARY OF THE INVENTION

Problems to be Solved by the Invention

An object of the present invention is to provide a novel compound having serotonin 5-HT2A receptor antagonism and/or inverse agonism. Preferably the present invention is to provide a novel compound having an effect on serotonin-related disease such as Parkinson's disease- and/or dementia-related hallucinations and delusions by having serotonin 5-HT2A receptor antagonism and/or inverse agonism, and a pharmaceutical comprising the same.

Means for Solving the Problem

The present invention relates to the following items (1) to (31), (1') to (20'), and (26') to (31').

(1) A compound represented by Formula (I):

[Chemical formula 1]

(I)

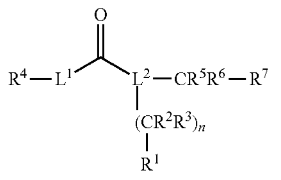

wherein $R^1$ is substituted or unsubstituted aromatic heterocyclyl or substituted or unsubstituted non-aromatic heterocyclyl;

$R^2$ is each independently a hydrogen atom, halogen, hydroxy, substituted or unsubstituted alkyl, or substituted or unsubstituted alkyloxy;

$R^3$ is each independently a hydrogen atom, halogen, hydroxy, substituted or unsubstituted alkyl, or substituted or unsubstituted alkyloxy;

n is 0, 1, or 2;

a combination of ($L^1$, $L^2$) is ($NR^{L1}$, N), ($CR^{L1}R^{L1'}$, N), (O, N), (O, $CR^{L2}$), or ($NR^{L1}$, $CR^{L2}$);

$R^{L1}$, $R^{L1'}$, and $R^{L2}$ are each independently a hydrogen atom or substituted or unsubstituted alkyl;

$R^4$ is a group represented by Formula:

[Chemical formula 2]

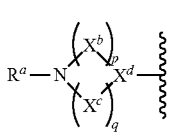

or

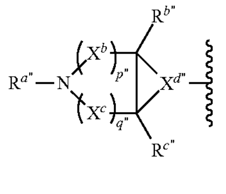

wherein p and q are each independently 1, 2, or 3;

p" and q" are each independently 1 or 2;

$R^a$ is a hydrogen atom, substituted or unsubstituted alkyl, substituted or unsubstituted alkenyl, or substituted or unsubstituted alkynyl;

$R^{a''}$ is a hydrogen atom, substituted or unsubstituted alkyl, substituted or unsubstituted alkenyl, or substituted or unsubstituted alkynyl;

$X^b$ is each independently $CR^bR^{b'}$;

$X^c$ is each independently $CR^cR^{c'}$.

$R^b$ is each independently a hydrogen atom, halogen, substituted or unsubstituted alkyl, or substituted or unsubstituted alkyloxy;

$R^{b'}$ is each independently a hydrogen atom, halogen, substituted or unsubstituted alkyl, or substituted or unsubstituted alkyloxy;

$R^c$ is each independently a hydrogen atom, halogen, substituted or unsubstituted alkyl, or substituted or unsubstituted alkyloxy;

$R^{c'}$ is each independently a hydrogen atom, halogen, substituted or unsubstituted alkyl, or substituted or unsubstituted alkyloxy;

$R^{b''}$ is a hydrogen atom, halogen, substituted or unsubstituted alkyl, or substituted or unsubstituted alkyloxy;

$R^{c''}$ is a hydrogen atom, halogen, substituted or unsubstituted alkyl, or substituted or unsubstituted alkyloxy;

$X^d$ is $CR^d$ or N;

$X^{d''}$ is $CR^d$ or N;

$R^d$ is a hydrogen atom, halogen, cyano, substituted or unsubstituted alkyl, or substituted or unsubstituted carbamoyl;

$R^b$ and $R^{b'}$ and $R^c$ and $R^{c'}$ may be taken together with the same carbon atom to which they are bonded to form a substituted or unsubstituted non-aromatic carbocycle or a substituted or unsubstituted non-aromatic heterocycle;

$R^a$, and $R^b$ bonded to a carbon atom adjacent to a nitrogen atom to which $R^a$ is bonded, and $R^a$, and $R^c$ bonded to a carbon atom adjacent to a nitrogen atom to which $R^a$ is bonded may be taken together with the nitrogen atom to which $R^a$ is bonded and the carbon atom to which $R^b$ or $R^c$ is bonded to form a substituted or unsubstituted non-aromatic heterocycle;

$R^b$ and $R^c$ may be taken together to form a (C1-C3) bridge, wherein one of the carbon atoms constituting the bridge may be replaced with an oxygen atom;

$R^a$ and $R^d$ may be taken together to form a (C1-C3) bridge, wherein one of the carbon atoms constituting the bridge may be replaced with an oxygen atom;

$R^5$ and $R^6$ are each independently a hydrogen atom, halogen, hydroxy, substituted or unsubstituted alkyl, or substituted or unsubstituted alkyloxy; or $R^5$ and $R^6$ may be taken together with the same carbon atom to which they are bonded to form a substituted or unsubstituted non-aromatic carbocycle;

$R^7$ is a group represented by Formula:

[Chemical formula 3]

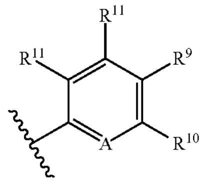

wherein A is $CR^{11}$ or N;

$R^9$ is substituted or unsubstituted alkyloxy, substituted or unsubstituted amino, substituted or unsubstituted aromatic carbocyclyloxy, substituted or unsubstituted alkyl, substituted or unsubstituted non-aromatic carbocyclyl, or cyano;

$R^{10}$ is a hydrogen atom, halogen, hydroxy, substituted or unsubstituted alkyl, or substituted or unsubstituted alkyloxy; or $R^9$ and $R^{10}$ may be taken together to form a substituted or unsubstituted non-aromatic carbocycle or a substituted or unsubstituted non-aromatic heterocycle;

$R^{11}$ is each independently a hydrogen atom, halogen, hydroxy, substituted or unsubstituted alkyl, or substituted or unsubstituted alkyloxy;

provided that (i) when a combination of ($L^1$, $L^2$) is any of ($CR^{L1}R^{L1'}$, N), (O, N), (O, $CR^{L2}$), or ($NR^{L1}$, $CR^{L2}$), n is 1 or 2;

(ii) when a combination of ($L^1$, $L^2$) is ($NR^{L1}$, N) and $R^4$ is a group represented by Formula:

[Chemical formula 4]

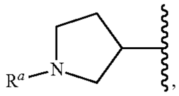, $R^a$ is not alkyl substituted with aromatic carbocyclyl or alkyl substituted with non-aromatic heterocyclyl;

provided that the following compounds are excluded:

[Chemical formula 5]

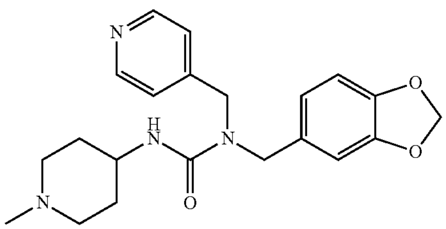,

-continued

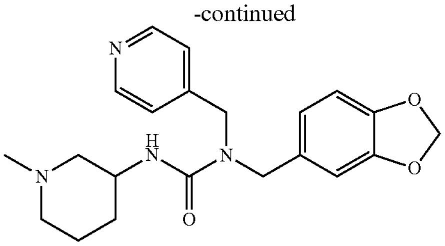,

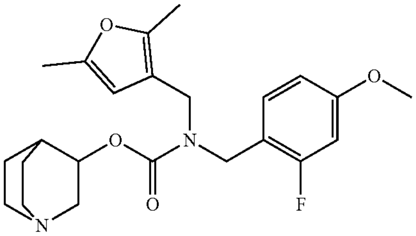,

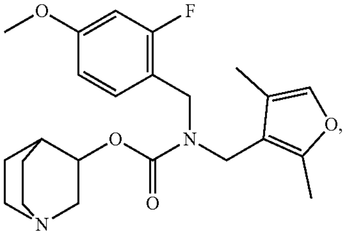

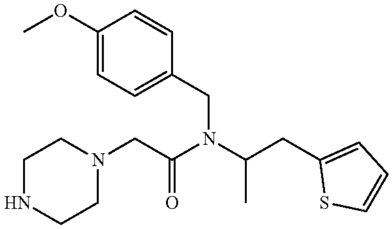,

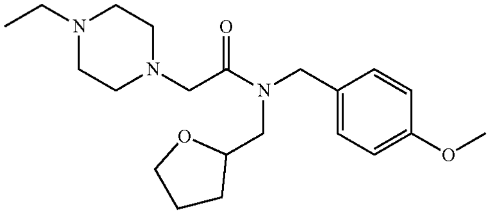

and

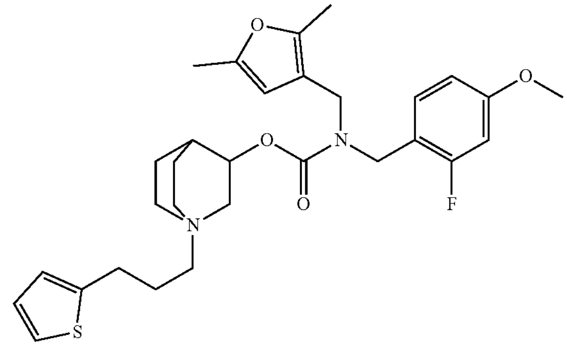

or a pharmaceutically acceptable salt thereof.

(2) The compound according to the above item (1), wherein A is $CR^{11}$, or a pharmaceutically acceptable salt thereof.

(3) The compound according to the above item (1) or (2), wherein A is CH, or a pharmaceutically acceptable salt thereof.

(4) The compound according to any one of the above items (1) to (3), wherein n is 1 or 2, or a pharmaceutically acceptable salt thereof.

(5) The compound according to any one of the above items (1) to (4), wherein the combination of ($L^1$, $L^2$) is ($NR^{L1}$, N) or ($CR^{L1}R^{L1'}$, N), or a pharmaceutically acceptable salt thereof.

(6) The compound according to any one of the above items (1) to (5), wherein the combination of ($L^1$, $L^2$) is (NH, N) or ($CH_2$, N), or a pharmaceutically acceptable salt thereof.

(7) The compound according to any one of the above items (1) to (6), wherein $X^d$ is $CR^d$, and $R^d$ is a hydrogen atom or substituted or unsubstituted alkyl, or a pharmaceutically acceptable salt thereof.

(8) The compound according to any one of the above items (1) to (7), wherein $X^d$ is CH, or a pharmaceutically acceptable salt thereof.

(9) The compound according to any one of the above items (1) to (8), wherein p is 2, and q is 2, or a pharmaceutically acceptable salt thereof.

(10) The compound according to any one of the above items (1) to (9), wherein $R^2$ is each independently a hydrogen atom or substituted or unsubstituted alkyl, and $R^3$ is each independently a hydrogen atom or substituted or unsubstituted alkyl, or a pharmaceutically acceptable salt thereof.

(11) The compound according to any one of the above items (1) to (10), wherein $R^5$ and $R^6$ are each independently a hydrogen atom or substituted or unsubstituted alkyl, or a pharmaceutically acceptable salt thereof.

(12) The compound according to any one of the above items (1) to (11), wherein $R^1$ is substituted or unsubstituted 5-membered aromatic heterocyclyl, substituted or unsubstituted pyridin-2-yl, substituted or unsubstituted pyridin-3-yl, substituted or unsubstituted pyridazin-3-yl, substituted or unsubstituted pyrimidin-2-yl, substituted or unsubstituted pyrimidin-5-yl, substituted or unsubstituted pyrazinyl, substituted or unsubstituted 9-membered aromatic heterocyclyl, substituted or unsubstituted 10-membered aromatic heterocyclyl, or substituted or unsubstituted non-aromatic heterocyclyl, or a pharmaceutically acceptable salt thereof.

(13) The compound according to any one of the above items (1) to (12), wherein $R^1$ is substituted or unsubstituted 5-membered aromatic heterocyclyl, or a pharmaceutically acceptable salt thereof.

(14) A pharmaceutical composition comprising the compound according to any one of the above items (1) to (13) or a pharmaceutically acceptable salt thereof.

(15) The pharmaceutical composition according to the above item (14), wherein the pharmaceutical composition is a serotonin 5-HT2A receptor inverse agonist.

(16) The pharmaceutical composition according to the above item (14), wherein the pharmaceutical composition is a serotonin 5-HT2A and 5-HT2C receptor inverse agonist.

(17) A serotonin 5-HT2A receptor inverse agonist comprising a compound represented by Formula (I):

[Chemical formula 6]

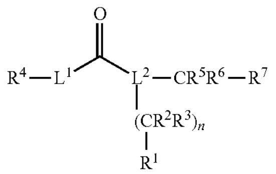

(I)

wherein $R^1$ is substituted or unsubstituted aromatic heterocyclyl or substituted or unsubstituted non-aromatic heterocyclyl;

$R^2$ is each independently a hydrogen atom, halogen, hydroxy, substituted or unsubstituted alkyl, or substituted or unsubstituted alkyloxy;

$R^3$ is each independently a hydrogen atom, halogen, hydroxy, substituted or unsubstituted alkyl, or substituted or unsubstituted alkyloxy;

n is 0, 1, or 2;

a combination of ($L^1$, $L^2$) is ($NR^{L1}$, N), ($CR^{L1}R^{L1'}$, N), (O, N), (O, $CR^{L2}$), or ($NR^{L1}$, $CR^{L2}$);

$R^{L1}$, $R^{L1'}$, and $R^{L2}$ are each independently a hydrogen atom or substituted or unsubstituted alkyl;

$R^4$ is substituted or unsubstituted non-aromatic nitrogen-containing heterocyclyl;

$R^5$ and $R^6$ are each independently a hydrogen atom, halogen, hydroxy, substituted or unsubstituted alkyl, or substituted or unsubstituted alkyloxy; or $R^5$ and $R^6$ may be taken together with the same carbon atom to which they are bonded to form a substituted or unsubstituted non-aromatic carbocycle;

$R^7$ is a group represented by Formula:

[Chemical formula 7]

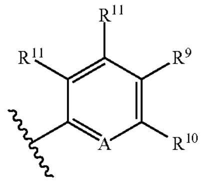

wherein A is $CR^{11}$ or N;

$R^9$ is substituted or unsubstituted alkyloxy, substituted or unsubstituted amino, substituted or unsubstituted aromatic carbocyclyloxy, substituted or unsubstituted alkyl, substituted or unsubstituted non-aromatic carbocyclyl, or cyano;

$R^{10}$ is a hydrogen atom, halogen, hydroxy, substituted or unsubstituted alkyl, or substituted or unsubstituted alkyloxy; or $R^9$ and $R^{10}$ may be taken together to form a substituted or unsubstituted non-aromatic carbocycle or a substituted or unsubstituted non-aromatic heterocycle;

$R^{11}$ is each independently a hydrogen atom, halogen, hydroxy, substituted or unsubstituted alkyl, or substituted or unsubstituted alkyloxy;

or a pharmaceutically acceptable salt thereof.

(18) The serotonin 5-HT2A receptor inverse agonist according to the above item (17), wherein $R^4$ is a group represented by Formula:

[Chemical formula 8]

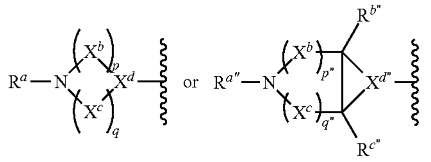

or wherein each symbol has the same meaning as the above item (1).

(19) The serotonin 5-HT2A receptor inverse agonist according to the above item (17) or (18), wherein the serotonin 5-HT2A receptor inverse agonist is a serotonin 5-HT2A and 5-HT2C receptor inverse agonist.

(1') A compound represented by Formula (I):

[Chemical formula 9]

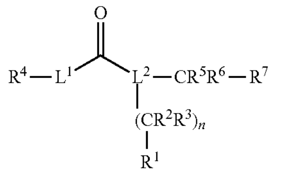

(I)

wherein $R^1$ is substituted or unsubstituted aromatic heterocyclyl or substituted or unsubstituted non-aromatic heterocyclyl;

$R^2$ is each independently a hydrogen atom, halogen, hydroxy, substituted or unsubstituted alkyl, or substituted or unsubstituted alkyloxy;

$R^3$ is each independently a hydrogen atom, halogen, hydroxy, substituted or unsubstituted alkyl, or substituted or unsubstituted alkyloxy;

n is 0, 1, or 2;

a combination of ($L^1$, $L^2$) is ($NR^{L1}$, N), ($CR^{L1}R^{L1'}$, N), (O, N), (O, $CR^{L2}$), or ($NR^{L1}$, $CR^{L2}$);

$R^{L1}$, $R^{L1'}$, and $R^{L2}$ are each independently a hydrogen atom, halogen, or substituted or unsubstituted alkyl;

$R^4$ is a group represented by Formula:

[Chemical formula 10]

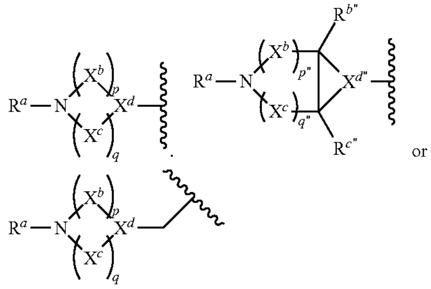

, or wherein p and q are each independently 1, 2, or 3;

p" and q" are each independently 1 or 2;

$R^a$ is a hydrogen atom, substituted or unsubstituted alkyl, substituted or unsubstituted alkenyl, substituted or unsubstituted alkynyl, substituted or unsubstituted non-aromatic carbocyclyl, or substituted or unsubstituted non-aromatic heterocyclyl;

$R^{a''}$ is a hydrogen atom, substituted or unsubstituted alkyl, substituted or unsubstituted alkenyl, substituted or unsubstituted alkynyl, substituted or unsubstituted non-aromatic carbocyclyl, or substituted or unsubstituted non-aromatic heterocyclyl;

$X^b$ is each independently $CR^bR^{b'}$;

$X^c$ is each independently $CR^cR^{c'}$.

$R^b$ is each independently a hydrogen atom, halogen, substituted or unsubstituted alkyl, or substituted or unsubstituted alkyloxy;

$R^{b'}$ is each independently a hydrogen atom, halogen, substituted or unsubstituted alkyl, or substituted or unsubstituted alkyloxy;

$R^c$ is each independently a hydrogen atom, halogen, substituted or unsubstituted alkyl, or substituted or unsubstituted alkyloxy;

$R^{c'}$ is each independently a hydrogen atom, halogen, substituted or unsubstituted alkyl, or substituted or unsubstituted alkyloxy;

$R^{b''}$ is a hydrogen atom, halogen, substituted or unsubstituted alkyl, or substituted or unsubstituted alkyloxy;

$R^{c''}$ is a hydrogen atom, halogen, substituted or unsubstituted alkyl, or substituted or unsubstituted alkyloxy;

$X^d$ is $CR^d$ or N;

$X^{d''}$ is $CR^d$ or N;

$R^d$ is a hydrogen atom, halogen, cyano, substituted or unsubstituted alkyl, or substituted or unsubstituted carbamoyl;

$R^b$ and $R^{b'}$ and $R^c$ and $R^{c'}$ may be taken together with the same carbon atom to which they are bonded to form a substituted or unsubstituted non-aromatic carbocycle or a substituted or unsubstituted non-aromatic heterocycle;

$R^a$, and $R^b$ bonded to a carbon atom adjacent to a nitrogen atom to which $R^a$ is bonded may be taken together with the nitrogen atom to which $R^a$ is bonded and the carbon atom to which $R^b$ is bonded to form a substituted or unsubstituted non-aromatic heterocycle; or $R^a$, and $R^c$ bonded to a carbon atom adjacent to a nitrogen atom to which $R^a$ is bonded may be taken together with the nitrogen atom to which $R^a$ is bonded and the carbon atom to which $R^c$ is bonded to form a substituted or unsubstituted non-aromatic heterocycle;

$R^b$ and $R^c$ may be taken together to form a (C1-C3) bridge, wherein one of the carbon atoms constituting the bridge may be replaced with an oxygen atom;

$R^a$ and $R^d$ may be taken together to form a (C1-C3) bridge, wherein one of the carbon atoms constituting the bridge may be replaced with an oxygen atom;

$R^5$ and $R^6$ are each independently a hydrogen atom, halogen, hydroxy, substituted or unsubstituted alkyl, or substituted or unsubstituted alkyloxy; or $R^5$ and $R^6$ may be taken together with the same carbon atom to which they are bonded to form a substituted or unsubstituted non-aromatic carbocycle;

$R^7$ is a group represented by Formula:

[Chemical formula 11]

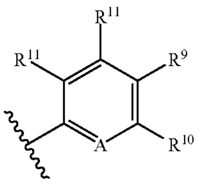

wherein A is $CR^{11}$ or N;

$R^9$ is substituted or unsubstituted alkyloxy, substituted or unsubstituted amino, substituted or unsubstituted aromatic carbocyclyloxy, substituted or unsubstituted alkyl, substituted or unsubstituted non-aromatic carbocyclyl, or cyano;

$R^{10}$ is a hydrogen atom, halogen, hydroxy, substituted or unsubstituted alkyl, or substituted or unsubstituted alkyloxy; or $R^9$ and $R^{10}$ may be taken together to form a substituted or unsubstituted non-aromatic carbocycle or a substituted or unsubstituted non-aromatic heterocycle;

$R^{11}$ is each independently a hydrogen atom, halogen, hydroxy, substituted or unsubstituted alkyl, or substituted or unsubstituted alkyloxy;

provided that (i) when a combination of ($L^1$, $L^2$) is any of ($CR^{L1}R^{L1'}$, N), (O, N), (O, $CR^{L2}$), or ($NR^{L1}$, $CR^{L2}$), n is 1 or 2;

(ii) when a combination of ($L^1$, $L^2$) is ($NR^{L1}$, N) and $R^4$ is a group represented by Formula:

[Chemical formula 12]

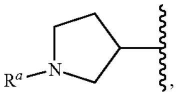

$R^a$ is not alkyl substituted with aromatic carbocyclyl or alkyl substituted with non-aromatic heterocyclyl;

provided that the following compounds are excluded:

[Chemical formula 13]

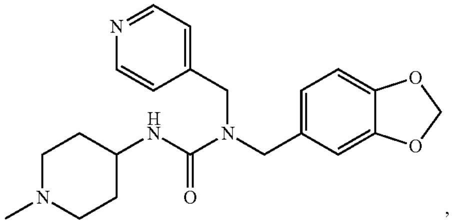

,

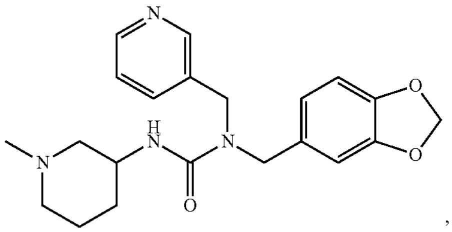

,

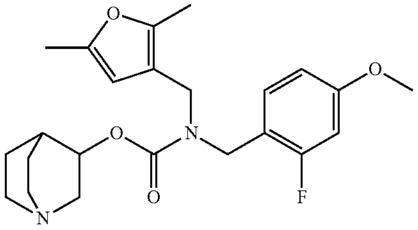

,

-continued

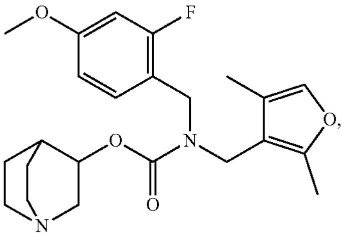

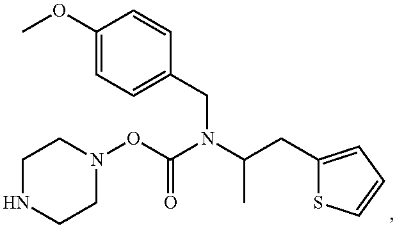

,

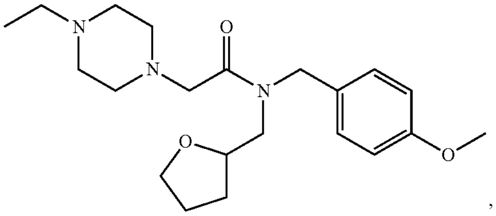

,

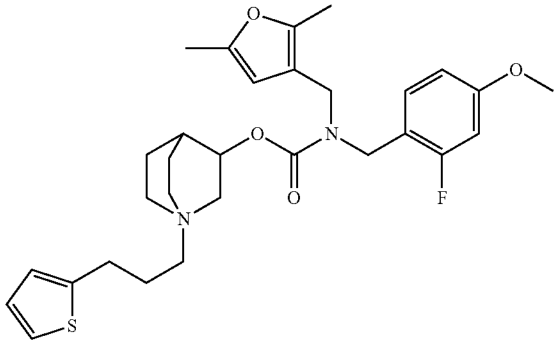

,

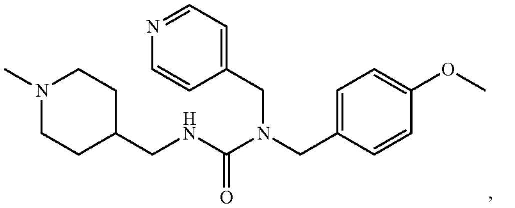

,

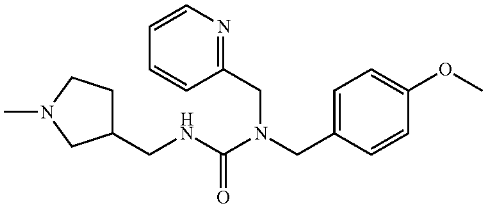

and

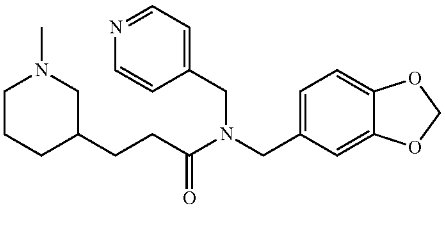

or a pharmaceutically acceptable salt thereof.

(2') The compound according to the above item (1'), wherein A is $CR^{11}$, or a pharmaceutically acceptable salt thereof.

(3') The compound according to the above item (1') or (2'), wherein A is CH, or a pharmaceutically acceptable salt thereof.

(4') The compound according to any one of the above items (1') to (3'), wherein n is 1 or 2, or a pharmaceutically acceptable salt thereof.

(5') The compound according to any one of the above items (1') to (4'), wherein the combination of ($L^1$, $L^2$) is ($NR^{L1}$, N), ($CR^{L1}R^{L1'}$, N), or (O, N), or a pharmaceutically acceptable salt thereof.

(6') The compound according to any one of the above items (1') to (5'), wherein the combination of ($L^1$, $L^2$) is (NH, N) or ($CH_2$, N), or a pharmaceutically acceptable salt thereof.

(7') The compound according to any one of the above items (1') to (6'), wherein $X^d$ is $CR^d$, and $R^d$ is a hydrogen atom or substituted or unsubstituted alkyl, or a pharmaceutically acceptable salt thereof.

(8') The compound according to any one of the above items (1') to (7'), wherein $X^d$ is CH, or a pharmaceutically acceptable salt thereof.

(9') The compound according to any one of the above items (1') to (8'), wherein p is 2, and q is 2, or a pharmaceutically acceptable salt thereof.

(10') The compound according to any one of the above items (1') to (9'), wherein $R^2$ is each independently a hydrogen atom or substituted or unsubstituted alkyl, and $R^3$ is each independently a hydrogen atom or substituted or unsubstituted alkyl, or a pharmaceutically acceptable salt thereof.

(11') The compound according to any one of the above items (1') to (10'), wherein $R^5$ and $R^6$ are each independently a hydrogen atom or substituted or unsubstituted alkyl, or a pharmaceutically acceptable salt thereof.

(12') The compound according to any one of the above items (1') to (11'), wherein $R^1$ is substituted or unsubstituted 5-membered aromatic heterocyclyl, substituted or unsubstituted pyridin-2-yl, substituted or unsubstituted pyridin-3-yl, substituted or unsubstituted pyridazin-3-yl, substituted or unsubstituted pyrimidin-2-yl, substituted or unsubstituted pyrimidin-5-yl, substituted or unsubstituted pyrazinyl, substituted or unsubstituted 9-membered aromatic heterocyclyl, substituted or unsubstituted 10-membered aromatic heterocyclyl, or substituted or unsubstituted non-aromatic heterocyclyl, or a pharmaceutically acceptable salt thereof.

(13') The compound according to any one of the above items (1') to (12'), wherein $R^1$ is substituted or unsubstituted 5-membered aromatic heterocyclyl, or a pharmaceutically acceptable salt thereof.

(14') The compound according to the above item (1'), wherein the compound is selected from the group consisting of I-016, I-028, I-043, I-077, I-080, I-084, I-086, I-087, I-096, I-099, I-101, I-102, I-104, I-105, I-113, I-115, I-116, I-117, I-118, I-121, and I-122, or a pharmaceutically acceptable salt thereof.

(15') A pharmaceutical composition comprising the compound according to any one of the above items (1') to (14') or a pharmaceutically acceptable salt thereof.

(16') The pharmaceutical composition according to the above item (14) or (15'), wherein the pharmaceutical composition is a serotonin 5-HT2A receptor antagonist and/or inverse agonist.

(17') The pharmaceutical composition according to the above item (14) or (15'), wherein the pharmaceutical composition is a serotonin 5-HT2A receptor antagonist and/or inverse agonist and a 5-HT2C receptor antagonist and/or inverse agonist.

(18') A composition for serotonin 5-HT2A receptor antagonism and/or inverse agonism comprising a compound represented by Formula (I):

[Chemical formula 14]

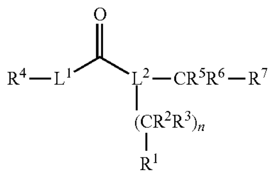

(I)

wherein $R^1$ is substituted or unsubstituted aromatic heterocyclyl or substituted or unsubstituted non-aromatic heterocyclyl;

$R^2$ is each independently a hydrogen atom, halogen, hydroxy, substituted or unsubstituted alkyl, or substituted or unsubstituted alkyloxy;

$R^3$ is each independently a hydrogen atom, halogen, hydroxy, substituted or unsubstituted alkyl, or substituted or unsubstituted alkyloxy;

n is 0, 1, or 2;

a combination of ($L^1$, $L^2$) is ($NR^{L1}$, N), ($CR^{L1}R^{L1'}$, N), (O, N), (O, $CR^{L2}$), or ($NR^{L1}$, $CR^{L2}$);

$R^{L1}$, $R^{L1'}$, and $R^{L2}$ are each independently a hydrogen atom or substituted or unsubstituted alkyl;

$R^4$ is substituted or unsubstituted non-aromatic nitrogen-containing heterocyclyl or a group represented by Formula:

[Chemical formula 15]

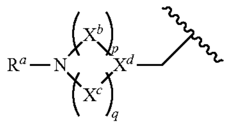

wherein p and q are each independently 1, 2, or 3;

$R^a$ is a hydrogen atom, substituted or unsubstituted alkyl, substituted or unsubstituted alkenyl, substituted or unsubstituted alkynyl, substituted or unsubstituted non-aromatic carbocyclyl, or substituted or unsubstituted non-aromatic heterocyclyl;

$X^b$ is each independently $CR^bR^{b'}$;

$X^c$ is each independently $CR^cR^{c'}$.

$R^b$ is each independently a hydrogen atom, halogen, substituted or unsubstituted alkyl, or substituted or unsubstituted alkyloxy;

$R^{b'}$ is each independently a hydrogen atom, halogen, substituted or unsubstituted alkyl, or substituted or unsubstituted alkyloxy;

$R^c$ is each independently a hydrogen atom, halogen, substituted or unsubstituted alkyl, or substituted or unsubstituted alkyloxy;

$R^{c'}$ is each independently a hydrogen atom, halogen, substituted or unsubstituted alkyl, or substituted or unsubstituted alkyloxy;

$X^d$ is $CR^d$ or N;

$R^d$ is a hydrogen atom, halogen, cyano, substituted or unsubstituted alkyl, or substituted or unsubstituted carbamoyl;

$R^b$ and $R^{b'}$ and $R^c$ and $R^{c'}$ may be taken together with the same carbon atom to which they are bonded to form a substituted or unsubstituted non-aromatic carbocycle or a substituted or unsubstituted non-aromatic heterocycle;

$R^a$, and $R^b$ bonded to a carbon atom adjacent to a nitrogen atom to which $R^a$ is bonded may be taken together with the nitrogen atom to which $R^a$ is bonded and the carbon atom to which $R^b$ is bonded to form a substituted or unsubstituted non-aromatic heterocycle; or $R^a$, and $R^c$ bonded to a carbon atom adjacent to a nitrogen atom to which $R^a$ is bonded may be taken together with the nitrogen atom to which $R^a$ is bonded and the carbon atom to which $R^c$ is bonded to form a substituted or unsubstituted non-aromatic heterocycle;

$R^b$ and $R^c$ may be taken together to form a (C1-C3) bridge, wherein one of the carbon atoms constituting the bridge may be replaced with an oxygen atom;

$R^a$ and $R^d$ may be taken together to form a (C1-C3) bridge, wherein one of the carbon atoms constituting the bridge may be replaced with an oxygen atom;

$R^5$ and $R^6$ are each independently a hydrogen atom, halogen, hydroxy, substituted or unsubstituted alkyl, or substituted or unsubstituted alkyloxy; or $R^5$ and $R^6$ may be taken together with the same carbon atom to which they are bonded to form a substituted or unsubstituted non-aromatic carbocycle;

$R^7$ is a group represented by Formula:

[Chemical formula 16]

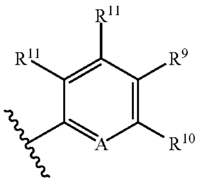

wherein A is $CR^{11}$ or N;

$R^9$ is substituted or unsubstituted alkyloxy, substituted or unsubstituted amino, substituted or unsubstituted aromatic carbocyclyloxy, substituted or unsubstituted alkyl, substituted or unsubstituted non-aromatic carbocyclyl, or cyano;

$R^{10}$ is a hydrogen atom, halogen, hydroxy, substituted or unsubstituted alkyl, or substituted or unsubstituted alkyloxy; or $R^9$ and $R^{10}$ may be taken together to form a substituted or unsubstituted non-aromatic carbocycle or a substituted or unsubstituted non-aromatic heterocycle;

$R^{11}$ is each independently a hydrogen atom, halogen, hydroxy, substituted or unsubstituted alkyl, or substituted or unsubstituted alkyloxy;

or a pharmaceutically acceptable salt thereof.

(19') The composition for serotonin 5-HT2A receptor antagonism and/or inverse agonism according to the above item (18'), wherein $R^4$ is a group represented by Formula:

[Chemical formula 17]

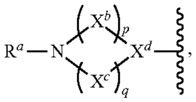, 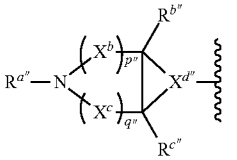 or

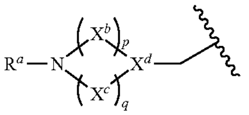

wherein p" and q" are each independently 1 or 2;

$R^{c''}$ is a hydrogen atom, substituted or unsubstituted alkyl, substituted or unsubstituted alkenyl, or substituted or unsubstituted alkynyl;

$R^{d''}$ is a hydrogen atom, halogen, substituted or unsubstituted alkyl, or substituted or unsubstituted alkyloxy;

$R^{c''}$ is a hydrogen atom, halogen, substituted or unsubstituted alkyl, or substituted or unsubstituted alkyloxy;

$X^{d''}$ is $CR^d$ or N;

each other symbol has the same meaning as the above item (18').

(20') The composition for serotonin 5-HT2A receptor antagonism and/or inverse agonism according to the above item (18') or (19'), wherein the composition for serotonin 5-HT2A receptor antagonism and/or inverse agonism is a composition for serotonin 5-HT2A receptor antagonism and/or inverse agonism and a composition for 5-HT2C receptor antagonism and/or inverse agonism.

(20) A method for treating and/or preventing a disease related to a serotonin 5-HT2A receptor comprising administering the compound according to any one of the above items (1) to (13) and (1') to (14'), or a pharmaceutically acceptable salt thereof.

(21) A method for treating and/or preventing a disease related to serotonin 5-HT2A and 5-HT2C receptors comprising administering the compound according to any one of the above items (1) to (13) and (1') to (14'), or a pharmaceutically acceptable salt thereof.

(22) The compound according to any one of the above items (1) to (13) and (1') to (14'), or a pharmaceutically acceptable salt thereof, for use in treating and/or preventing a disease related to a serotonin 5-HT2A receptor.

(23) The compound according to any one of the above items (1) to (13) and (1') to (14'), or a pharmaceutically acceptable salt thereof, for use in treating and/or preventing a disease related to serotonin 5-HT2A and 5-HT2C receptors.

(24) Use of the compound according to any one of the above items (1) to (13) and (1') to (14'), or a pharmaceutically acceptable salt thereof, for the manufacture of a medicament for treating and/or preventing a disease related to a serotonin 5-HT2A receptor.

(25) Use of the compound according to any one of the above items (1) to (13) and (1') to (14'), or a pharmaceutically acceptable salt thereof, for the manufacture of a medicament for treating and/or preventing a disease related to serotonin 5-HT2A and 5-HT2C receptors.

(26) A method for treating and/or preventing a disease related to a serotonin 5-HT2A receptor comprising administering the serotonin 5-HT2A receptor inverse agonist according to the above item (17) or (18).

(26') A method for treating and/or preventing a disease related to a serotonin 5-HT2A receptor comprising administering the composition according to the above item (18') or (19').

(27) A method for treating and/or preventing a disease related to a serotonin 5-HT2A receptor comprising administering the serotonin 5-HT2A and 5-HT2C receptor inverse agonist according to the above item (19).

(27') A method for treating and/or preventing a disease related to a serotonin 5-HT2A receptor comprising administering the composition according to the above item (20').

(28) The serotonin 5-HT2A receptor inverse agonist according to the above item (17) or (18), for use in treating and/or preventing a disease related to a serotonin 5-HT2A receptor.

(28') The composition according to the above item (18') or (19'), for use in treating and/or preventing a disease related to a serotonin 5-HT2A receptor.

(29) The serotonin 5-HT2A and 5-HT2C receptor inverse agonist according to the above item (19), for use in treating and/or preventing a disease related to serotonin 5-HT2A and 5-HT2C receptors.

(29') The composition according to the above item (20'), for use in treating and/or preventing a disease related to serotonin 5-HT2A and 5-HT2C receptors.

(30) Use of the serotonin 5-HT2A receptor inverse agonist according to the above item (17) or (18), for the manufacture of a medicament for treating and/or preventing a disease related to a serotonin 5-HT2A receptor.

(30') Use of the composition according to the above item (18') or (19'), for the manufacture of a medicament for treating and/or preventing a disease related to a serotonin 5-HT2A receptor.

(31) Use of the serotonin 5-HT2A and 5-HT2C receptor inverse agonist according to the above item (19), for the manufacture of a medicament for treating and/or preventing a disease related to serotonin 5-HT2A and 5-HT2C receptors.

(31') Use of the composition according to the above item (20'), for the manufacture of a medicament for treating and/or preventing a disease related to serotonin 5-HT2A and 5-HT2C receptors.

Effect of the Invention

The compound according to the present invention (In the present description, "the compound according to the present invention" refers to the compound of the present invention, the compound according to the 5-HT2A receptor antagonist and/or inverse agonist of the present invention, or the compound according to the pharmaceutical composition of the present invention.) has serotonin 5-HT2A receptor antagonism and/or inverse agonism, and is useful as a therapeutic agent and/or prophylactic agent for serotonin-related disease.

MODE FOR CARRYING OUT THE INVENTION

Figure 1:
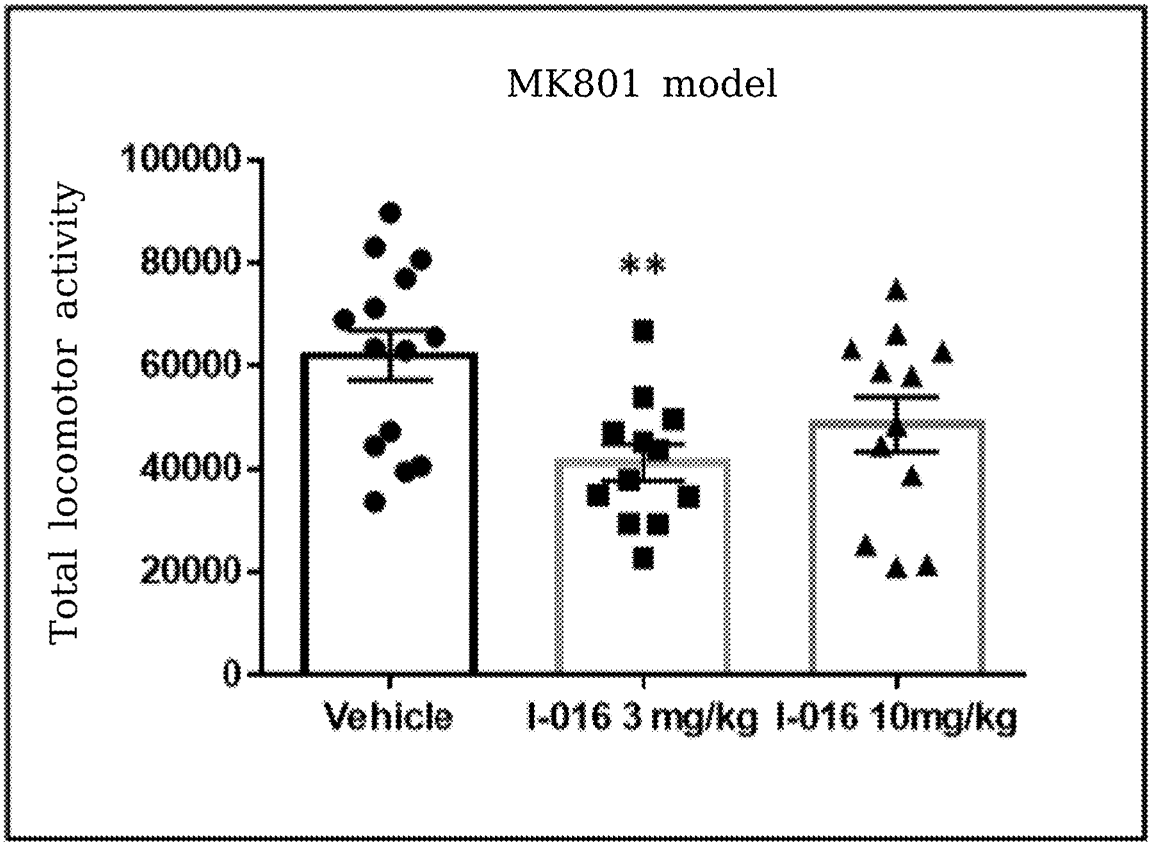
FIG. 1 shows the results of a test for inhibitory effect on rat MK801-induced hyperactivity when a vehicle and Example Compound I-016 were administered.

Terms used in this description are explained below. Each term, unless otherwise indicated, has the same meaning when it is used alone or together with other terms.

The term of "consisting of" means having only components.

The term of "comprising" means not restricting with components and not excluding undescribed factors.

Hereinafter, the present invention is described with reference to embodiments. It should be understood that, throughout the present description, the expression of a singular form includes the concept of its plural form unless specified otherwise. Accordingly, it should be understood that an article in singular form (for example, in the English language, "a", "an", and "the") includes the concept of its plural form unless specified otherwise.

Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the present invention pertains. If there is a contradiction, the present description (including definitions) precedes.

The term "halogen" includes a fluorine atom, a chlorine atom, a bromine atom, and an iodine atom. A fluorine atom and a chlorine atom are especially preferable.

The term "alkyl" includes a C1 to C15, preferably C1 to C10, more preferably C1 to C6, and further preferably C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

Preferred embodiments of "alkyl" include methyl, ethyl, n-propyl, isopropyl, n-butyl, isobutyl, sec-butyl, tert-butyl, and n-pentyl. More preferred embodiments include methyl, ethyl, n-propyl, isopropyl, and tert-butyl.

As the alkyl moiety of alkyloxy in $R^9$, C1-C4 alkyl is preferable. Examples include methyl, ethyl, n-propyl, isopropyl, n-butyl, isobutyl, sec-butyl, and tert-butyl.

When amino in $R^9$ is substituted with alkyl, C1-C4 alkyl is preferable as the alkyl. Examples include methyl, ethyl, n-propyl, isopropyl, n-butyl, isobutyl, sec-butyl, and tert-butyl.

The term "haloalkyl" means the above alkyl substituted with one or more halogen(s). When substituted with two or more halogens, the halogens may be the same or different. Examples include fluoromethyl, difluoromethyl, trifluoromethyl, chlorofluoromethyl, 2,2-difluoroethyl, 2,2,2-trifluoroethyl, 2,2-difluoropropyl, 3,3,3-trifluoropropyl, 2,2,3,3-tetrafluoropropyl, and 2,2,3,3,3-pentafluoropropyl.

The term "alkenyl" includes a C2 to C15, preferably C2 to C10, more preferably C2 to C6, and further preferably C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl.

Preferred embodiments of "alkenyl" include vinyl, allyl, propenyl, isopropenyl, and butenyl. More preferred embodiments include vinyl and n-propenyl.

The term "alkynyl" includes a C2 to C10, preferably C2 to C8, more preferably C2 to C6, and further preferably C2 to C4 linear or branched hydrocarbon group having one or more triple bond(s) at any position(s). Furthermore, it may have double bond(s) at any position(s). Examples include ethynyl, propynyl, butynyl, pentynyl, hexynyl, heptynyl, octynyl, nonynyl, and decynyl.

Preferred embodiments of "alkynyl" include ethynyl, propynyl, butynyl, and pentynyl. More preferred embodiments include ethynyl and propynyl.

The term "aromatic carbocyclyl" means a cyclic aromatic hydrocarbon group, which is monocyclic or polycyclic having two or more rings. Examples include phenyl, naphthyl, anthryl, and phenanthryl.

Preferred embodiments of the "aromatic carbocyclyl" include phenyl.

The term "aromatic carbocycle" means a ring derived from the above "aromatic carbocyclyl".

The term "non-aromatic carbocyclyl" means a cyclic saturated hydrocarbon group ωr a cyclic non-aromatic unsaturated hydrocarbon group, which is monocyclic or polycyclic having two or more rings. The "non-aromatic carbocyclyl" which is polycyclic having two or more rings includes a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge or a group to form a spiro ring as follows:

[Chemical formula 18]

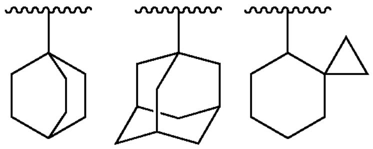

The non-aromatic carbocyclyl which is monocyclic is preferably C3 to C16, more preferably C3 to C12, and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

The non-aromatic carbocyclyl which is polycyclic having two or more rings is preferably C8 to C20, more preferably C8 to C16 carbocyclyl. Examples include indanyl, indenyl, acenaphthyl, tetrahydronaphthyl, and fluorenyl.

The term "non-aromatic carbocycle" means a ring derived from the above "non-aromatic carbocyclyl".

The term "non-aromatic carbocycle that $R^b$ and $R^{b'}$ are taken together with the same carbon atom to which they are bonded to form" and the term "non-aromatic carbocycle that $R^c$ and $R^{c'}$ are taken together with the same carbon atom to which they are bonded to form" mean rings as follows as examples.

[Chemical formula 19]

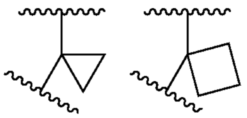

The term "non-aromatic carbocycle that $R^5$ and $R^6$ are taken together with the same carbon atom to which they are bonded to form" means non-aromatic carbocycles as follows as examples.

[Chemical formula 20]

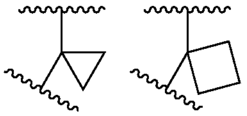

The term "non-aromatic carbocycle that $R^9$ and $R^{10}$ are taken together with the same carbon atom to which they are bonded to form" means non-aromatic carbocycles as follows as examples.

[Chemical formula 21]

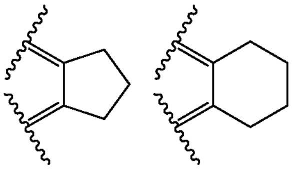

The term "aromatic heterocyclyl" means an aromatic cyclyl, which is monocyclic or polycyclic having two or more rings, containing one or more, same or different heteroatom(s) selected optionally from O, S, and N.

The aromatic heterocyclyl which is polycyclic having two or more rings includes a fused ring group wherein an aromatic heterocyclyl, which is monocyclic or polycyclic having two or more rings, is fused with a ring of the above "aromatic carbocyclyl", the bond may be held in any ring.

The aromatic heterocyclyl which is monocyclic is preferably a 5- to 8-membered ring and more preferably a 5- or 6-membered ring. Examples of the 5-membered aromatic heterocyclyl include pyrrolyl, imidazolyl, pyrazolyl, triazolyl, tetrazolyl, furyl, thienyl, isoxazolyl, oxazolyl, oxadiazolyl, isothiazolyl, thiazolyl, and thiadiazolyl. Examples of the 6-membered aromatic heterocyclyl include pyridyl, pyridazinyl, pyrimidinyl, pyrazinyl, and triazinyl.

The aromatic heterocyclyl which is bicyclic is preferably an 8- to 10-membered ring and more preferably a 9- or 10-membered ring. Examples of the aromatic heterocyclyl which is bicyclic include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl. Examples of the 9-membered aromatic heterocyclyl include indolyl, isoindolyl, indazolyl, indolizinyl, purinyl, benzimidazolyl, benzisoxazolyl, benzoxazolyl, benzoxadiazolyl, benzisothiazolyl, benzothiazolyl, benzothiadiazolyl, benzotriazolyl, benzofuranyl, imidazopyridyl, triazolopyridyl, oxazolopyridyl, and thiazolopyridyl. Examples of the 10-membered aromatic heterocyclyl include quinolinyl, isoquinolinyl, cinnolinyl, phthalazinyl, quinazolinyl, naphthyridinyl, quinoxalinyl, pteridinyl, and pyrazinopyridazinyl.

The aromatic heterocyclyl which is polycyclic having three or more rings is preferably a 13- to 15-membered ring. Examples of the aromatic heterocyclyl which is polycyclic having three or more rings include carbazolyl, acridinyl, xanthenyl, phenothiazinyl, phenoxathiinyl, phenoxazinyl, and dibenzofuryl.

The term "aromatic nitrogen-containing heterocyclyl" means an aromatic heterocyclyl, which is monocyclic or polycyclic having two or more rings, containing one or more N and optionally containing one or more, same or different heteroatom(s) selected optionally from O or S. The aromatic nitrogen-containing heterocyclyl which is polycyclic having two or more rings includes a fused ring group wherein an aromatic nitrogen-containing heterocyclyl, which is monocyclic or polycyclic having two or more rings, is fused with a ring of the above "aromatic carbocyclyl", the bond may be held in any ring.

The aromatic nitrogen-containing heterocyclyl which is monocyclic is preferably a 5- to 8-membered ring and more preferably a 5- or 6-membered ring. Examples of the 5-membered aromatic nitrogen-containing heterocyclyl include pyrrolyl, imidazolyl, pyrazolyl, triazolyl, tetrazolyl, isoxazolyl, oxazolyl, oxadiazolyl, isothiazolyl, thiazolyl, and thiadiazolyl. Examples of the 6-membered aromatic nitrogen-containing heterocyclyl include pyridyl, pyridazinyl, pyrimidinyl, pyrazinyl, and triazinyl.

The aromatic nitrogen-containing heterocyclyl which is bicyclic is preferably an 8- to 10-membered ring and more preferably a 9- or 10-membered ring. Examples of the aromatic nitrogen-containing heterocyclyl which is bicyclic include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzotriazolyl, imidazopyridyl, triazolopyridyl, imidazothiazolyl, pyrazinopyridazinyl, oxazolopyridyl, and thiazolopyridyl.

The aromatic nitrogen-containing heterocyclyl which is polycyclic having three or more rings is preferably a 13- to 15-membered ring. Examples of the aromatic nitrogen-containing heterocyclyl which is polycyclic having three or more rings include carbazolyl, acridinyl, and phenothiazinyl.

The term "non-aromatic heterocyclyl" means a non-aromatic cyclyl, which is monocyclic or polycyclic having two or more rings, containing one or more, same or different heteroatom(s) selected optionally from O, S, and N. The "non-aromatic heterocyclyl" which is polycyclic having two or more rings includes a non-aromatic heterocyclyl, which is monocyclic or polycyclic having two or more rings, fused with a ring of the above "aromatic carbocyclyl", "non-aromatic carbocyclyl", and/or "aromatic heterocyclyl", and further includes a non-aromatic carbocyclyl, which is monocyclic or polycyclic having two or more rings, fused with a ring of the above "aromatic heterocyclyl", the bond may be held in any ring.

In addition, examples of the "non-aromatic heterocyclyl" also include a group having a bridge or a group to form a spiro ring as follows:

[Chemical formula 22]

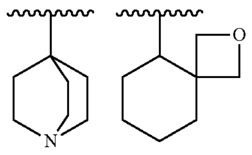

The non-aromatic heterocyclyl which is monocyclic is preferably a 3- to 8-membered ring and more preferably a 5- or 6-membered ring.

Examples of the 3-membered non-aromatic heterocyclyl include thiiranyl, oxiranyl, and aziridinyl. Examples of the 4-membered non-aromatic heterocyclyl include oxetanyl and azetidinyl. Examples of the 5-membered non-aromatic heterocyclyl include oxathiolanyl, thiazolidinyl, pyrrolidinyl, pyrrolinyl, imidazolidinyl, imidazolinyl, pyrazolidinyl, pyrazolinyl, tetrahydrofuryl, dihydrothiazolyl, tetrahydroisothiazolyl, dioxolanyl, dioxolyl, and thiolanyl. Examples of the 6-membered non-aromatic heterocyclyl include dioxanyl, thianyl, piperidyl, piperazinyl, morpholinyl, morpholino, thiomorpholinyl, thiomorpholino, dihydropyridyl, tetrahydropyridyl, tetrahydropyranyl, dihydrooxazinyl, tetrahydropyridazinyl, hexahydropyrimidinyl, dioxazinyl, thiinyl, and thiazinyl. Examples of the 7-membered non-aromatic heterocyclyl include hexahydroazepinyl, tetrahydrodiazepinyl, and oxepanyl. Examples of the 8-membered non-aromatic heterocyclyl include azocane, thiocane, and oxocane.

The non-aromatic heterocyclyl which is polycyclic having two or more rings is preferably an 8- to 20-membered ring and more preferably an 8- to 10-membered ring. Examples of the non-aromatic heterocyclyl which is polycyclic having two or more rings include indolinyl, isoindolinyl, chromanyl, and isochromanyl.

The term "non-aromatic nitrogen-containing heterocyclyl" means a non-aromatic heterocyclyl, which is monocyclic or polycyclic having two or more rings, containing one or more nitrogen atoms. The "non-aromatic heterocyclyl" which is polycyclic having two or more rings includes a non-aromatic nitrogen-containing heterocyclyl, which is monocyclic or polycyclic having two or more rings, fused with a ring of the above "aromatic carbocyclyl", "non-aromatic carbocyclyl", and/or "aromatic heterocyclyl", the bond may be held in any ring.

Examples include rings as follows:

[Chemical formula 23]

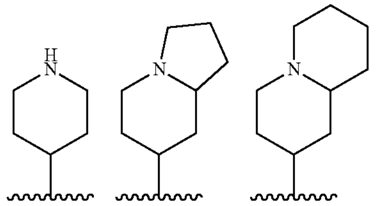

Furthermore, the "non-aromatic nitrogen-containing heterocyclyl" also include a group having a bridge or a group to form a spiro ring as follows:

[Chemical formula 24]

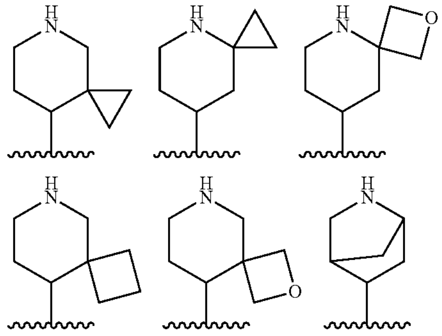

The term "non-aromatic heterocycle" means a ring derived from the above "non-aromatic heterocyclyl".

The term "non-aromatic heterocycle that $R^b$ and $R^{b'}$ are taken together with the same carbon atom to which they are bonded to form" and the term "non-aromatic heterocycle that $R^c$ and $R^{c'}$ are taken together with the same carbon atom to which they are bonded to form" mean rings as follows as examples.

[Chemical formula 25]

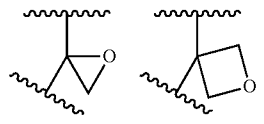

The term "non-aromatic heterocycle that $R^a$, and $R^b$ bonded to a carbon atom adjacent to a nitrogen atom to which $R^a$ is bonded are taken together with the nitrogen atom to which $R^a$ is bonded and the carbon atom to which $R^b$ is bonded to form" and the term "non-aromatic heterocycle that $R^a$, and $R^c$ bonded to a carbon atom adjacent to a nitrogen atom to which $R^a$ is bonded are taken together with the nitrogen atom to which $R^a$ is bonded and the carbon atom to which $R^c$ is bonded to form" mean rings as follows as examples.

[Chemical formula 26]

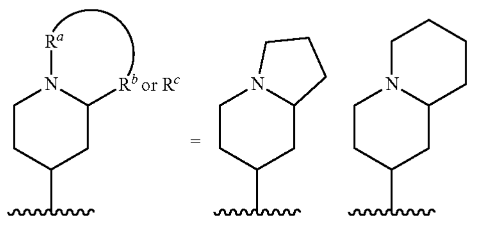

wherein each symbol has the same meaning as the above item (1').

The term "non-aromatic heterocycle that $R^9$ and $R^{10}$ are taken together to form" means rings as follows as examples.

[Chemical formula 27]

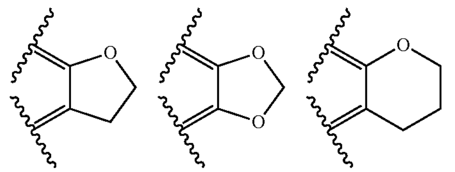

When $R^b$ and $R^{b'}$ and $R^c$ and $R^{c'}$ are taken together with the same carbon atom to which they are bonded to form a substituted or unsubstituted non-aromatic carbocycle, $R^4$ includes groups as follows as examples.

[Chemical formula 28]

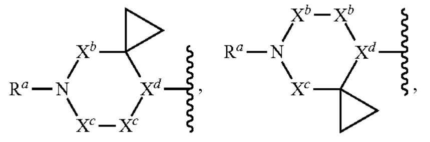

wherein each symbol has the same meaning as the above item (1').

The term "trialkylsilyl" means a group in which the above three "alkyls" are bound to a silicon atom. The three alkyls may be the same or different. Examples include trimethylsilyl, triethylsilyl, and tert-butyldimethylsilyl.

In the present description, the phrase "may be substituted with substituent group α" means that "may be substituted with one or more group(s) selected from substituent group α". The same also applies to substituent groups β, γ, and γ'.

Substituents for "substituted alkyl", "substituted alkenyl", "substituted alkynyl", "substituted alkyloxy", "substituted alkenyloxy", "substituted alkynyloxy", "substituted alkylcarbonyloxy", "substituted alkenylcarbonyloxy", "substituted alkynylcarbonyloxy", "substituted alkylcarbonyl", "substituted alkenylcarbonyl", "substituted alkynylcarbonyl", "substituted alkyloxycarbonyl", "substituted alkenyloxycarbonyl", "substituted alkynyloxycarbonyl", "substituted alkylsulfanyl", "substituted alkenylsulfanyl", "substituted alkynylsulfanyl", "substituted alkylsulfinyl", "substituted alkenylsulfinyl", "substituted alkynylsulfinyl", "substituted alkylsulfonyl", "substituted alkenylsulfonyl", "substituted alkynylsulfonyl", and the like include the following substituent group A. A carbon atom at any position may be bonded to one or more group(s) selected from the following substituent group A.

Substituent group A: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azide, hydrazino, ureido, amidino, guanidino, pentafluorothio, trialkylsilyl, alkyloxy which may be substituted with substituent group α, alkenyloxy which may be substituted with substituent group α, alkynyloxy which may be substituted with substituent group α, alkylcarbonyloxy which may be substituted with substituent group α, alkenylcarbonyloxy which may be substituted with substituent group α, alkynylcarbonyloxy which may be substituted with substituent group α, alkylcarbonyl which may be substituted with substituent group α, alkenylcarbonyl which may be substituted with substituent group α, alkynylcarbonyl which may be substituted with substituent group α, alkyloxycarbonyl which may be substituted with substituent group α, alkenyloxycarbonyl which may be substituted with substituent group α, alkynyloxycarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, amino which may be substituted with substituent group β, imino which may be substituted with substituent group β, carbamoyl which may be substituted with substituent group β, sulfamoyl which may be substituted with substituent group β, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclyloxy which may be substituted with substituent group γ, non-aromatic carbocyclyloxy which may be substituted with substituent group γ', aromatic heterocyclyloxy which may be substituted with substituent group γ, non-aromatic heterocyclyloxy which may be substituted with substituent group γ', aromatic carbocyclylcarbonyloxy which may be substituted with substituent group γ, non-aromatic carbocyclylcarbonyloxy which may be substituted with substituent group γ', aromatic heterocyclylcarbonyloxy which may be substituted with substituent group γ, non-aromatic heterocyclylcarbonyloxy which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylalkyloxy which may be substituted with substituent group γ, non-aromatic carbocyclylalkyloxy which may be substituted with substituent group γ', aromatic heterocyclylalkyloxy which may be substituted with substituent group γ, non-aromatic heterocyclylalkyloxy which may be substituted with substituent group γ', aromatic carbocyclylalkyloxycarbonyl which may be substituted with substituent group γ, non-aromatic carbocyclylalkyloxycarbonyl which may be substituted with substituent group γ', aromatic heterocyclylalkyloxycarbonyl which may be substituted with substituent group γ, non-aromatic heterocyclylalkyloxycarbonyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

Substituent group α: halogen, hydroxy, carboxy, alkyloxy, haloalkyloxy, alkenyloxy, alkynyloxy, sulfanyl, and cyano.

Substituent group β: halogen, hydroxy, carboxy, cyano, alkyl which may be substituted with substituent group α, alkenyl which may be substituted with substituent group α, alkynyl which may be substituted with substituent group α, alkylcarbonyl which may be substituted with substituent group α, alkenylcarbonyl which may be substituted with substituent group α, alkynylcarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclylalkyl which may be substituted with substituent group γ, non-aromatic carbocyclylalkyl which may be substituted with substituent group γ', aromatic heterocyclylalkyl which may be substituted with substituent group γ, non-aromatic heterocyclylalkyl which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

Substituent group γ: substituent group α, alkyl, haloalkyl, hydroxyalkyl, alkenyl, alkynyl, alkylcarbonyl, haloalkylcarbonyl, alkenylcarbonyl, and alkynylcarbonyl.

Substituent group γ': substituent group γ and oxo.

The substituents on the rings of "aromatic carbocycle" and "aromatic heterocycle", such as "substituted aromatic carbocyclyl", "substituted aromatic heterocyclyl", "substituted aromatic nitrogen-containing heterocyclyl", "substituted aromatic carbocyclyloxy", "substituted aromatic heterocyclyloxy", "substituted aromatic carbocyclylcarbonyloxy", "substituted aromatic heterocyclylcarbonyloxy", "substituted aromatic carbocyclylcarbonyl", "substituted aromatic heterocyclylcarbonyl", "substituted aromatic carbocyclyloxycarbonyl", "substituted aromatic heterocyclyloxycarbonyl", "substituted aromatic carbocyclylsulfanyl", "substituted aromatic heterocyclylsulfanyl", "substituted aromatic carbocyclylsulfinyl", "substituted aromatic heterocyclylsulfinyl", "substituted aromatic carbocyclylsulfonyl", and "substituted aromatic heterocyclylsulfonyl" include the following substituent group B. An atom at any position on the ring may be bonded to one or more group(s) selected from the following substituent group B.

Substituent group B: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azide, hydrazino, ureido, amidino, guanidino, pentafluorothio, trialkylsilyl, alkyl which may be substituted with substituent group α, alkenyl which may be substituted with substituent group α, alkynyl which may be substituted with substituent group α, alkyloxy which may be substituted with substituent group α, alkenyloxy which may be substituted with substituent group α, alkynyloxy which may be substituted with substituent group α, alkylcarbonyloxy which may be substituted with substituent group α, alkenylcarbonyloxy which may be substituted with substituent group α, alkynylcarbonyloxy which may be substituted with substituent group α, alkylcarbonyl which may be substituted with substituent group α, alkenylcarbonyl which may be substituted with substituent group α, alkynylcarbonyl which may be substituted with substituent group α, alkyloxycarbonyl which may be substituted with substituent group α, alkenyloxycarbonyl which may be substituted with substituent group α, alkynyloxycarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, amino which may be substituted with substituent group β, imino which may be substituted with substituent group β, carbamoyl which may be substituted with substituent group β, sulfamoyl which may be substituted with substituent group β, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclyloxy which may be substituted with substituent group γ, non-aromatic carbocyclyloxy which may be substituted with substituent group γ', aromatic heterocyclyloxy which may be substituted with substituent group γ, non-aromatic heterocyclyloxy which may be substituted with substituent group γ', aromatic carbocyclylcarbonyloxy which may be substituted with substituent group γ, non-aromatic carbocyclylcarbonyloxy which may be substituted with substituent group γ', aromatic heterocyclylcarbonyloxy which may be substituted with substituent group γ, and non-aromatic heterocyclylcarbonyloxy which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylalkyl which may be substituted with substituent group γ, non-aromatic carbocyclylalkyl which may be substituted with substituent group γ', aromatic heterocyclylalkyl which may be substituted with substituent group γ, non-aromatic heterocyclylalkyl which may be substituted with substituent group γ', aromatic carbocyclylalkyloxy which may be substituted with substituent group γ, non-aromatic carbocyclylalkyloxy which may be substituted with substituent group γ', aromatic heterocyclylalkyloxy which may be substituted with substituent group γ, non-aromatic heterocyclylalkyloxy which may be substituted with substituent group γ', aromatic carbocyclylalkyloxycarbonyl which may be substituted with substituent group γ, non-aromatic carbocyclylalkyloxycarbonyl which may be substituted with substituent group γ', aromatic heterocyclylalkyloxycarbonyl which may be substituted with substituent group γ, non-aromatic heterocyclylalkyloxycarbonyl which may be substituted with substituent group γ', aromatic carbocyclylalkyloxyalkyl which may be substituted with substituent group γ, non-aromatic carbocyclylalkyloxyalkyl which may be substituted with substituent group γ', aromatic heterocyclylalkyloxyalkyl which may be substituted with substituent group γ, non-aromatic heterocyclylalkyloxyalkyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

The substituents on the ring of "non-aromatic carbocycle" and "non-aromatic heterocycle" of "substituted non-aromatic carbocyclyl", "substituted non-aromatic heterocyclyl", "substituted non-aromatic nitrogen-containing heterocyclyl", "substituted non-aromatic heterocycle that $R^9$ and $R^{10}$ are taken together to form", "substituted non-aromatic carbocycle that $R^{22}$ and $R^{23}$ are taken together with the carbon atom to which they are bonded to form", "substituted non-aromatic carbocyclyloxy", "substituted non-aromatic heterocyclyloxy", "substituted non-aromatic carbocyclylcarbonyloxy", "substituted non-aromatic heterocyclylcarbonyloxy", "substituted non-aromatic carbocyclylcarbonyl", "substituted non-aromatic heterocyclylcarbonyl", "substituted non-aromatic carbocyclyloxycarbonyl", "substituted non-aromatic heterocyclyloxycarbonyl", "substituted non-aromatic carbocyclylsulfanyl", "substituted non-aromatic heterocyclylsulfanyl", "substituted non-aromatic carbocyclylsulfinyl", "substituted non-aromatic heterocyclylsulfinyl", "substituted non-aromatic carbocyclylsulfonyl", "substituted non-aromatic heterocyclylsulfonyl", "substituted non-aromatic carbocycle that $R^b$ and $R^{b'}$ are taken together with the same carbon atom to which they are bonded to form", "substituted non-aromatic carbocycle that $R^c$ and $R^{c'}$ are taken together with the same carbon atom to which they are bonded to form", "substituted non-aromatic heterocycle that $R^b$ and $R^{b'}$ are taken together with the same carbon atom to which they are bonded to form", "substituted non-aromatic heterocycle that $R^c$ and $R^{c'}$ are taken together with the same carbon atom to which they are bonded to form", "substituted non-aromatic heterocycle that $R^a$, and $R^b$ bonded to a carbon atom adjacent to a nitrogen atom to which $R^a$ is bonded are taken together with the nitrogen atom to which $R^a$ is bonded and the carbon atom to which $R^b$ is bonded to form", "substituted non-aromatic heterocycle that $R^a$, and $R^c$ bonded to a carbon atom adjacent to a nitrogen atom to which $R^a$ is bonded are taken together with the nitrogen atom to which $R^a$ is bonded and the carbon atom to which $R^c$ is bonded to form", "substituted non-aromatic carbocycle that $R^5$ and $R^6$ are taken together with the same carbon atom to which they are bonded to form", "substituted non-aromatic carbocycle that $R^9$ and $R^{10}$ are taken together to form", and "substituted non-aromatic heterocycle that $R^9$ and $R^{10}$ are taken together to form" include the following substituent group C. An atom at any position on the ring may be bonded to one or more group(s) selected from the following substituent group C.

Substituent group C: substituent group B and oxo.

When the "non-aromatic carbocycle", the "non-aromatic heterocycle", and the "non-aromatic nitrogen-containing heterocycle" are substituted with "oxo", this means a ring in which two hydrogen atoms on a carbon atom are substituted as follows:

[Chemical formula 29]

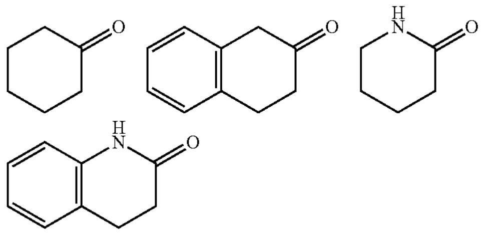

The substituents for "substituted amino", "substituted imino", "substituted carbamoyl", and "substituted sulfamoyl" include the following substituent group D. These moieties may be substituted with one or two group(s) selected from substituent group D.

Substituent group D: halogen, hydroxy, carboxy, cyano, alkyl which may be substituted with substituent group α, alkenyl which may be substituted with substituent group α, alkynyl which may be substituted with substituent group α, alkylcarbonyl which may be substituted with substituent group α, alkenylcarbonyl which may be substituted with substituent group α, alkynylcarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, amino which may be substituted with substituent group β, imino which may be substituted with substituent group β, carbamoyl which may be substituted with substituent group β, sulfamoyl which may be substituted with substituent group β, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclylalkyl which may be substituted with substituent group γ, non-aromatic carbocyclylalkyl which may be substituted with substituent group γ', aromatic heterocyclylalkyl which may be substituted with substituent group γ, non-aromatic heterocyclylalkyl which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

With regard to a compound represented by Formula (I), preferred embodiments of $R^1$, $R^2$, $R^3$, n, a combination of ($L^1$, $L^2$), $R^{L1}$, $R^{L1'}$, $R^{L2}$, $R^4$, p, q, p", q", $R^a$, $R^{a''}$, $R^b$, $R^{b'}$, $R^c$, $R^{c'}$, $R^{b''}$, $R^{c''}$, $X^d$, $X^{d''}$, $R^d$, $R^5$, $R^6$, $R^7$, A, $R^9$, $R^{10}$, and $R^{11}$ will be shown below. Regarding the compound represented by Formula (I), embodiments of all the combinations of specific examples shown below are mentioned as examples.

$R^1$ may be substituted or unsubstituted aromatic heterocyclyl, or substituted or unsubstituted non-aromatic heterocyclyl (hereinafter, referred to as A-1).

$R^1$ may be substituted or unsubstituted aromatic heterocyclyl (hereinafter, referred to as A-2).

$R^1$ may be substituted or unsubstituted 5-membered aromatic heterocyclyl, substituted or unsubstituted pyridin-2-yl, substituted or unsubstituted pyridin-3-yl, substituted or unsubstituted pyridazin-3-yl, substituted or unsubstituted pyrimidin-2-yl, substituted or unsubstituted pyrimidin-5-yl, substituted or unsubstituted pyrazinyl, substituted or unsubstituted 9-membered aromatic heterocyclyl, substituted or unsubstituted 10-membered aromatic heterocyclyl, or substituted or unsubstituted non-aromatic heterocyclyl (hereinafter, referred to as A-3).

$R^1$ may be substituted or unsubstituted 5-membered aromatic heterocyclyl, or substituted or unsubstituted 6-membered aromatic heterocyclyl (hereinafter, referred to as A-4).

$R^1$ may be substituted or unsubstituted 5-membered aromatic heterocyclyl, substituted or unsubstituted pyridin-2-yl, substituted or unsubstituted pyridin-3-yl, substituted or unsubstituted pyridazin-3-yl, substituted or unsubstituted pyrimidin-2-yl, substituted or unsubstituted pyrimidin-5-yl, or substituted or unsubstituted pyrazinyl (hereinafter, referred to as A-5).

$R^1$ may be substituted or unsubstituted 5-membered aromatic heterocyclyl (hereinafter, referred to as A-6).

$R^1$ may be substituted or unsubstituted pyridin-2-yl, substituted or unsubstituted pyridin-3-yl, substituted or unsubstituted pyridazin-3-yl, substituted or unsubstituted pyrimidin-2-yl, substituted or unsubstituted pyrimidin-5-yl, or substituted or unsubstituted pyrazinyl (hereinafter, referred to as A-7).

$R^1$ may be substituted or unsubstituted pyrazolyl, substituted or unsubstituted pyridyl, substituted or unsubstituted pyrrolyl, substituted or unsubstituted furyl, substituted or unsubstituted thiophenyl, substituted or unsubstituted oxazolyl, substituted or unsubstituted triazolyl, substituted or unsubstituted isoxazolyl, substituted or unsubstituted pyrazinyl, substituted or unsubstituted pyrimidinyl, or substituted or unsubstituted benzofuranyl (hereinafter, referred to as A-8).

$R^1$ may be substituted or unsubstituted pyrazolyl, substituted or unsubstituted pyridin-2-yl, substituted or unsubstituted pyridin-3-yl, substituted or unsubstituted pyrrolyl, substituted or unsubstituted furyl, substituted or unsubstituted thiophenyl, substituted or unsubstituted oxazolyl, substituted or unsubstituted triazolyl, substituted or unsubstituted isoxazolyl, substituted or unsubstituted pyrazinyl, substituted or unsubstituted pyrimidin-2-yl, substituted or unsubstituted pyrimidin-5-yl, or substituted or unsubstituted benzofuranyl (hereinafter, referred to as A-9).

$R^1$ may be pyrazolyl which may be substituted with substituent group B, pyridin-2-yl which may be substituted with substituent group B, pyridin-3-yl which may be substituted with substituent group B, pyrrolyl which may be substituted with substituent group B, furyl which may be substituted with substituent group B, thiophenyl which may be substituted with substituent group B, oxazolyl which may be substituted with substituent group B, triazolyl which may be substituted with substituent group B, isoxazolyl which may be substituted with substituent group B, pyrazinyl which may be substituted with substituent group B, pyrimidin-2-yl which may be substituted with substituent group B, pyrimidin-5-yl which may be substituted with substituent group B, or benzofuranyl which may be substituted with substituent group B (hereinafter, referred to as A-10).

$R^1$ may be pyrazolyl which may be substituted with substituent group ω, pyridin-2-yl which may be substituted with substituent group ω, pyridin-3-yl which may be substituted with substituent group ω, pyrrolyl which may be substituted with substituent group ω, furyl which may be substituted with substituent group ω, thiophenyl which may be substituted with substituent group ω, oxazolyl which may be substituted with substituent group ω, triazolyl which may be substituted with substituent group ω, isoxazolyl which may be substituted with substituent group ω, pyrazinyl which may be substituted with substituent group ω, pyrimidin-2-yl which may be substituted with substituent group ω, pyrimidin-5-yl which may be substituted with substituent group ω, or benzofuranyl which may be substituted with substituent group ω(substituent group ω: halogen, cyano, haloalkyl, and unsubstituted alkyl) (hereinafter, referred to as A-11).

$R^1$ may be substituted or unsubstituted pyrazolyl (hereinafter, referred to as A-12).

$R^1$ may be pyrazolyl substituted with substituent group ω' (substituent group ω': halogen, haloalkyl, non-aromatic carbocyclyl, and unsubstituted alkyl) (hereinafter, referred to as A-13).

$R^1$ may be pyrazolyl substituted with substituent group ω"(substituent group ω": haloalkyl, unsubstituted alkyl, and non-aromatic carbocyclyl) (hereinafter, referred to as A-14).

$R^1$ may be pyrazolyl substituted with alkyl (hereinafter, referred to as A-15).

$R^1$ may be pyrazolyl substituted with haloalkyl (hereinafter, referred to as A-16).

$R^1$ may be pyrazolyl substituted with non-aromatic carbocyclyl (hereinafter, referred to as A-17).

$R^1$ may be substituted or unsubstituted furyl (hereinafter, referred to as A-18).

$R^1$ may be furyl substituted with substituent group ω' (substituent group ω': halogen, haloalkyl, non-aromatic carbocyclyl, and unsubstituted alkyl) (hereinafter, referred to as A-19).

$R^1$ may be unsubstituted furyl (hereinafter, referred to as A-20).

$R^1$ may be substituted or unsubstituted pyridin-2-yl (hereinafter, referred to as A-21).

$R^1$ may be pyridin-2-yl substituted with substituent group ω' (substituent group ω': halogen, haloalkyl, non-aromatic carbocyclyl, and unsubstituted alkyl) (hereinafter, referred to as A-22).

$R^1$ may be pyridin-2-yl substituted with halogen (hereinafter, referred to as A-23).

$R^1$ may be substituted or unsubstituted oxazolyl (hereinafter, referred to as A-24).

$R^1$ may be oxazolyl substituted with substituent group ω' (substituent group ω': halogen, haloalkyl, non-aromatic carbocyclyl, and unsubstituted alkyl) (hereinafter, referred to as A-25).

$R^1$ may be oxazolyl substituted with substituent group ω"(substituent group ω": haloalkyl, unsubstituted alkyl, and unsubstituted non-aromatic carbocyclyl) (hereinafter, referred to as A-26).

$R^1$ may be oxazolyl substituted with alkyl (hereinafter, referred to as A-27).

$R^1$ may be oxazolyl substituted with haloalkyl (hereinafter, referred to as A-28).

$R^1$ may be oxazolyl substituted with non-aromatic carbocyclyl (hereinafter, referred to as A-29).

$R^1$ may be substituted or unsubstituted triazolyl (hereinafter, referred to as A-30).

$R^1$ may be triazolyl substituted with substituent group ω' (substituent group ω': halogen, haloalkyl, non-aromatic carbocyclyl, and unsubstituted alkyl) (hereinafter, referred to as A-31).

$R^1$ may be triazolyl substituted with substituent group ω"(substituent group ω": haloalkyl, unsubstituted alkyl, and unsubstituted non-aromatic carbocyclyl) (hereinafter, referred to as A-32).

$R^1$ may be triazolyl substituted with alkyl (hereinafter, referred to as A-33).

$R^1$ may be triazolyl substituted with haloalkyl (hereinafter, referred to as A-34).

$R^1$ may be triazolyl substituted with non-aromatic carbocyclyl (hereinafter, referred to as A-35).

$R^2$ may be each independently a hydrogen atom, halogen, hydroxy, substituted or unsubstituted alkyl, or substituted or unsubstituted alkyloxy (hereinafter, referred to as B-1).

$R^2$ may be each independently a hydrogen atom or substituted or unsubstituted alkyl (hereinafter, referred to as B-2).

$R^2$ may be each independently a hydrogen atom (hereinafter, referred to as B-3).

$R^3$ may be each independently a hydrogen atom, halogen, hydroxy, substituted or unsubstituted alkyl, or substituted or unsubstituted alkyloxy (hereinafter, referred to as C-1).

$R^3$ may be each independently a hydrogen atom or substituted or unsubstituted alkyl (hereinafter, referred to as C-2).

$R^3$ may be each independently a hydrogen atom (hereinafter, referred to as C-3).

n may be 0, 1, or 2 (hereinafter, referred to as D-1).

n may be 0 or 1 (hereinafter, referred to as D-2).

n may be 1 or 2 (hereinafter, referred to as D-3).

n may be 0 (hereinafter, referred to as D-4).

n may be 1 (hereinafter, referred to as D-5).

n may be 2 (hereinafter, referred to as D-6).

The combination of ($L^1$, $L^2$) may be ($NR^{L1}$, N), ($CR^{L1}R^{L1'}$, N), (O, N), (0, $CR^{L2}$), or ($NR^{L1}$, $CR^{L2}$) (hereinafter, referred to as E-1).

The combination of ($L^1$, $L^2$) may be ($NR^{L1}$, N), ($CR^{L1}R^{L1'}$, N), or (O, N) (hereinafter, referred to as E-2).

The combination of ($L^1$, $L^2$) may be ($NR^{L1}$, N) or ($CR^{L1}R^{L1'}$, N) (hereinafter, referred to as E-3).

The combination of ($L^1$, $L^2$) may be ($NR^{L1}$, N) or (O, N) (hereinafter, referred to as E-4).

The combination of ($L^1$, $L^2$) may be ($NR^{L1}$, N) (hereinafter, referred to as E-5).

The combination of ($L^1$, $L^2$) may be ($CR^{L1}R^{L1'}$, N) (hereinafter, referred to as E-6).

The combination of ($L^1$, $L^2$) may be (O, N) (hereinafter, referred to as E-7).

The combination of ($L^1$, $L^2$) may be (O, $CR^{L2}$) (hereinafter, referred to as E-8).

The combination of ($L^1$, $L^2$) may be ($NR^{L1}$, $CR^{L2}$) (hereinafter, referred to as E-9).

The combination of ($L^1$, $L^2$) may be (NH, N), ($CH_2$, N), (O, N), (O, CH), or (NH, CH) (hereinafter, referred to as E-10).

The combination of ($L^1$, $L^2$) may be (NH, N), ($CH_2$, N), or (O, N) (hereinafter, referred to as E-11).

The combination of ($L^1$, $L^2$) may be (NH, N) or ($CH_2$, N) (hereinafter, referred to as E-12).

The combination of ($L^1$, $L^2$) may be (NH, N) or (O, N) (hereinafter, referred to as E-13).

The combination of ($L^1$, $L^2$) may be (NH, N) (hereinafter, referred to as E-14).

The combination of ($L^1$, $L^2$) may be ($CH_2$, N) (hereinafter, referred to as E-15).

The combination of ($L^1$, $L^2$) may be (O, N) (hereinafter, referred to as E-16).

$R^{L1}$, $R^{L1'}$, and $R^{L2}$ may be each independently a hydrogen atom, halogen, or substituted or unsubstituted alkyl (hereinafter, referred to as F-1).

$R^{L1}$ may be a hydrogen atom, halogen, or substituted or unsubstituted alkyl (hereinafter, referred to as F-2).

$R^{L1}$ may be a hydrogen atom or halogen (hereinafter, referred to as F-3).

$R^{L1}$ may be a hydrogen atom or a fluorine atom (hereinafter, referred to as F-4).

$R^{L1}$ may be a hydrogen atom (hereinafter, referred to as F-5).

$R^{L1'}$ may be a hydrogen atom, halogen, or substituted or unsubstituted alkyl (hereinafter, referred to as F-6).

$R^{L1'}$ may be a hydrogen atom or halogen (hereinafter, referred to as F-7).

$R^{L1'}$ may be a hydrogen atom or a fluorine atom (hereinafter, referred to as F-8).

$R^{L1'}$ may be a hydrogen atom (hereinafter, referred to as F-9).

$R^{L2}$ may be a hydrogen atom or substituted or unsubstituted alkyl (hereinafter, referred to as F-10).

$R^{L2}$ may be a hydrogen atom or halogen (hereinafter, referred to as F-11).

$R^{L2}$ may be a hydrogen atom or a fluorine atom (hereinafter, referred to as F-12).

$R^{L2}$ may be a hydrogen atom (hereinafter, referred to as F-13).

$R^4$ may be substituted or unsubstituted non-aromatic nitrogen-containing heterocyclyl (hereinafter, referred to as G-1).

$R^4$ may be substituted or unsubstituted 4- to 7-membered non-aromatic nitrogen-containing heterocyclyl (hereinafter, referred to as G-2).

$R^4$ may be substituted or unsubstituted 6-membered non-aromatic nitrogen-containing heterocyclyl (hereinafter, referred to as G-3).

$R^4$ may be a group represented by Formula:

[Chemical formula 30]

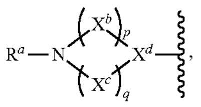
,
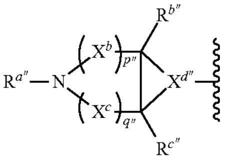
or
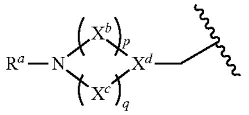

wherein each symbol has the same meaning as the above item (1') (hereinafter, referred to as G-4).

$R^4$ may be a group represented by Formula:

[Chemical formula 31]

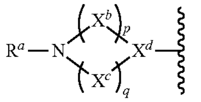
or
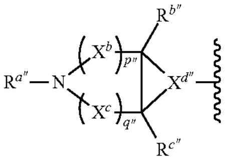

wherein each symbol has the same meaning as the above item (1') (hereinafter, referred to as G-5).

$R^4$ may be a group represented by Formula:

[Chemical formula 32]

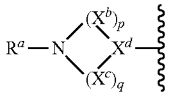

wherein each symbol has the same meaning as the above item (1') (hereinafter, referred to as G-6).

$R^4$ may be a group represented by Formula:

[Chemical formula 33]

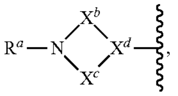
,
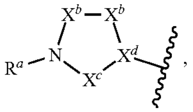
,
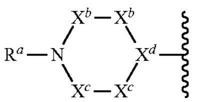
or
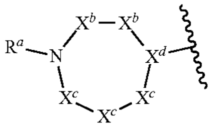

wherein each symbol has the same meaning as the above item (1') (hereinafter, referred to as G-7).

$R^4$ may be a group represented by Formula:

[Chemical formula 34]

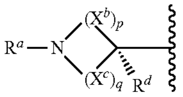
or
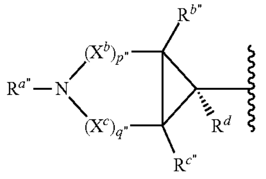

wherein $X^c$ is each independently $CH_2$, $R^{c''}$ is a hydrogen atom, and p, q, p'', q'', $R^a$, $R^{a''}$, $X^b$, $R^{b''}$, and $R^d$ have the same meaning as the above item (1') (hereinafter, referred to as G-8).

$R^4$ may be a group represented by Formula:

[Chemical formula 35]

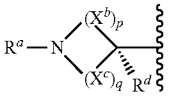

wherein $X^c$ is each independently $CH_2$, and p, q, $R^a$, $X^b$, and $R^d$ have the same meaning as the above item (1') (hereinafter, referred to as G-9).

$R^4$ may be a group represented by Formula:

[Chemical formula 36]

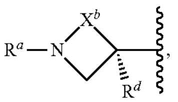
,
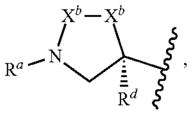
,
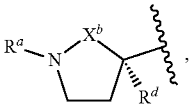
,
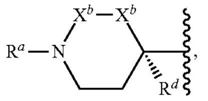
,
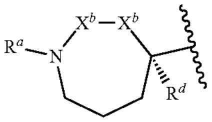
or
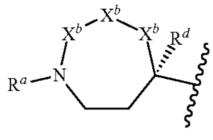

wherein each symbol has the same meaning as the above item (1') (hereinafter, referred to as G-10).

$R^4$ may be a group represented by Formula:

[Chemical formula 37]

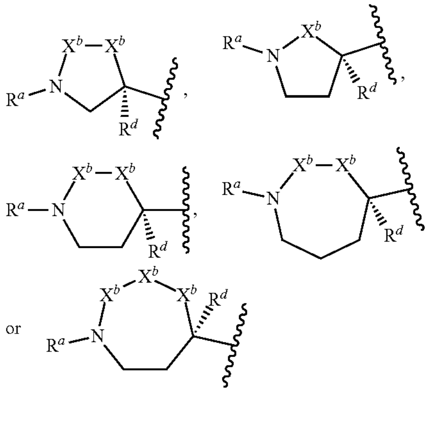

, , , or wherein each symbol has the same meaning as the above item (1') (hereinafter, referred to as G-11).

$R^4$ may be a group represented by Formula:

[Chemical formula 38]

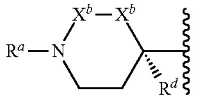

wherein each symbol has the same meaning as the above item (1') (hereinafter, referred to as G-12).

$R^4$ may be a group represented by Formula:

[Chemical formula 39]

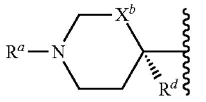

wherein $R^a$ is a hydrogen atom or unsubstituted alkyl;

$X^b$ is $CR^bR^{b\prime}$;

$R^b$ is a hydrogen atom or halogen;

$R^{b\prime}$ is a hydrogen atom or halogen;

$R^b$ and $R^{b\prime}$ may be taken together with the carbon atom to which they are bonded to form a substituted or unsubstituted non-aromatic carbocycle;

$R^d$ is a hydrogen atom (hereinafter, referred to as G-13).

$R^4$ may be a group represented by Formula:

[Chemical formula 40]

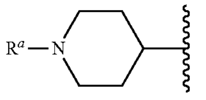

wherein $R^a$ is a hydrogen atom (hereinafter, referred to as G-14).

$R^4$ may be a group represented by Formula:

[Chemical formula 41]

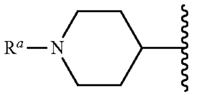

wherein $R^a$ is unsubstituted alkyl (hereinafter, referred to as G-15).

$R^4$ may be a group represented by Formula:

[Chemical formula 42]

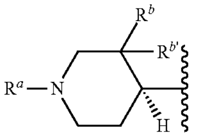

wherein $R^a$ is a hydrogen atom or unsubstituted alkyl; $R^b$ and $R^{b\prime}$ are each a hydrogen atom or a halogen (hereinafter, referred to as G-16).

$R^4$ may be a group represented by Formula:

[Chemical formula 43]

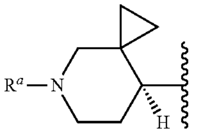

wherein $R^a$ is a hydrogen atom or unsubstituted alkyl (hereinafter, referred to as G-17).

p and q may be each independently 1, 2, or 3 (hereinafter, referred to as H-1).

p and q may be each independently 2 or 3 (hereinafter, referred to as H-2).

p may be 2, and q may be 1 (hereinafter, referred to as H-3).

p may be 2, and q may be 2 (hereinafter, referred to as H-4).

p may be 2, and q may be 3 (hereinafter, referred to as H-5).

p may be 1, 2, or 3 (hereinafter, referred to as H-6).

p may be 2 or 3 (hereinafter, referred to as H-7).

q may be 1, 2, or 3 (hereinafter, referred to as H-8).

q may be 2 or 3 (hereinafter, referred to as H-9).

p may be 1 (hereinafter, referred to as H-10).

p may be 2 (hereinafter, referred to as H-11).

p may be 3 (hereinafter, referred to as H-12).

q may be 1 (hereinafter, referred to as H-13).

q may be 2 (hereinafter, referred to as H-14).

q may be 3 (hereinafter, referred to as H-15).

p" and q" may be each independently 1 or 2 (hereinafter, referred to as J-1).

p" and q" may be each independently 1 (hereinafter, referred to as J-2).

$R^a$ may be a hydrogen atom, substituted or unsubstituted alkyl, substituted or unsubstituted alkenyl, substituted or unsubstituted alkynyl, substituted or unsubstituted non-aromatic carbocyclyl, or substituted or unsubstituted non-aromatic heterocyclyl (hereinafter, referred to as K-1).

$R^a$ may be a hydrogen atom, substituted or unsubstituted alkyl, substituted or unsubstituted alkenyl, or substituted or unsubstituted alkynyl (hereinafter, referred to as K-2).

$R^a$ may be a hydrogen atom or substituted or unsubstituted alkyl (hereinafter, referred to as K-3).

$R^a$ may be a hydrogen atom, alkyl substituted with halogen, or unsubstituted alkyl (hereinafter, referred to as K-4).

$R^a$ may be a hydrogen atom or unsubstituted alkyl (hereinafter, referred to as K-5).

$R^a$ may be a hydrogen atom (hereinafter, referred to as K-6).

$R^a$ may be substituted or unsubstituted alkyl (hereinafter, referred to as K-7).

$R^a$ may be unsubstituted alkyl (hereinafter, referred to as K-8).

$R^{a''}$ may be a hydrogen atom, substituted or unsubstituted alkyl, substituted or unsubstituted alkenyl, substituted or unsubstituted alkynyl, substituted or unsubstituted non-aromatic carbocyclyl, or substituted or unsubstituted non-aromatic heterocyclyl (hereinafter, referred to as L-1).

$R^{a''}$ may be a hydrogen atom, substituted or unsubstituted alkyl, substituted or unsubstituted alkenyl, or substituted or unsubstituted alkynyl (hereinafter, referred to as L-2).

$R^{a''}$ may be a hydrogen atom or substituted or unsubstituted alkyl (hereinafter, referred to as L-3).

$R^{a''}$ may be a hydrogen atom (hereinafter, referred to as L-4).

$R^{a''}$ may be substituted or unsubstituted alkyl (hereinafter, referred to as L-5).

$X^b$ may be each independently $CR^bR^{b'}$ (hereinafter, referred to as M-1).

$X^c$ may be each independently $CR^cR^{c'}$ (hereinafter, referred to as M-2).

$R^b$ may be each independently a hydrogen atom, halogen, substituted or unsubstituted alkyl, or substituted or unsubstituted alkyloxy (hereinafter, referred to as N-1).

$R^b$ may be each independently a hydrogen atom or halogen (hereinafter, referred to as N-2).

$R^b$ may be each independently a hydrogen atom (hereinafter, referred to as N-3).

$R^b$ may be each independently halogen (hereinafter, referred to as N-4).

$R^{b'}$ may be each independently a hydrogen atom, halogen, substituted or unsubstituted alkyl, or substituted or unsubstituted alkyloxy (hereinafter, referred to as N-5).

$R^{b'}$ may be each independently a hydrogen atom or halogen (hereinafter, referred to as N-6).

$R^{b'}$ may be each independently a hydrogen atom (hereinafter, referred to as N-7).

$R^c$ may be each independently a hydrogen atom, halogen, substituted or unsubstituted alkyl, or substituted or unsubstituted alkyloxy (hereinafter, referred to as O-1).

$R^c$ may be each independently a hydrogen atom or halogen (hereinafter, referred to as O-2).

$R^c$ may be each independently a hydrogen atom (hereinafter, referred to as O-3).

$R^c$ may be each independently halogen (hereinafter, referred to as O-4).

$R^{c'}$ may be each independently a hydrogen atom, halogen, substituted or unsubstituted alkyl, or substituted or unsubstituted alkyloxy (hereinafter, referred to as O-5).

$R^{c'}$ may be each independently a hydrogen atom or halogen (hereinafter, referred to as O-6).

$R^{c'}$ may be each independently a hydrogen atom (hereinafter, referred to as O-7).

$R^{b''}$ may be a hydrogen atom, halogen, substituted or unsubstituted alkyl, or substituted or unsubstituted alkyloxy (hereinafter, referred to as P-1).

$R^{b''}$ may be a hydrogen atom or halogen (hereinafter, referred to as P-2).

$R^{c''}$ may be a hydrogen atom, halogen, substituted or unsubstituted alkyl, or substituted or unsubstituted alkyloxy (hereinafter, referred to as Q-1).

$R^{c''}$ may be a hydrogen atom or halogen (hereinafter, referred to as Q-2).

$X^d$ may be $CR^d$ or N (hereinafter, referred to as R-1).

$X^d$ may be $CR^d$ (hereinafter, referred to as R-2).

$X^{d''}$ may be $CR^d$ or N (hereinafter, referred to as S-1).

$X^{d''}$ may be $CR^d$ (hereinafter, referred to as S-2).

$R^d$ may be a hydrogen atom, halogen, cyano, substituted or unsubstituted alkyl, or substituted or unsubstituted carbamoyl (hereinafter, referred to as T-1).

$R^d$ may be a hydrogen atom or substituted or unsubstituted alkyl (hereinafter, referred to as T-2).

$R^d$ may be a hydrogen atom (hereinafter, referred to as T-3).

$R^b$ and $R^{b'}$ and $R^c$ and $R^{c'}$ are taken together with the same carbon atom to which they are bonded to form a substituted or unsubstituted non-aromatic carbocycle or a substituted or unsubstituted non-aromatic heterocycle (hereinafter, referred to as U-1).

$R^b$ and $R^{b'}$ and $R^c$ and $R^{c'}$ are taken together with the same carbon atom to which they are bonded to form a substituted or unsubstituted non-aromatic carbocycle (hereinafter, referred to as U-2).

$R^a$, and $R^b$ bonded to a carbon atom adjacent to a nitrogen atom to which $R^a$ is bonded are taken together with the nitrogen atom to which $R^a$ is bonded and the carbon atom to which $R^b$ is bonded to form a substituted or unsubstituted non-aromatic heterocycle (hereinafter, referred to as U-3).

$R^a$, and $R^c$ bonded to a carbon atom adjacent to a nitrogen atom to which $R^a$ is bonded are taken together with the nitrogen atom to which $R^a$ is bonded and the carbon atom to which $R^c$ is bonded to form a substituted or unsubstituted non-aromatic heterocycle (hereinafter, referred to as U-4).

$R^b$ and $R^c$ may be taken together to form a (C1-C3) bridge, wherein one of the carbon atoms constituting the bridge may be replaced with an oxygen atom (hereinafter, referred to as U-5).

$R^b$ and $R^c$ are taken together to form a (C1-C3) bridge (hereinafter, referred to as U-6).

$R^b$ and $R^c$ are taken together to form a (C2-C3) bridge (hereinafter, referred to as U-7).

$R^a$ and $R^d$ may be taken together to form a (C1-C3) bridge, wherein one of the carbon atoms constituting the bridge may be replaced with an oxygen atom (hereinafter, referred to as U-8).

$R^a$ and $R^d$ are taken together to form a (C1-C3) bridge (hereinafter, referred to as U-9).

$R^a$ and $R^d$ are taken together to form a (C2-C3) bridge (hereinafter, referred to as U-10).

$R^5$ and $R^6$ may be each independently a hydrogen atom, halogen, hydroxy, substituted or unsubstituted alkyl, or substituted or unsubstituted alkyloxy (hereinafter, referred to as V-1).

$R^5$ and $R^6$ may be each independently a hydrogen atom, or substituted or unsubstituted alkyl (hereinafter, referred to as V-2).

$R^5$ and $R^6$ may be each independently a hydrogen atom (hereinafter, referred to as V-3).

$R^7$ may be a group represented by Formula:

[Chemical formula 44]

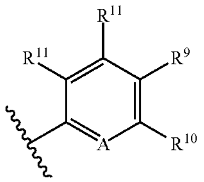

wherein $R^9$ is substituted or unsubstituted alkyloxy, substituted or unsubstituted amino, substituted or unsubstituted aromatic carbocyclyloxy, substituted or unsubstituted alkyl, a substituted or unsubstituted non-aromatic carbocycle, or cyano; $R^{10}$ is a hydrogen atom, halogen, hydroxy, substituted or unsubstituted alkyl, or substituted or unsubstituted alkyloxy; or $R^9$ and $R^{10}$ may be taken together to form a substituted or unsubstituted non-aromatic carbocycle or a substituted or unsubstituted non-aromatic heterocycle; A and $R^{11}$ have the same meaning as the above item (1') (hereinafter, referred to as W-1).

$R^7$ may be a group represented by Formula:

[Chemical formula 45]

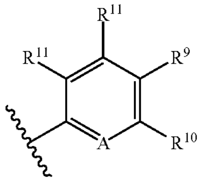

wherein $R^9$ is substituted or unsubstituted alkyloxy, substituted or unsubstituted amino, substituted or unsubstituted aromatic carbocyclyloxy, substituted or unsubstituted alkyl, a substituted or unsubstituted non-aromatic carbocycle, or cyano; $R^{10}$ is a hydrogen atom, halogen, hydroxy, substituted or unsubstituted alkyl, or substituted or unsubstituted alkyloxy; A and $R^{11}$ have the same meaning as the above item (1') (hereinafter, referred to as W-2).

$R^7$ may be a group represented by Formula:

[Chemical formula 46]

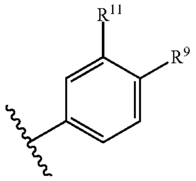

wherein $R^9$ is substituted or unsubstituted alkyloxy, substituted or unsubstituted amino, substituted or unsubstituted aromatic carbocyclyloxy, substituted or unsubstituted alkyl, a substituted or unsubstituted non-aromatic carbocycle, or cyano; $R^{11}$ is a hydrogen atom or halogen (hereinafter, referred to as W-3).

$R^7$ may be a group represented by Formula:

[Chemical formula 47]

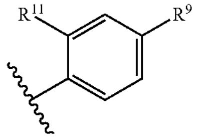

wherein $R^9$ is substituted or unsubstituted alkyloxy, substituted or unsubstituted amino, substituted or unsubstituted aromatic carbocyclyloxy, substituted or unsubstituted alkyl, a substituted or unsubstituted non-aromatic carbocycle, or cyano; $R^{11}$ is a hydrogen atom or halogen (hereinafter, referred to as W-4).

$R^7$ may be a group represented by Formula:

[Chemical formula 48]

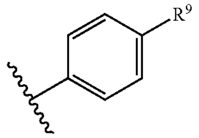

wherein $R^9$ has the same meaning as the above item (1') (hereinafter, referred to as W-5).

A may be $CR^{11}$ or N (hereinafter, referred to as X-1).

A may be $CR^{11}$ (hereinafter, referred to as X-2).

A may be CH (hereinafter, referred to as X-3).

$R^9$ may be substituted or unsubstituted alkyloxy, substituted or unsubstituted amino, substituted or unsubstituted aromatic carbocyclyloxy, substituted or unsubstituted alkyl, a substituted or unsubstituted non-aromatic carbocycle, or cyano (hereinafter, referred to as Y-1).

$R^9$ may be substituted or unsubstituted alkyloxy, substituted or unsubstituted amino, substituted or unsubstituted aromatic carbocyclyloxy, substituted or unsubstituted alkyl, or a substituted or unsubstituted non-aromatic carbocycle (hereinafter, referred to as Y-2).

$R^9$ may be substituted or unsubstituted alkyloxy, substituted or unsubstituted amino, substituted or unsubstituted aromatic carbocyclyloxy, or substituted or unsubstituted alkyl (hereinafter, referred to as Y-3).

$R^9$ may be substituted or unsubstituted alkyloxy, substituted or unsubstituted amino, or substituted or unsubstituted alkyl (hereinafter, referred to as Y-4).

$R^9$ may be substituted alkyloxy (substituent: halogen), unsubstituted alkyloxy, substituted amino (substituent: alkyl), substituted alkyl (substituent: halogen), or unsubstituted alkyl (hereinafter, referred to as Y-5).

$R^9$ may be substituted or unsubstituted alkyloxy (hereinafter, referred to as Y-6).

$R^9$ may be alkyloxy substituted with halogen, or unsubstituted alkyloxy (hereinafter, referred to as Y-7).

$R^9$ may be unsubstituted alkyloxy (hereinafter, referred to as Y-8).

$R^9$ may be alkyloxy substituted with halogen (hereinafter, referred to as Y-9).

$R^9$ may be substituted or unsubstituted amino (hereinafter, referred to as Y-10).

$R^9$ may be amino substituted with alkyl (hereinafter, referred to as Y-11).

$R^9$ may be substituted or unsubstituted alkyl (hereinafter, referred to as Y-12).

$R^9$ may be alky substituted with halogen, or unsubstituted alkyl (hereinafter, referred to as Y-13).

$R^9$ may be unsubstituted alkyl (hereinafter, referred to as Y-14).

$R^9$ may be alkyl substituted with halogen (hereinafter, referred to as Y-15).

$R^{10}$ may be a hydrogen atom, halogen, hydroxy, substituted or unsubstituted alkyl, or substituted or unsubstituted alkyloxy (hereinafter, referred to as Y-16).

$R^{10}$ may be a hydrogen atom, halogen, or substituted or unsubstituted alkyl (hereinafter, referred to as Y-17).

$R^{10}$ may be a hydrogen atom or halogen (hereinafter, referred to as Y-18).

$R^{10}$ may be a hydrogen atom (hereinafter, referred to as Y-19).

$R^9$ and $R^{10}$ may be taken together to form a substituted or unsubstituted non-aromatic carbocycle or a substituted or unsubstituted non-aromatic heterocycle (hereinafter, referred to as Y-20).

$R^9$ and $R^{10}$ may be taken together to form a substituted or unsubstituted non-aromatic carbocycle (hereinafter, referred to as Y-21).

$R^9$ and $R^{10}$ may be taken together to form a substituted or unsubstituted non-aromatic heterocycle (hereinafter, referred to as Y-22).

$R^{11}$ may be each independently a hydrogen atom, halogen, hydroxy, substituted or unsubstituted alkyl, or substituted or unsubstituted alkyloxy (hereinafter, referred to as Y-23).

$R^{11}$ may be each independently a hydrogen atom, halogen, or substituted or unsubstituted alkyl (hereinafter, referred to as Y-24).

$R^{11}$ may be each independently a hydrogen atom or halogen (hereinafter, referred to as Y-25).

$R^{11}$ may be each independently a hydrogen atom (hereinafter, referred to as Y-26).

In the compound represented by Formula (I), for example, the following embodiments are more preferable. Embodiments of all combinations of specific examples shown below are mentioned as examples.

(I) A compound represented by Formula (I'):

[Chemical formula 49]

(I')

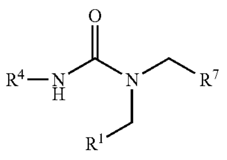

or a pharmaceutically acceptable salt thereof.

In the formula, $R^1$ may be the above (A-4), (A-5), (A-6), (A-7), (A-8), (A-9), (A-10), (A-11), (A-12), (A-13), (A-14), (A-15), (A-16), (A-17), (A-18), (A-19), (A-20), (A-21), (A-22), (A-23), (A-24), (A-25), (A-26), (A-27), (A-28), (A-29), (A-30), (A-31), (A-32), (A-33), (A-34), or (A-35).

$R^4$ may be the above (G-12), (G-13), (G-14), (G-15), (G-16), or (G-17).

$R^7$ may be a group represented by Formula:

[Chemical formula 50]

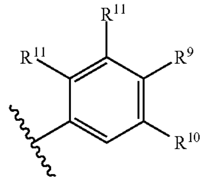

In the formula, $R^9$ may be the above (Y-4), (Y-5), (Y-6), (Y-7), (Y-8), (Y-9), (Y-10), (Y-11), (Y-12), (Y-13), (Y-14), or (Y-15).

$R^{10}$ may be the above (Y-17), (Y-18), or (Y-19).

$R^{11}$ may be each independently the above (Y-24), (Y-25), or (Y-26).

(ii) A compound represented b Formula (II'):

[Chemical formula 51]

(II')

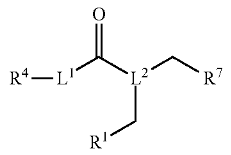

or a pharmaceutically acceptable salt thereof.

In the formula, a combination of ($L^1$, $L^2$) may be the above (E-12), (E-14), or (E-15).

$R^1$ may be the above (A-6), (A-12), (A-13), (A-14), (A-15), (A-16), (A-23), (A-24), (A-25), (A-26), (A-27), (A-28), (A-29), (A-30), (A-31), (A-32), (A-33), (A-34), or (A-35).

$R^4$ may be the above (G-13), (G-14), (G-15), (G-16), or (G-17).

$R^7$ may be a group represented by Formula:

[Chemical formula 52]

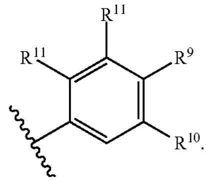

In the formula, $R^9$ may be the above (Y-6), (Y-7), (Y-8), (Y-9), (Y-12), (Y-13), (Y-14), or (Y-15).

$R^{10}$ may be the above (Y-18) or (Y-19).

$R^{11}$ may be each independently the above (Y-25) or (Y-26).

In particular, the following embodiments are preferable.

(i) A compound represented by Formula (II'):

[Chemical formula 53]

(II')

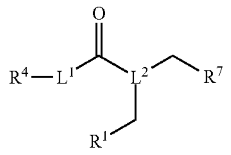

wherein $R^1$ is substituted or unsubstituted 5-membered aromatic heterocyclyl;

a combination of ($L^1$, $L^2$) is (NH, N) or ($CH_2$, N);

$R^4$ is a group represented by Formula:

[Chemical formula 54]

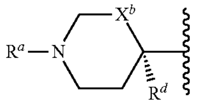

wherein $R^a$ is a hydrogen atom or unsubstituted alkyl;

$X^b$ is $CR^bR^{b'}$;

$R^b$ is a hydrogen atom or halogen;

$R^{b'}$ is a hydrogen atom or halogen;

$R^b$ and $R^{b'}$ may be taken together with the carbon atom to which they are bonded to form a substituted or unsubstituted non-aromatic carbocycle;

$R^d$ is a hydrogen atom;

$R^7$ is a group represented by Formula:

[Chemical formula 55]

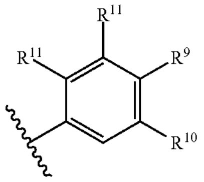

wherein $R^9$ is substituted or unsubstituted alkyloxy, or substituted or unsubstituted alkyl;

$R^{10}$ is a hydrogen atom or halogen;

$R^{11}$ is each independently a hydrogen atom or halogen, hydroxy, substituted or unsubstituted alkyl, or substituted or unsubstituted alkyloxy;

or a pharmaceutically acceptable salt thereof.

(ii) A compound represented by Formula (II'):

[Chemical formula 56]

(II')

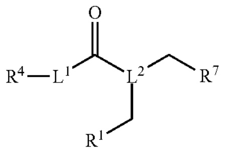

wherein $R^1$ is substituted or unsubstituted oxazolyl, substituted or unsubstituted triazolyl, or substituted or unsubstituted pyrazolyl;

a combination of ($L^1$, $L^2$) is (NH, N) or ($CH_2$, N);

$R^4$ is a group represented by Formula:

[Chemical formula 57]

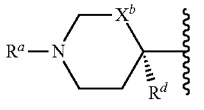

wherein $R^a$ is a hydrogen atom or unsubstituted alkyl;

$X^b$ is $CR^bR^{b'}$;

$R^b$ is a hydrogen atom or halogen;

$R^{b'}$ is a hydrogen atom or halogen;

$R^b$ and $R^{b'}$ may be taken together with the carbon atom to which they are bonded to form a substituted or unsubstituted non-aromatic carbocycle;

$R^d$ is a hydrogen atom;

$R^7$ is a group represented by Formula:

[Chemical formula 58]

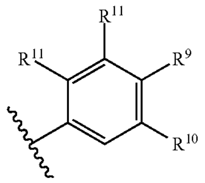

wherein $R^9$ is substituted or unsubstituted alkyloxy, or substituted or unsubstituted alkyl;

$R^{10}$ is a hydrogen atom or halogen;

$R^{11}$ is each independently a hydrogen atom or halogen;

or a pharmaceutically acceptable salt thereof.

(iii) A compound represented by Formula (II'):

[Chemical formula 59]

(II')

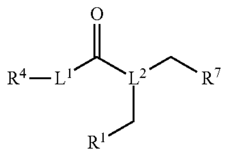

$R^1$ is oxazolyl substituted with substituent group ω", triazolyl substituted with substituent group ω", or pyrazolyl substituted with substituent group ω"(substituent group ω": haloalkyl, unsubstituted alkyl, and non-aromatic carbocyclyl);

a combination of ($L^1$, $L^2$) is (NH, N) or ($CH_2$, N);

$R^4$ is a group represented by Formula:

[Chemical formula 60]

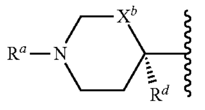

wherein $R^a$ is a hydrogen atom or unsubstituted alkyl;

$X^b$ is $CR^bR^{b'}$;

$R^b$ is a hydrogen atom or a fluorine atom;

$R^{b'}$ is a hydrogen atom or a fluorine atom;

$R^b$ and $R^{b'}$ may be taken together with the carbon atom to which they are bonded to form an unsubstituted cyclopropane ring;

$R^d$ is a hydrogen atom;

$R^7$ is a group represented by Formula:

[Chemical formula 61]

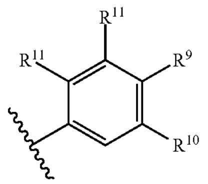

wherein $R^9$ is alkyloxy substituted with halogen, unsubstituted alkyloxy, haloalkyl, or unsubstituted alkyl;

$R^{10}$ is a hydrogen atom or halogen;

$R^{11}$ is each independently a hydrogen atom or halogen;

or a pharmaceutically acceptable salt thereof.

The compounds represented by Formula (I), Formula (I'), or Formula (II') are not limited to specific isomers, but include all possible isomers (e.g., keto-enol isomers, imine-enamine isomers, diastereoisomers, optical isomers, rotational isomers, etc.), racemates, or mixtures thereof.

One or more hydrogen, carbon, and/or other atom(s) of the compounds represented by Formula (I), Formula (I'), or Formula (II') may be substituted with isotope(s) of hydrogen, carbon, and/or other atom(s), respectively. Examples of such isotopes include hydrogen, carbon, nitrogen, oxygen, phosphorus, sulfur, fluorine, iodine, and chlorine, as in the cases of $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$, and $^{36}Cl$, respectively. The compounds represented by Formula (I), Formula (I'), or Formula (II') also include compounds substituted with such isotopes. The compounds substituted with the isotopes are also useful as pharmaceutical products and include all radiolabeled forms of the compounds represented by Formula (I), Formula (I'), or Formula (II'). Furthermore, a "radiolabeling method" for producing the "radiolabeled forms" is also included in the present invention, and the "radiolabeled forms" are useful as tools for metabolic pharmacokinetics studies, studies on binding assay, and/or diagnostics.

Radiolabeled forms of the compounds represented by Formula (I), Formula (I'), or Formula (II') can be prepared by methods well known in the pertinent art. For example, a tritium-labeled compound represented by Formula (I), Formula (I'), or Formula (II') can be prepared by introducing tritium into a specific compound represented by Formula (I), Formula (I'), or Formula (II'), by a catalytic dehalogenation reaction using tritium. This method comprises reacting an appropriately-halogenated precursor of the compound of Formula (I), Formula (I'), or Formula (II') with tritium gas in the presence of an appropriate catalyst, such as Pd/C, and in the presence or absence of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$ carbon.

The pharmaceutically acceptable salts of the compounds represented by Formula (I), Formula (I'), or Formula (II') include, for example, salts of compounds represented by Formula (I), Formula (I'), or Formula (II') with alkaline metal (e.g., lithium, sodium, or potassium), alkaline earth metal (e.g., calcium or barium), magnesium, transition metal (e.g., zinc or iron), ammonia, organic bases (e.g., trimethylamine, triethylamine, dicyclohexylamine, ethanolamine, diethanolamine, triethanolamine, meglumine, ethylenediamine, pyridine, picoline, or quinoline), or amino acids, or salts with inorganic acids (e.g., hydrochloric acid, sulfuric acid, nitric acid, carbonic acid, hydrobromic acid, phosphoric acid, or hydroiodic acid) or organic acids (e.g., formic acid, acetic acid, propionic acid, trifluoroacetic acid, citric acid, lactic acid, tartaric acid, oxalic acid, maleic acid, fumaric acid, succinic acid, mandelic acid, glutaric acid, malic acid, benzoic acid, phthalic acid, ascorbic acid, benzenesulfonic acid, p-toluenesulfonic acid, methanesulfonic acid, ethanesulfonic acid, or trifluoroacetic acid). These salts can be formed by the usual methods.

The compounds represented by Formula (I), Formula (I'), or Formula (II') of the present invention or pharmaceutically acceptable salts thereof may form solvates (e.g., hydrates), co-crystals, and/or crystal polymorphs. The present invention encompasses those various solvates, co-crystals, and crystal polymorphs. The "solvates" may have the compounds represented by Formula (I), Formula (I'), or Formula (II') coordinated with any number of solvent molecules (e.g., water molecules). When the compounds represented by Formula (I), Formula (I'), or Formula (II'), or pharmaceutically acceptable salts thereof are allowed to stand in the atmosphere, the compounds may absorb water, resulting in attachment of adsorbed water or formation of hydrates. Recrystallization of the compounds represented by Formula (I), Formula (I'), or Formula (II'), or pharmaceutically acceptable salts thereof may produce crystal polymorphs. The "co-crystal" means that a compound represented by Formula (I), Formula (I'), or Formula (II'), or a salt thereof and a counter molecule exist in the same crystal lattice, and it can include any number of counter molecules.

The compounds represented by Formula (I), Formula (I'), or Formula (II') of the present invention or pharmaceutically acceptable salts thereof may form prodrugs. The present invention also encompasses such various prodrugs. Prodrugs are derivatives of the compounds according to the present invention that have chemically or metabolically degradable groups, and compounds that are converted to the pharmaceutically active compounds according to the present invention through solvolysis or under physiological conditions in vivo. Prodrugs include compounds that are converted to the compounds represented by Formula (I), Formula (I'), or Formula (II') through enzymatic oxidation, reduction, hydrolysis, or the like under physiological conditions in vivo, compounds that are converted to the compounds represented by Formula (I), Formula (I'), or Formula (II') through hydrolysis by gastric acid etc., and the like. Methods for selecting and preparing suitable prodrug derivatives are described in, for example, "Design of Prodrugs, Elsevier, Amsterdam, 1985". Prodrugs themselves may have some activity.

When the compounds represented by Formula (I), Formula (I'), or Formula (II') or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride, and mixed anhydride, or with a condensing agent. For example, they include $CH_3COO$—, $C_2H_5COO$—, tert-BuCOO—, $C_{15}H_{31}COO$—, PhCOO—, (m-NaOOCPh)COO—, $NaOOCCH_2CH_2COO$—, $CH_3CH(NH_2)COO$—, $CH_2N(CH_3)_2COO$—, $CH_3SO_3$—, $CH_3CH_2SO_3$—, $CF_3SO_3$—, $CH_2FSO_3$—, $CF_3CH_2SO_3$—, p-$CH_3O$-$PhSO_3$—, $PhSO_3$—, and p-$CH_3PhSO_3$—.

Since the compound according to the present invention has serotonin 5-HT2A receptor antagonism and/or inverse agonism, the compound is useful as a therapeutic and/or prophylactic agent for a disease related to a serotonin 5-HT2A receptor. Diseases related to a serotonin 5-HT2A receptor include serotonin-mediated diseases such as Parkinson's disease-related hallucinations and delusions, dementia-related hallucinations and delusions, schizophrenia-related hallucinations and delusions, depression-related hallucinations and delusions, neurodegenerative diseases-related hallucinations and delusions, depression, schizophrenia, autism, dependence, dyskinesia, sleep disorder, Parkinson's disease-related irritability, dementia-related irritability, schizophrenia-related irritability, and sexual dysfunction. Preferable examples include Parkinson's disease-related hallucinations and delusions, dementia-related hallucinations and delusions, schizophrenia-related hallucinations and delusions, depression-related hallucinations and delusions, Parkinson's disease-related irritability, dementia-related irritability, and schizophrenia-related irritability. More preferable examples include Parkinson's disease-related hallucinations and delusions, and dementia-related hallucinations and delusions.

The "serotonin 5-HT2A receptor antagonist and/or inverse agonist" means a pharmaceutical product having serotonin 5-HT2A receptor antagonism and/or inverse agonism.

The "composition for serotonin 5-HT2A receptor antagonism and/or inverse agonism" means a composition having serotonin 5-HT2A receptor antagonism and/or inverse agonism, and it is not limited to pharmaceutical use.

(Method for Producing Compounds of the Present Invention)

The compounds represented by Formula (I), Formula (I'), or Formula (II') according to the present invention can be produced by, for example, the general synthesis method described below. Regarding extraction, purification, and the like, the treatments carried out in ordinary experiments of organic chemistry may be carried out.

The compounds of the present invention can be synthesized with reference to methods known in the art.

Method 4

[Chemical formula 62]

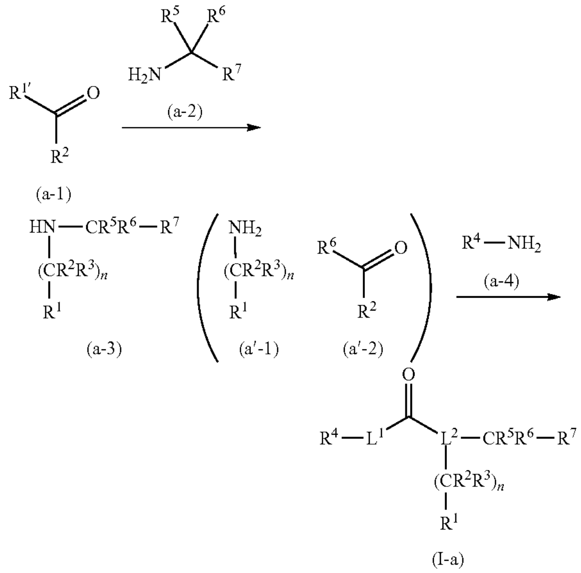
(a-1) (a-2) (a-3) (a'-1) (a'-2) (a-4) (I-a)

-continued

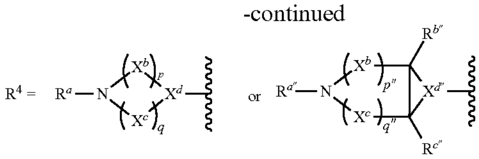

wherein each symbol has the same meaning as the above item (1'), and $R^{1'}$— is $R^1$— or $R^1$—$(CR^2R^3)_{n-1}$—.

Step 1

Compound (a-3) can be obtained by reacting compound (a-1) and compound (a-2) with an appropriate reducing agent in an appropriate solvent in the presence or absence of acetic acid. Alternatively, compound (a-3) can also be obtained in the same manner by using compound (a'-1) and compound (a'-2) in place of compound (a-1) and compound (a-2).

Examples of the reducing agent include sodium borohydride, sodium triacetoxyborohydride, and sodium cyanoborohydride, and the reducing agent can be used in an amount of 1.0 molar equivalents or more, preferably 1.0 to 2.0 molar equivalents relative to compound (a-1).

Acetic acid can be used in an amount of 1.0 molar equivalents or more, preferably 1.0 to 2.0 molar equivalents relative to compound (a-1).

Reaction solvents include alcohols (e.g., methanol, ethanol, tert-butanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane, etc.), halogenated hydrocarbons (e.g., chloroform, dichloromethane, etc.), DMF, DMSO, NMP, acetonitrile, and pyridine, and each solvent can be used alone or mixed with the others.

The reaction temperature is 0 to 80° C., preferably 0 to 20° C.

The reaction time is 0.1 to 48 hours, preferably 0.5 to 24 hours.

The obtained desired compound (a-3) can be purified by a conventional method (e.g., column chromatography, recrystallization, etc.) if necessary.

Step 2

Compound (I-a) can be obtained by reacting compound (a-4) and CDI in an appropriate solvent, and then reacting with compound (a-3) in an appropriate solvent.

CDI can be used in an amount of 1.0 molar equivalents or more, preferably 1.2 molar equivalents relative to compound (a-4).

Reaction solvents include alcohols (e.g., methanol, ethanol, tert-butanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane, etc.), halogenated hydrocarbons (e.g., chloroform, dichloromethane, etc.), DMF, DMSO, NMP, acetonitrile, and pyridine, and each solvent can be used alone or mixed with the others.

The reaction temperature is 0 to 80° C., preferably 0 to 20° C.

The reaction time is 0.1 to 24 hours, preferably 0.5 to 6 hours.

The obtained desired compound (I-a) can be purified by a conventional method (e.g., column chromatography, recrystallization, etc.) if necessary.

Method A'

[Chemical formula 63]

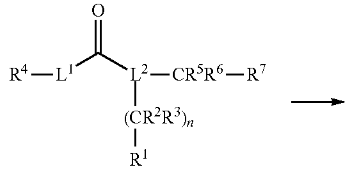

(I-a')

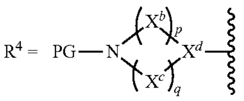

or

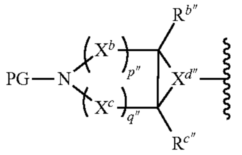

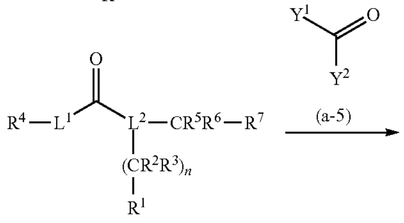

(I-a'')

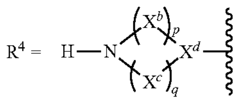

or

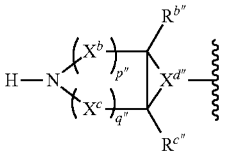

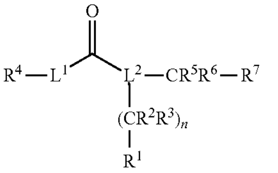

(I-a''')

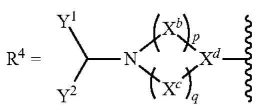

or

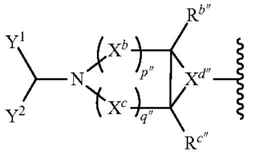

wherein each symbol has the same meaning as the above item (1'); PG is a suitable protecting group ωof an amino group (e.g., Boc, Cbz, etc.); $Y^1$ and $Y^2$ may be a hydrogen atom, substituted or unsubstituted alkyl, or substituted or unsubstituted alkyloxy, or the like.

Step 1

Compound (I-a") can be obtained by deprotecting PG in the presence of an acid in the absence of a solvent or in an appropriate solvent, or by reacting compound (I-a') with hydrogen gas in the presence of a metal catalyst in the absence of a solvent or in an appropriate solvent to deprotect PG.

Examples of the acid include hydrochloric acid, sulfuric acid, TFA, and formic acid, and the acid can be used in an amount of 1.0 molar equivalents or more, preferably 1.0 to 30 molar equivalents relative to compound (I-a').

Examples of the metal catalyst include palladium-carbon (Pd/C), Adams' catalyst ($PtO_2$), Pearlman's catalyst ($Pd(OH)_2$), rhodium-aluminum oxide, and chlorotris(triphenylphosphine)rhodium(I), and the metal catalyst can be used at 0.01 to 100 weight percent relative to compound (I-a').

The hydrogen pressure can be 1 to 50 atm. As the hydrogen source, cyclohexene, 1,4-cyclohexadiene, formic acid, ammonium formate, or the like can also be used.

Reaction solvents include alcohols (e.g., methanol, ethanol, tert-butanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane, etc.), halogenated hydrocarbons (e.g., chloroform, dichloromethane, etc.), DMF, DMSO, NMP, acetonitrile, and pyridine, and each solvent can be used alone or mixed with the others.

The reaction temperature is 0 to 80° C., preferably 0 to 20° C.

The reaction time is 0.1 to 24 hours, preferably 0.5 to 6 hours.

The obtained desired compound (I-a") can be purified by a conventional method (e.g., column chromatography, recrystallization, etc.) if necessary.

Step 2

Compound (I-a'") can be obtained by reacting compound (I-a") and compound (a-5) with an appropriate reducing agent and, if necessary, acetic acid in an appropriate solvent.

Examples of the reducing agent include sodium triacetoxyborohydride and sodium cyanoborohydride, and the reducing agent can be used in an amount of 1.0 molar equivalents or more, preferably 1.0 to 2.0 molar equivalents relative to compound (I-a").

Acetic acid can be used in an amount of 1.0 molar equivalents or more, preferably 1.0 to 2.0 molar equivalents relative to compound (I-a").

Reaction solvents include alcohols (e.g., methanol, ethanol, tert-butanol, isopropanol, etc.), aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, dimethoxyethane, etc.), halogenated hydrocarbons (e.g., chloroform, dichloromethane, etc.), DMF, DMSO, NMP, acetonitrile, and pyridine, and each solvent can be used alone or mixed with the others.

The reaction temperature is 0 to 80° C., preferably 0 to 20° C.

The reaction time is 0.1 to 24 hours, preferably 0.5 to 6 hours.

The obtained desired compound (I-a'") can be purified by a conventional method (e.g., column chromatography, recrystallization, etc.) if necessary.

Method B

[Chemical formula 64]

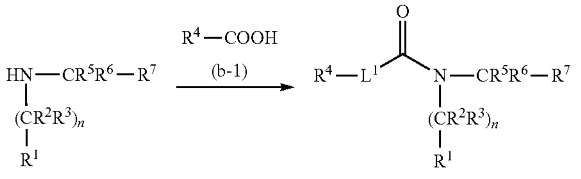

(a-3) (b-1) (I-b)

wherein each symbol has the same meaning as the above item (1').

Compound (I-b) can be obtained by reacting compound (a-3) with compound (b-1) in the presence of a condensing agent.

Examples of the condensing agent include dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU, and the condensing agent can be used in an amount of 1 to 5 molar equivalents relative to compound (a-3).

The reaction temperature is −20° C. to 60° C., preferably 0° C. to 30° C.

The reaction time is 0.1 hours to 24 hours, and preferably 1 hour to 12 hours.

Reaction solvents include DMF, DMA, NMP, tetrahydrofuran, dioxane, dichloromethane, and acetonitrile, and each solvent can be used alone or mixed with the others.

The obtained desired compound (I-b) can be purified by a conventional method (e.g., column chromatography, recrystallization, etc.) if necessary.

Method C

[Chemical formula 65]

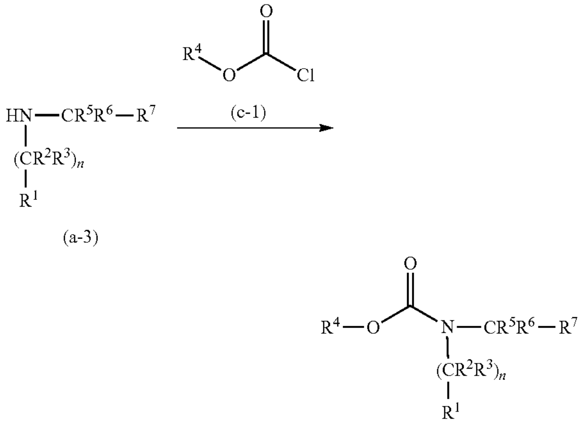

(a-3) (c-1) (I-c)

wherein each symbol has the same meaning as the above item (1').

Compound (I-c) can be obtained by reacting compound (a-3) with compound (c-1) or a salt thereof in the presence of a base.

Examples of the base include pyridine, 2,6-lutidine, triethylamine, and NMM, and the base can be used in an amount of 2 to 10 molar equivalents relative to compound (a-3).

The reaction temperature is −20° C. to 60° C., preferably 0° C. to 30° C.

The reaction time is 0.1 hours to 24 hours, and preferably 1 hour to 12 hours.

Reaction solvents include dichloromethane, DMF, DMA, NMP, tetrahydrofuran, dioxane, and acetonitrile, and each solvent can be used alone or mixed with the others.

The obtained desired compound (I-c) can be purified by a conventional method (e.g., column chromatography, recrystallization, etc.) if necessary.

Since the compound according to the present invention has serotonin 5-HT2A receptor antagonism and/or inverse agonism, the compound is useful as a therapeutic and/or prophylactic agent for Parkinson's disease- and/or dementia-related hallucinations and delusions.

Furthermore, the compound according to the present invention has utility as a pharmaceutical, and preferably, the compound has any one or a plurality of the following excellent features.

a) Inhibitory activity against CYP enzymes (for example, CYP1A2, CYP2C9, CYP2C19, CYP2D6, and CYP3A4) is weak.
b) Satisfactory pharmacokinetics such as high bioavailability and adequate clearance are exhibited.
c) Metabolic stability is high.
d) Irreversible inhibitory activity is not exhibited against CYP enzymes (for example, CYP3A4) within the concentration range of the measurement conditions described in the present description.
e) Mutagenicity is not exhibited.
f) The cardiovascular risk is low.
g) High solubility is exhibited.
h) High binding ability for a serotonin 5-HT2A receptor is exhibited.
i) High binding ability for a serotonin 5-HT2C receptor is exhibited.
j) Brain distribution ability is high.
k) P-gp substrate property is low.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear, or vaginal administration.

In the case of oral administration, any dosage forms, which are usually used, such as oral solid preparations (e.g., tablets, powders, granules, capsules, pills, or films), and oral liquid preparations (e.g., suspensions, emulsions, elixirs, syrups, lemonades, spirits, aromatic water, extracts, decoctions, or tinctures) may be prepared according to a conventional method and administered. The tablets may be sugar-coated tablets, film-coated tablets, enteric-coated tablets, sustained-release tablets, troche tablets, sublingual tablets, buccal tablets, chewable tablets, or orally disintegrating tablets. The powders and the granules may be dry syrups. The capsules may be soft capsules, microcapsules, or sustained-release capsules.

In the case of parenteral administration, any dosage forms, which are usually used, such as injections, drips, and external preparations (e.g., ophthalmic drops, nasal drops, ear drops, aerosols, inhalations, lotions, infusions, liniments, mouthwashes, enemas, ointments, plasters, jellies, creams, patches, cataplasms, external powders, or suppositories) can be preferably administered. Injections may be emulsions whose type is O/W, W/O, O/W/O, W/G/W, or the like.

A pharmaceutical composition can be obtained by mixing an effective amount of the compound according to the present invention with various pharmaceutical additives appropriate for the dosage form, such as an excipient, a binder, a disintegrant, and a lubricant, as necessary. Furthermore, the pharmaceutical composition can be prepared into a pharmaceutical composition for use for a child, an elderly, a patient with a serious case, or a surgical operation, by appropriately changing the effective amount of the compound according to the present invention, the dosage form, and/or various pharmaceutical additives. For example, a pharmaceutical composition for use for a child may be administered to a neonate (less than 4 weeks after birth), an infant (from 4 weeks after birth to less than 1 year), a preschool child (from 1 year to less than 7 years), a child (from 7 years to less than 15 years), or a patient 15 years to 18 years of age. For example, a pharmaceutical composition for an elderly may be administered to a patient 65 years of age or older.

It is desirable to set the amount of administration of the pharmaceutical composition of the present invention, after considering the age and body weight of the patient, the type and degree of the disease, the route of administration, and the like; however, in the case of oral administration, the amount of administration is usually 0.05 to 300 mg/kg/day and is preferably in the range of 0.1 to 10 mg/kg/day. In the case of parenteral administration, the amount of administration may vary greatly depending on the route of administration; however, the amount of administration is usually 0.005 to 10 mg/kg/day and is preferably in the range of 0.01 to 1 mg/kg/day. This may be administered once a day or several times a day.

The compound according to the present invention can be used in combination with another therapeutic agent for Parkinson's disease, Alzheimer's disease, psychosis, or depression (hereinafter, referred to as concomitant drug), for the purpose of enhancing the action of the compound, reducing the amount of administration of the compound, or the like. At this time, the timing of administration for the compound according to the present invention and the concomitant drug is not limited, and these may be administered simultaneously to the target of administration or may be administered with a time difference. Furthermore, the compound according to the present invention and the concomitant drug may be administered as two or more kinds of preparations each including active ingredients, or may be administered as a single preparation including those active ingredients.

The amount of administration of the concomitant drug can be appropriately selected based on the clinically used dosage. Furthermore, the blending ratio of the compound according to the present invention and the concomitant drug can be appropriately selected according to the target of administration, the route of administration, the target disease, symptoms, combination, and the like. For example, when the target of administration is a human being, 0.01 to 100 parts by weight of the concomitant drug may be used relative to 1 part by weight of the compound according to the present invention.

Examples of the therapeutic agent for Parkinson's disease include levodopa preparations.

Examples of the therapeutic agent for Alzheimer's disease include donepezil.

Examples of the therapeutic agent for psychosis include quetiapine.

Examples of the therapeutic agent for depression include escitalopram.

EXAMPLES

Hereinafter, the present invention will be described in more detail by way of Examples, Reference Examples, and Test Examples; however, the present invention is not intended to be limited by these.

Furthermore, abbreviations used in the present description denote the following meanings.

Boc: tert-Butoxycarbonyl $CDCl_3$: Deuterated chloroform

CDI: Carbonyldiimidazole

Cbz: Benzyloxycarbonyl

DMF: N,N-Dimethylformamide

DMSO: Dimethyl sulfoxide

EDC: 1-Ethyl-3-(3-dimethylaminopropyl)carbodiimide

HATU: O-(7-Azabenzotriazol-1-yl)-1,1,3,3-tetramethyluronium hexafluorophosphate

NMP: N-Methylpyrrolidone

TFA: Trifluoroacetic acid

NMM: N-Methylmorpholine

THF: Tetrahydrofuran $PdCl_2$(dppf): [1,1'-bis(Diphenylphosphino)ferrocene]dichloropalladium(II)

(Method for Identifying Compound)

The NMR analysis obtained in each Example was performed at 400 MHz, and measurement was made using DMSO-$d_6$ and $CDCl_3$. Furthermore, when NMR data are shown, there are occasions in which all the measured peaks are not described.

The term "retention time (RT)" in the description indicates retention time in LC/MS: liquid chromatography/mass spectrometry, and the retention time was measured under the following conditions.

(Measurement Condition 1)

Column: Shim-pack XR-ODS (2.2 μm, i.d. 3.0×50 mm) (Shimadzu)

Flow rate: 1.6 mL/min

UV detection wavelength: 254 nm

Mobile phase: [A] was 0.1% formic acid-containing aqueous solution, and [B] was 0.1% formic acid-containing acetonitrile solution.

Gradient: A linear gradient of 10% to 100% solvent [B] was carried out for 3 minutes, and then 100% solvent [B] was maintained for 0.5 minutes.

(Measurement Condition 2)

Column: ACQUITY UPLC (registered trademark) BEH C18 (1.7 μm, i.d. 2.1×50 mm) (Waters)

Flow rate: 0.8 mL/min

UV detection wavelength: 254 nm

Mobile phase: [A] was 0.1% formic acid-containing aqueous solution, and [B] was 0.1% formic acid-containing acetonitrile solution.

Gradient: A linear gradient of 5% to 100% solvent [B] was carried out for 3.5 minutes, and then 100% solvent [B] was maintained for 0.5 minutes.

Incidentally, in the description, the description of MS (m/z) indicates a value observed by mass spectrometry.

Example 1

Synthesis of Compound (I-016)

[Chemical formula 66]

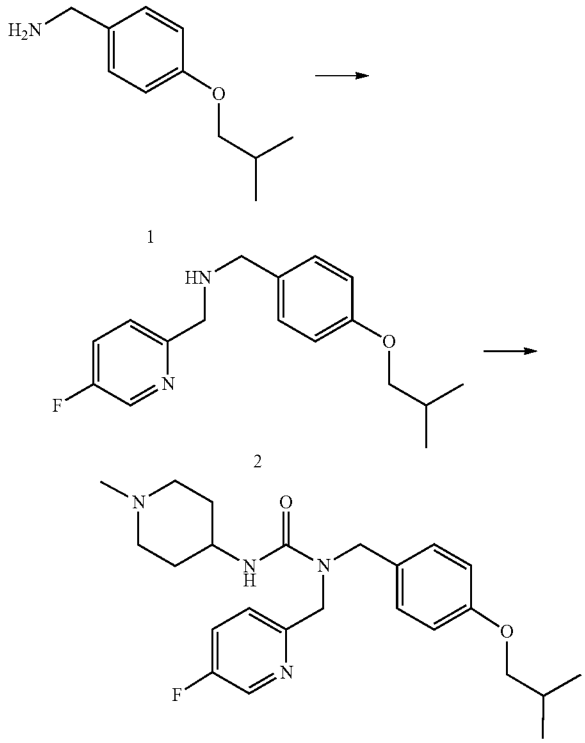

1

2

I-016

Step 1 Synthesis of Compound 2

5-Fluoropicolinaldehyde (1.54 g, 12.3 mmol) was dissolved in ethanol (20 mL), and Compound 1 (2.00 g, 11.2 mmol) (the synthesis method is described in Bioorganic and Medicinal Chemistry Letters, 2015, Vol. 25, No. 5, pp. 1053-1056) was added thereto, then the mixture was stirred at 80° C. for 30 minutes. Sodium borohydride (506 mg, 13.4 mmol) was added to the solution under ice cooling. The mixture was stirred at room temperature for 30 minutes. A saturated aqueous solution of ammonium chloride (10 mL) was added to stop the reaction. Ethyl acetate (10 mL) was added, and the mixture was stirred at room temperature for a while. Water (10 mL) and potassium carbonate (2 g) were added, and the mixture was extracted with ethyl acetate (50 mL). The organic layer was washed with water (20 mL). The solvent was distilled off under reduced pressure, and the obtained residue was purified by amino silica gel column chromatography (20 to 100% ethyl acetate-hexane) and diol silica gel column chromatography (20 to 100% ethyl acetate-hexane) to afford Compound 2 (2.11 g, 7.30 mmol, yield 66%) as a yellow oil.

1H-NMR (CDCl3) δ: 1.02 (6H, d, J=6.8 Hz), 2.02-2.12 (1H, m), 3.71 (2H, d, J=6.5 Hz), 3.76 (2H, s), 3.89 (2H, s), 6.86 (2H, d, J=8.5 Hz), 7.25 (2H, d, J=8.5 Hz), 7.29-7.40 (2H, m), 8.41 (1H, d, J=2.0 Hz).

Step 2 Synthesis of Compound (I-016)

A solution of 1-methylpiperidine-4-amine (0.634 g, 5.55 mmol) in acetonitrile (2 mL) was added dropwise to a suspension of carbonyldiimidazole (0.843 g, 5.20 mmol) in acetonitrile (3.0 mL) at room temperature over 2 minutes. The reaction solution was stirred at room temperature for 30 minutes. A solution of Compound 2 (1.00 g, 3.47 mmol) in acetonitrile (5.0 mL) and triethylamine (0.961 mL, 6.94 mmol) were added, and the mixture was stirred at 80° C. for 1.5 hours. In another reaction vessel, a solution of 1-methylpiperidine-4-amine (0.634 g, 5.55 mmol) in acetonitrile (2 mL) was added dropwise to a suspension of carbonyldiimidazole (0.843 g, 5.20 mmol) in acetonitrile (3.0 mL) at room temperature over 2 minutes, and the mixture was stirred at room temperature for 30 minutes. This reaction solution was added to the reaction solution of Compound 2, and the mixture was stirred at 80° C. for 1.5 hours. Water (10 mL) was added to stop the reaction. The mixture was extracted with ethyl acetate (100 mL). The organic layer was washed three times with a mixed solution of water (45 mL) and a saturated aqueous solution of sodium chloride (5 mL), and once with water (10 mL). The solvent was distilled off under reduced pressure, and the obtained residue was purified by diol silica gel column chromatography (0 to 5% methanol-chloroform) to afford Compound (I-016) (1.27 g, 2.97 mmol, yield 86%) as a colorless oil.

1H-NMR (CDCl3) δ: 1.02 (6H, d, J=6.8 Hz), 1.35-1.48 (2H, m), 1.86-2.00 (2H, m), 2.00-2.17 (3H, m), 2.25 (3H, s), 2.54-2.83 (2H, m), 3.61-3.73 (1H, m), 3.70 (2H, d, J=6.5 Hz), 4.42 (2H, s), 4.49 (2H, s), 5.78 (1H, s), 6.84 (2H, d, J=8.4 Hz), 7.03 (1H, dd, J=8.5, 4.0 Hz), 7.16 (2H, d, J=8.4 Hz), 7.31 (1H, td, J=8.4, 2.8 Hz), 8.35 (1H, d, J=2.4 Hz).

Reference Example 1

Synthesis of Compound 3

[Chemical formula 67]

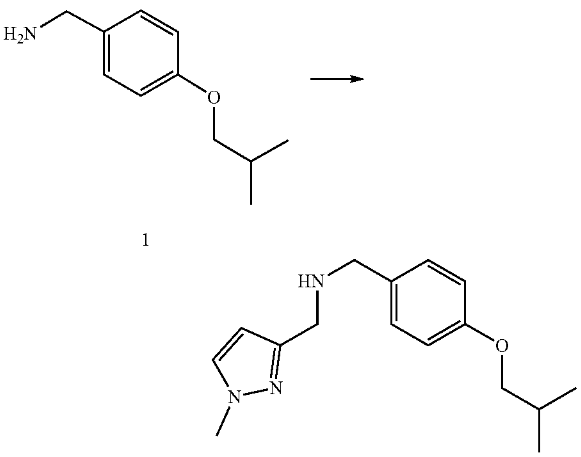

1

3

Step 1 Synthesis of Compound 3

Compound 1 (3.39 g, 18.92 mmol) was added to a solution of 1-methyl-1-pyrazole-3-carbaldehyde (2.50 g, 22.70 mmol) in ethanol (25 mL), and the mixture was stirred at 80° C. for 1 hour. After cooling to 0° C., sodium borohydride (0.71 g, 18.92 mmol) was added, and the mixture was stirred at 0° C. for 1.5 hours. A saturated aqueous solution of ammonium chloride (10 mL) was added, and the mixture was stirred for 15 minutes. A 20% aqueous solution of potassium carbonate (20 mL) was added, and the mixture was extracted with ethyl acetate. The organic layer was washed with water, and then dried over anhydrous magnesium sulfate. The solvent was distilled off under reduced pressure, and the obtained residue was purified by amino silica gel column chromatography (hexane-ethyl acetate) to afford Compound 3 (4.5 g, yield 87%).

1H-NMR (CDC13) δ: 1.01 (6H, d, J=6.8 Hz), 2.04-2.10 (1H, m), 3.72 (2H, d, J=10.2 Hz), 3.76 (2H, s), 3.80 (2H, s), 3.86 (3H, s), 6.17 (1H, d, J=1.8 Hz), 6.85 (2H, d, J=8.5 Hz), 7.23-7.28 (4H, m).

Example 2

Synthesis of Compound (I-043)

[Chemical formula 68]

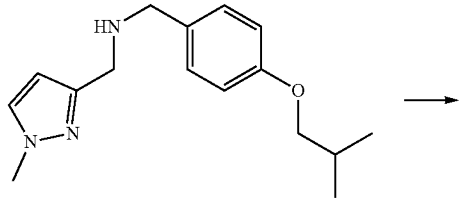

3

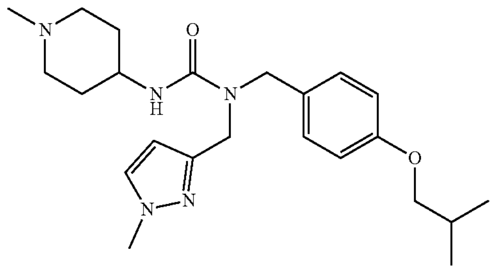

I-043

Step 1 Synthesis of Compound (I-043)

Compound (I-043) (126 mg, 0.304 mmol, yield 56%) was obtained as a yellow oil in the same manner as in Step 2 of Example 1 by using 1-methylpiperidine-4-amine and Compound 3.

1H-NMR (CDC13) δ: 1.02 (6H, d, J=6.8 Hz), 1.30-1.49 (2H, m), 1.85-1.96 (2H, m), 2.01-2.17 (3H, m), 2.25 (3H, s), 2.54-2.80 (2H, m), 3.61-3.74 (1H, m), 3.71 (2H, d, J=6.5 Hz), 3.83 (3H, s), 4.26 (2H, s), 4.48 (2H, s), 5.36 (1H, d, J=5.3 Hz), 5.89 (1H, d, J=1.5 Hz), 6.85 (2H, d, J=8.3 Hz), 7.21 (2H, d, J=8.3 Hz), 7.23 (1H, d, J=1.8 Hz).

Example 3

Synthesis of Compound (I-028)

[Chemical formula 69]

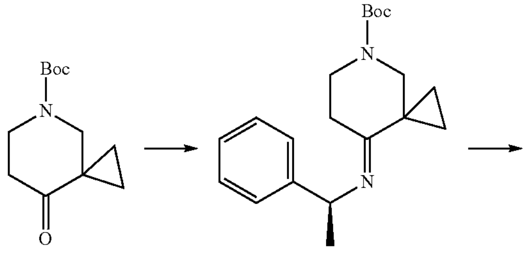

4 5

-continued

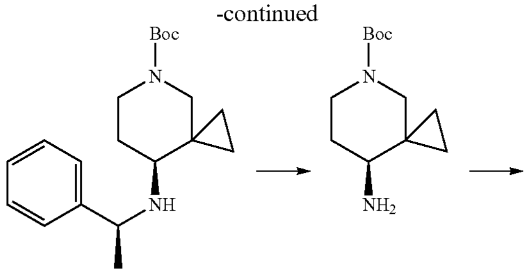

6 7

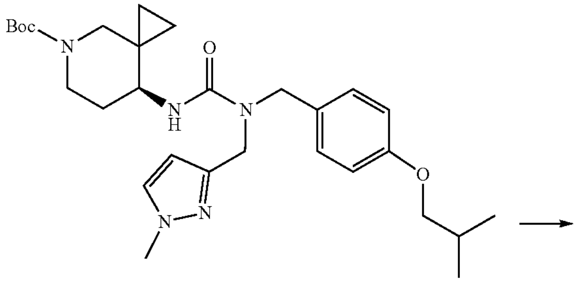

8

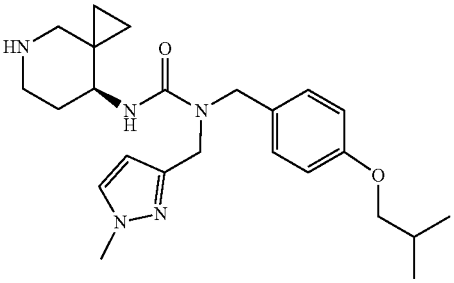

I-028

Step 1 Synthesis of Compound 5

Under ice cooling, Compound 4 (3.39 g, 18.92 mmol) was added to (S)-1-phenethyl-1-amine (1.29 g, 10.7 mmol), and the mixture was stirred at room temperature for 18 hours. Diethyl ether (60 mL) was added and the mixture was stirred at room temperature for 30 minutes. After removing the resulting solid by filtration, the solvent was removed under reduced pressure to afford Compound 5 (2.8 g, yield 96%).

Step 2 Synthesis of Compound 6

Sodium borohydride (0.16 g, 4.26 mmol) was added to a solution of Compound 5 (2.8 g, 8.52 mmol) in ethanol (28 mL) at −78° C., and the mixture was stirred at −78° C. for 2 hours. Saturated sodium bicarbonate water (20 mL) was added, and the mixture was extracted with ethyl acetate. The organic layer was washed with saturated sodium chloride water, and then dried over anhydrous magnesium sulfate. The solvent was distilled off under reduced pressure, and the obtained residue was purified by amino silica gel column chromatography (hexane-ethyl acetate) to afford Compound 6 (2.1 g, yield 75%).

$^1$H-NMR ($CDCl_3$) δ: 0.29-0.50 (m, 4H), 1.30 (d, J=6.4 Hz, 2H), 1.42 (s, 9H), 1.45-1.70 (m, 2H), 2.18 (s, 1H), 2.92-3.06 (s, 1H), 3.28-3.49 (m, 3H), 3.83 (q, J=6.6 Hz, 1H), 7.22 (dd, J=8.7, 4.5 Hz, 1H), 7.30 (d, J=4.3 Hz, 4H).

Step 3 Synthesis of Compound 7

Methanol (1.6 mL), ammonium formate (150 mg, 2.38 mmol), and palladium hydroxide on carbon (40 mg, 0.14 mmol) were added to Compound 6 (157 mg, 0.48 mmol), and the mixture was stirred at 60° C. for 1 hour. The reaction solution was filtered to remove palladium hydroxide on carbon. The solvent was removed under reduced pressure to afford Compound 7 (102 mg, yield 95%).

1H-NMR (CDCl3) δ: 0.32-0.50 (m, 4H), 1.45 (s, 9H), 1.50-1.62 (m, 1H), 1.80-1.88 (m, 1H), 2.62 (dd, J=10.0, 6.4 Hz, 1H), 3.05 (d, J=12.2 Hz, 1H), 3.41 (d, J=13.6 Hz, 1H), 3.45-3.62 (m, 2H).

Step 4 Synthesis of Compound 8

Compound 8 was synthesized in the same manner as in Step 2 of Example 1 by using Compound 7 and Compound 3.

1H-NMR (CDCl3) δ: 0.30 (1H, s), 0.42 (4H, s), 1.01 (3H, s), 1.03 (3H, s), 1.44 (9H, s), 1.61-1.64 (1H, m), 1.79 (1H, br s), 2.08-2.09 (1H, m), 3.14-3.17 (1H, m), 3.27-3.31 (1H, m), 3.47 (2H, br s), 3.70 (1H, s), 3.72 (1H, s), 3.82 (3H, s), 4.23 (2H, s), 4.47 (1H, d, J=14.7 Hz), 4.52 (1H, d, J=14.7 Hz), 5.65 (1H, s), 5.83 (1H, s), 6.86 (2H, d, J=8.3 Hz), 7.21 (2H, d, J=8.3 Hz), 7.24 (1H, s).

Step 5 Synthesis of Compound (I-028)

Dichloromethane (1.1 mL) and trifluoroacetic acid (230 μL, 2.99 mmol) were added to Compound 8, and the mixture was stirred at room temperature for 1.5 hours. Saturated sodium bicarbonate water (1 mL) was added, and the mixture was extracted with ethyl acetate. The organic layer was washed with saturated sodium chloride water, and then dried over anhydrous magnesium sulfate. The solvent was distilled off under reduced pressure, and the obtained residue was purified by amino silica gel column chromatography (hexane-ethyl acetate, ethyl acetate-methanol) to afford Compound (I-028) (38.8 mg, yield 41%) as a colorless oil.

1H-NMR (CDCl3) δ: 0.14-0.18 (1H, m), 0.27-0.31 (1H, m), 0.35-0.37 (1H, m), 0.44-0.46 (1H, m), 1.02 (6H, d, J=6.5 Hz), 1.56-1.57 (2H, m), 1.75-1.80 (1H, m), 2.08-2.09 (1H, m), 2.53 (1H, d, J=13.0 Hz), 2.66 (1H, d, J=13.0 Hz), 2.81-2.86 (1H, m), 2.91-2.93 (1H, m), 3.71 (3H, d, J=6.5 Hz), 3.85 (3H, s), 4.25 (2H, s), 4.46 (1H, d, J=15.1 Hz), 4.53 (1H, d, J=15.3 Hz), 5.51 (1H, s), 5.85 (1H, s), 6.86 (2H, d, J=8.0 Hz), 7.21 (2H, d, J=8.0 Hz), 7.24 (1H, s).

Example 4

Synthesis of Compound (I-037)

[Chemical formula 70]

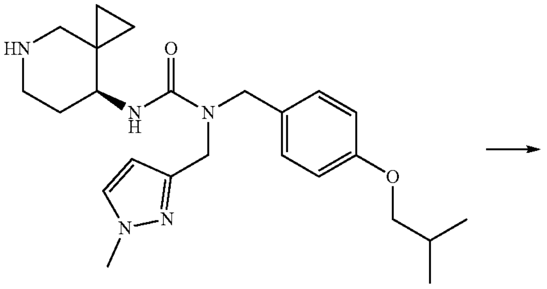

I-028

-continued

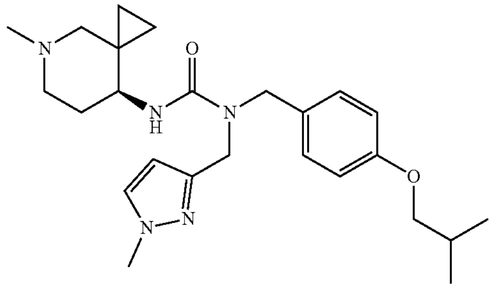

I-037

Step 1 Synthesis of (I-037)

Tetrahydrofuran (1.1 mL), methanol (1.1 mL), formaldehyde (36.2 μL, 1.31 mmol), and sodium triacetoxyborohydride (186.0 g, 0.87 mmol) were added to Compound (I-028) (186.2 mg, 0.43 mmol), and the mixture was stirred at room temperature for 18 hours. Saturated sodium bicarbonate water (1 mL) was added, and the mixture was extracted with ethyl acetate. The organic layer was washed with water, and then dried over anhydrous magnesium sulfate. The solvent was distilled off under reduced pressure, and the obtained residue was purified by amino silica gel column chromatography (hexane-ethyl acetate, ethyl acetate-methanol) to afford Compound (I-037) (4.9 mg, yield 3%) as a colorless oil.

1H-NMR (CDCl3) δ: 0.20-0.24 (1H, m), 0.33-0.36 (1H, br m), 0.40 (1H, dd, J=8.8, 4.1 Hz), 0.46 (1H, dd, J=8.8, 4.1 Hz), 1.01 (3H, s), 1.03 (3H, s), 1.85 (3H, s), 2.07-2.10 (2H, m), 2.15-2.18 (1H, br m), 2.23 (3H, s), 2.38-2.40 (2H, br m), 3.70 (1H, s), 3.72 (1H, s), 3.84 (3H, s), 4.26 (2H, s), 4.45 (1H, d, J=15.2 Hz), 4.51 (1H, d, J=15.2 Hz), 5.36 (1H, br s), 5.87 (1H, d, J=1.9 Hz), 6.86 (2H, d, J=8.5 Hz), 7.21 (2H, d, J=8.5 Hz), 7.24 (1H, d, J=1.9 Hz).

Example 5

Synthesis of Compound (I-030)

[Chemical formula 71]

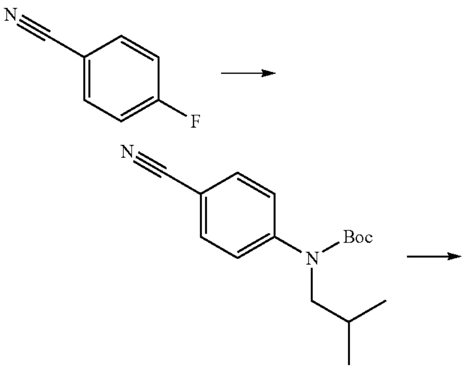

9

-continued

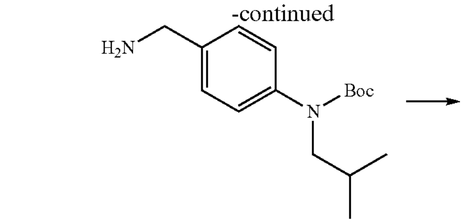

10

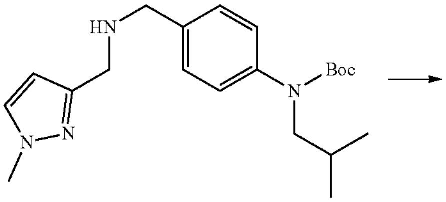

11

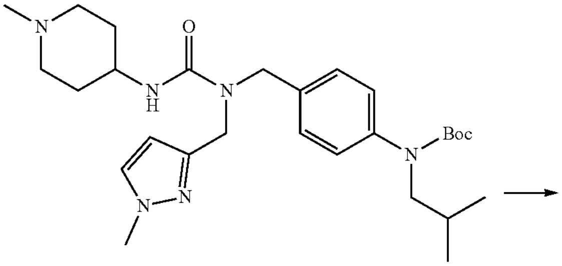

12

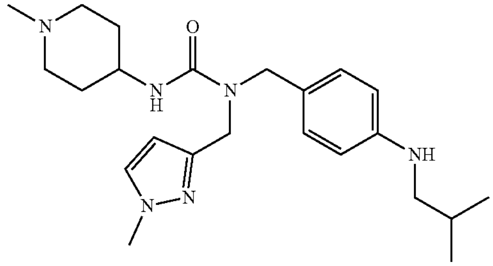

I-030

Step 1 Synthesis of Compound 9

Isobutylamine (20.7 mL, 206 mmol) and cesium carbonate (16.1 g, 49.5 mmol) were added to a solution of 4-fluorobenzonitrile (5.00 g, 41.3 mmol) in dimethyl sulfoxide (50.0 mL), and the mixture was stirred at 70° C. for 4 hours. Water (200 mL) was added to the reaction solution, and the mixture was extracted with ethyl acetate (200 mL). The organic layer was washed with water (100 mL) three times. The solvent was distilled off under reduced pressure. The obtained residue was dissolved in methylene chloride (37 mL), di-tert-butyl dicarbonate (9.86 mL, 42.5 mmol) and 4-dimethylaminopyridine (0.519 g, 4.25 mmol) were added, and the mixture was stirred at room temperature for 30 minutes. 4-Dimethylaminopyridine (5.19 g, 42.5 mmol) was added, and the mixture was stirred at room temperature for 5 hours. Di-t-butyl dicarbonate (9.86 mL, 42.5 mmol) was added, and the mixture was allowed to stand at room temperature for 5 days. Under ice cooling, N-methylpiperidine (9.45 mL, 85.0 mmol) was added to stop the reaction. The solvent was distilled off under reduced pressure, and the obtained residue was purified by silica gel column chromatography (0 to 30% ethyl acetate-hexane) to afford Compound 9 (2.32 g, 8.45 mmol, yield 20%) as a white solid.

1H-NMR (CDCl3) δ: 0.87 (6H, d, J=6.8 Hz), 1.45 (9H, s), 1.74-1.81 (1H, m), 3.54 (2H, d, J=7.5 Hz), 7.35 (2H, d, J=8.5 Hz), 7.62 (2H, d, J=8.5 Hz).

Step 2 Synthesis of Compound 10

Compound 9 (750 mg, 2.73 mmol) was dissolved in methanol (7.5 mL) and acetic acid (0.75 mL). 10% Palladium on carbon (375 mg) was added, and the mixture was stirred under a 1 atm hydrogen atmosphere at room temperature for 19 hours. 30 mL of ethyl acetate was added, and the mixture was filtered through Celite. A 10% aqueous solution of potassium carbonate (20 mL) was added to the filtrate, and the mixture was extracted with ethyl acetate (20 mL). The organic layer was washed with water (20 mL) twice. The solvent was distilled off under reduced pressure. The obtained residue was purified by amino silica gel column chromatography (30 to 100% ethyl acetate-hexane) to afford Compound 10 (488 g, 1.75 mmol, yield 64%) as a colorless oil.

1H-NMR (CDCl3) δ: 0.88 (6H, d, J=6.5 Hz), 1.43 (9H, s), 1.50-1.61 (2H, m), 1.72-1.79 (1H, m), 3.47 (2H, d, J=7.3 Hz), 3.86 (2H, s), 7.16 (2H, d, J=8.0 Hz), 7.27 (2H, d, J=9.8 Hz).

Step 3, Step 4, and Step 5 Synthesis of Compound (I-030)

Compound 11 was synthesized in the same manner as in Reference Example 1 by using 1-methyl-1-pyrazole-3-carbaldehyde and Compound 10, Compound 12 was synthesized in the same manner as in Step 1 of Example 2, and then Compound (I-030) was obtained as a colorless oil in the same manner as in Step 5 of Example 3.

1H-NMR (CDCl3) δ: 0.97 (3H, s), 0.99 (3H, s), 1.39-1.41 (2H, m), 1.87-1.91 (3H, m), 2.08-2.11 (2H, br m), 2.24 (3H, s), 2.65 (2H, br s), 2.92 (2H, d, J=4.3 Hz), 3.67 (2H, br s), 3.83 (3H, s), 4.28 (2H, s), 4.41 (2H, s), 5.28 (1H, br s), 5.92 (1H, d, J=1.9 Hz), 6.56 (2H, d, J=8.3 Hz), 7.10 (2H, d, J=8.3 Hz), 7.23 (1H, d, J=1.9 Hz).

Example 6

Synthesis of Compound (I-012)

[Chemical formula 72]

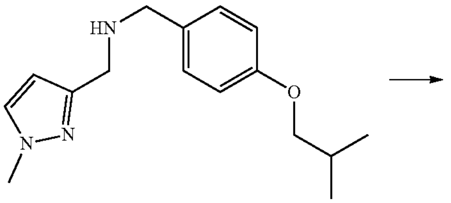

3

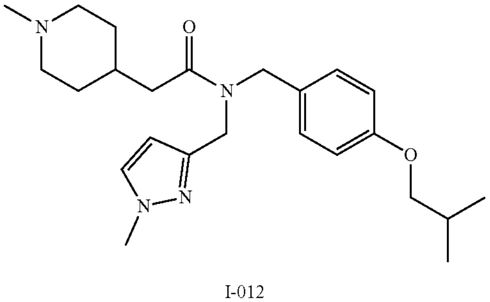

I-012

Step 1 Synthesis of Compound (I-012)

1-Methylpiperidine-4-carboxylic acid (56.2 mg, 0.36 mmol), HATU (102.0 mg, 0.27 mmol), and diisopropylethylamine (62.5 μL, 0.36 mmol) were added to a solution of Compound 3 (48.9 mg, 0.18 mmol) in dimethylformamide (489 μL), and the mixture was stirred at room temperature for 1 hour. Saturated sodium bicarbonate water (1 mL) was added, and the mixture was extracted with ethyl acetate. The organic layer was washed with brine, and then dried over anhydrous magnesium sulfate. The solvent was distilled off under reduced pressure, and the obtained residue was purified by amino silica gel column chromatography (chloroform-methanol) to afford Compound (I-012) (44.9 mg, yield 61%) as a yellow oil.

1H-NMR (CDCl3) δ: 1.02 (12H, t, J=6.5 Hz), 1.19-1.31 (4H, m), 1.76 (4H, s), 1.94 (6H, d, J=10.3 Hz), 2.03-2.09 (2H, m), 2.24-2.28 (7H, m), 2.38 (2H, d, J=6.8 Hz), 2.79-2.82 (5H, br m), 3.70 (4H, t, J=3.3 Hz), 3.84 (3H, s), 3.87 (3H, s), 4.36 (2H, s), 4.47 (2H, s), 4.55 (4H, s), 6.00 (1H, s), 6.18 (1H, s), 6.84 (4H, t, J=8.5 Hz), 7.06 (2H, d, J=8.3 Hz), 7.20 (2H, d, J=8.5 Hz), 7.27 (1H, s), 7.28 (1H, s).

Example 7

Synthesis of Compound (I-112)

[Chemical formula 73]

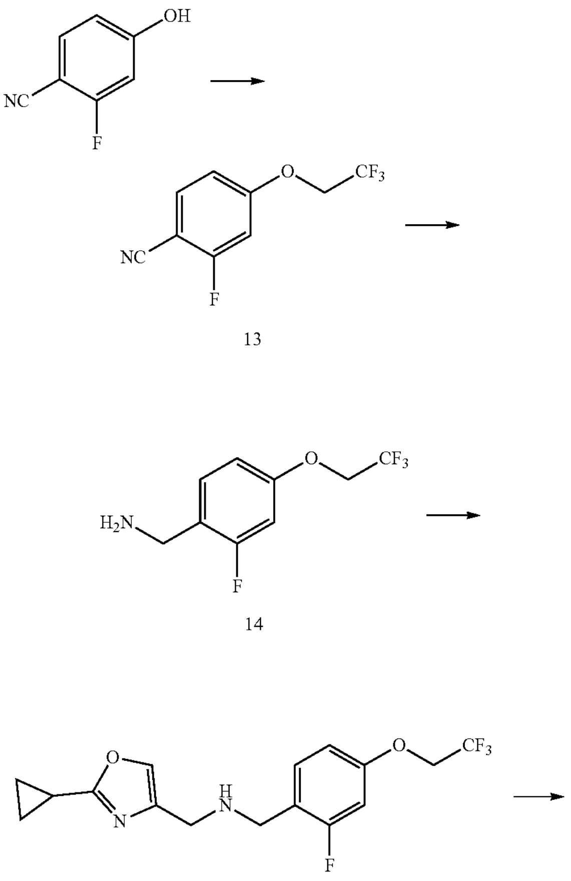

13

14

15

-continued

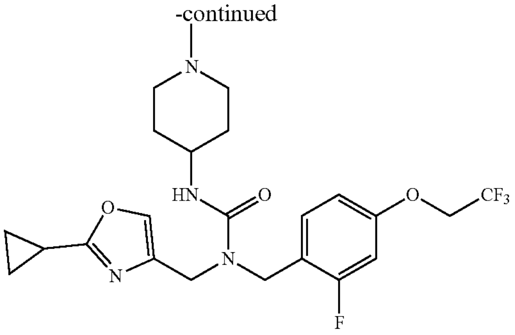

I-112

Step 1 Synthesis of Compound 13

2-Fluoro-4-hydroxybenzonitrile (5.00 g, 36.5 mmol) was dissolved in DMF (50 mL), potassium carbonate (15.12 g, 109 mmol), and 2,2,2-trifluoroethyl trifluoromethanesulfonate (5.52 mL, 38.3 mmol) were added, and the mixture was stirred at room temperature for 1 hour. Water (100 mL) was added, and the mixture was extracted with ethyl acetate (100 mL). The organic layer was washed with water (100 mL) three times, and then dried over anhydrous magnesium sulfate. The solvent was distilled off under reduced pressure to afford Compound 13 (7.90 g, yield 98%) as a crude product.

$^1$H-NMR ($CDCl_3$) δ: 4.41 (2H, q, J=7.8 Hz), 6.72-6.89 (2H, m), 7.58-7.64 (1H, m).

Step 2

Compound 13 (4.17 g, 19.0 mmol) was dissolved in THF (41.7 mL), a 0.89 mol/L borane-THF solution (32.1 mL, 28.5 mmol) was added, and the mixture was heated and refluxed for 70 minutes. Under ice cooling, 2 mol/L hydrochloric acid (28.5 mL, 57.1 mmol) was added, and then the mixture was heated and refluxed for 1 hour. Ethyl acetate (100 mL) was added, and the mixture was separated. A 2 mol/L aqueous solution of sodium hydroxide (28.5 mL, 57.1 mmol) was added to the obtained aqueous layer, and the mixture was extracted twice with chloroform (100 mL). The organic layer was dried over anhydrous sodium sulfate, and then the solvent was distilled off under reduced pressure to afford Compound 14 (1.46 g, yield 34%).

$^1$H-NMR ($CDCl_3$) δ: 3.85 (2H, s), 4.33 (2H, q, J=8.1 Hz), 6.65-6.70 (2H, m), 7.23-7.29 (1H, m).

Step 3 Synthesis of Compound 15

Compound 15 (614 mg, yield 61%) was synthesized in the same manner as in Step 1 of Example 1 by using Compound 14 and 2-cyclopropyl-4-oxazole-carbaldehyde.

$^1$H-NMR ($CDCl_3$) δ: 0.98-1.08 (4H, m), 1.98-2.06 (1H, m), 3.65 (2H, s), 3.80 (2H, s), 4.29-4.36 (2H, m), 6.64-6.74 (2H, m), 7.30 (1H, t, J=8.4 Hz), 7.35 (1H, s).

Step 4 Synthesis of Compound (I-112)

Compound (I-112) (219 mg, yield 72%) was synthesized in the same manner as in Step 2 of Example 1 by using Compound 15 and 1-methylpiperidine-4-amine.

1H-NMR (CDCl3) δ: 1.00-1.05 (4H, m), 1.45-1.57 (2H, m), 1.93-2.03 (3H, m), 2.08-2.17 (2H, m), 2.28 (3H, s), 2.72-2.81 (2H, m), 3.61-3.72 (1H, m), 4.09 (2H, s), 4.33 (2H, q, J=8.0 Hz), 4.46 (2H, s), 6.07 (1H, d, J=7.5 Hz), 6.63-6.73 (2H, m), 7.23 (1H, s), 7.39 (1H, t, J=8.6 Hz).

Example 8

Synthesis of Compound (I-086)

[Chemical formula 74]

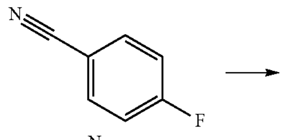

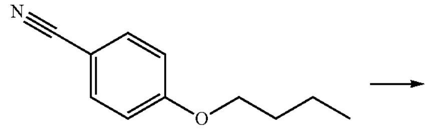

16

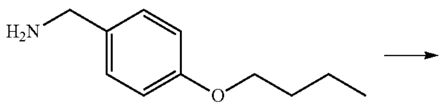

17

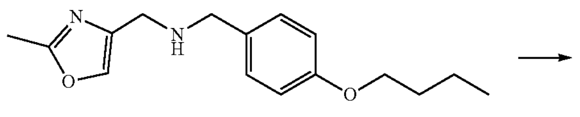

18

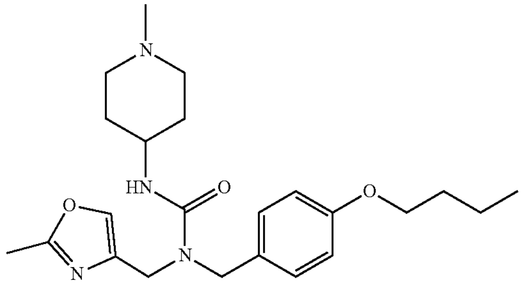

I-086

Step 1 Synthesis of Compound 16

1-Butanol (9.00 g, 121 mmol) was dissolved in DMF (56 mL) and THF (14 mL), sodium hydride (60 w/w %, 4.62 g, 116 mmol) was added under ice cooling, and the mixture was stirred for 30 minutes. Under ice cooling, a solution of 4-fluorobenzonitrile (7.00 g, 57.8 mmol) in DMF (14 mL) was added dropwise, and the mixture was stirred at room temperature for 1 hour. The mixture was quenched with water (300 mL) and extracted twice with ethyl acetate (60 mL). The organic layer was washed with water (300 mL), and then dried over anhydrous sodium sulfate. The solvent was distilled off under reduced pressure to afford Compound 16 (12.1 g) as a crude product.

1H-NMR (CDCl3) δ: 0.98 (3H, t, J=7.4 Hz), 1.44-1.55 (2H, m), 1.74-1.83 (2H, m), 4.00 (2H, t, J=6.5 Hz), 6.93 (2H, d, J=8.9 Hz), 7.57 (2H, d, J=8.9 Hz).

Step 2 Synthesis of Compound 17

Compound 16 (12.1 g, 68.9 mmol) was dissolved in methanol (217 mL), acetic acid (7.89 mL, 138 mmol) and 10 w/w % palladium on carbon (1.47 g) were added, and the mixture was stirred under a 1 atm hydrogen atmosphere for 2.5 hours. The reaction solution was filtered through Celite, and the solvent of the filtrate was distilled off under reduced pressure. A 1 mol/L aqueous solution of sodium hydroxide (150 mL) was added to the obtained residue, and the mixture was extracted twice with ethyl acetate (150 mL). The organic layer was dried over anhydrous sodium sulfate, and then the solvent was distilled off under reduced pressure to afford Compound 17 (12.1 g, yield 98%).

1H-NMR (CDCl3) δ: 0.97 (3H, t, J=7.3 Hz), 1.44-1.53 (2H, m), 1.71-1.81 (2H, m), 3.80 (2H, s), 3.95 (2H, t, J=6.5 Hz), 6.87 (2H, d, J=8.5 Hz), 7.21 (2H, d, J=8.5 Hz).

Step 3 Synthesis of Compound 18

Compound 18 (2.79 g, yield 90%) was synthesized in the same manner as in Step 1 of Example 1 by using Compound 17 and 2-methyl-4-oxazole-carbaldehyde.

1H-NMR (CDCl3) δ: 0.97 (3H, t, J=7.4 Hz), 1.42-1.55 (2H, m), 1.72-1.80 (2H, m), 2.44 (3H, s), 3.66 (2H, s), 3.74 (2H, s), 3.95 (2H, t, J=6.5 Hz), 6.85 (2H, d, J=8.6 Hz), 7.23 (2H, d, J=8.6 Hz), 7.40 (1H, s).

Step 4 Synthesis of Compound (I-086)

Compound (I-086) (0.125 g, yield 40%) was synthesized in the same manner as in Step 2 of Example 1 by using Compound 18 and 1-methylpiperidine-4-amine.

1H-NMR (CDCl3) δ: 7.20 (1H, s), 7.18 (2H, d, J=9.2 Hz), 6.84 (2H, d, J=9.2 Hz), 5.60 (1H, s), 4.43 (2H, s), 4.16 (2H, s), 3.95 (2H, t, J=6.5 Hz), 3.67 (1H, br s), 2.69 (2H, br s), 2.41 (3H, s), 2.26 (3H, s), 2.11 (2H, t, J=9.4 Hz), 1.96-1.92 (2H, m), 1.78-1.74 (2H, m), 1.54-1.40 (4H, m), 0.98 (3H, t, J=7.4 Hz).

Example 9

Synthesis of Compound (I-082)

[Chemical formula 75]

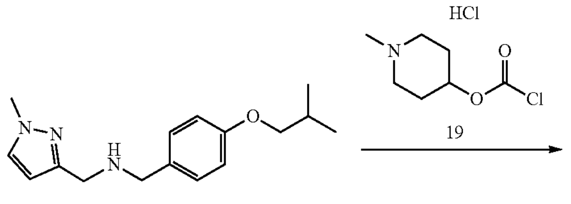

3

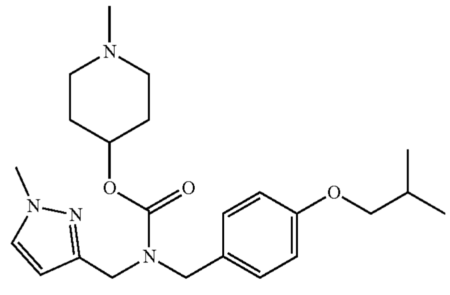

I-082

Step 1 Synthesis of Compound (I-082)

Compound 3 (49.3 mg, 0.230 mmol) and pyridine (0.053 mL, 0658 mL) were dissolved in dichloromethane (0.6 mL), and Compound 19 (49.3 mg, 0.048 mmol) (the synthesis method is described in Journal of Medicinal Chemistry, 1990, Vol. 33, No. 8, pp. 2101-2108) was added, then the mixture was stirred at room temperature for 8 hours. The reaction solution was purified by amino silica gel column chromatography to afford Compound (I-082) (20.0 mg, 0.048 mmol, yield 22%) as a colorless oil.

1H-NMR (CDCl3) δ: 1.02 (6H, d, J=6.8 Hz), 1.76 (2H, br s), 1.94 (2H, br s), 2.02-2.12 (1H, m), 2.25 (5H, br s), 2.56

(2H, br s), 3.70 (2H, d, J=6.7 Hz), 3.86 (3H, s), 4.38 (4H, dd, J=26.2, 9.7 Hz), 4.79 (1H, br s), 6.08-6.18 (1H, br m), 6.83 (2H, d, J=8.4 Hz), 7.14-7.26 (3H, m).

Example 10

Synthesis of Compound (I-108)

[Chemical formula 76]

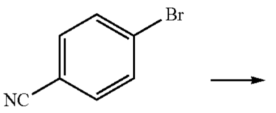

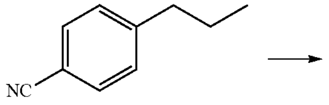

20

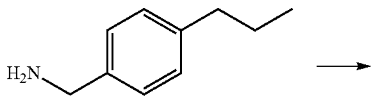

21

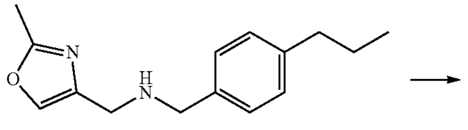

22

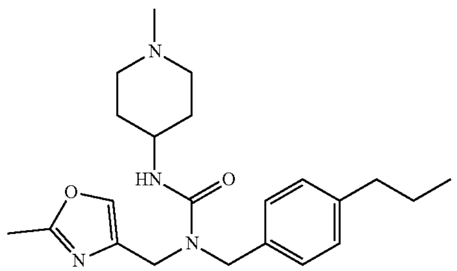

I-108

Step 1 Synthesis of Compound 20

4-Bromobenzonitrile (2.0 g, 11 mmol) was dissolved in toluene (10 mL), and propylboronic acid (1.45 g, 16.5 mmol), cesium carbonate (8.95 g, 27.5 mmol), and $PdCl_2$ (dppf) (0.40 g, 0.55 mmol) were added, then the mixture was stirred at 100° C. for 8 hours under a nitrogen atmosphere. The reaction solution was filtered through Celite, then water (5 mL) was added, and the mixture was extracted three times with ethyl acetate (20 mL). The organic layer was dried over anhydrous sodium sulfate, then the solvent was distilled off under reduced pressure, and purification was performed by silica gel column chromatography (hexane/ethyl acetate) to afford Compound 20 (1.40 g, 88%) as a pale yellow oil.

1H-NMR (CDCl3) δ: 0.94 (3H, t, J=7.4 Hz), 1.66 (2H, sextet, J=7.4 Hz), 2.64 (2H, J=7.4 Hz), 7.27 (2H, d, J=8.3 Hz), 7.57 (2H, d, J=8.3 Hz).

Step 2 Synthesis of Compound 21

Compound 20 (1.39 g) was dissolved in THF (13.9 mL), 16.1 mL of a borane-THF complex THF solution (0.89 mol/L) was added at room temperature under a nitrogen atmosphere, and the mixture was refluxed for 3 hours. After cooling in an ice bath, 2 mol/L hydrochloric acid (14.4 mL) was slowly added, and then the mixture was refluxed for 2.5 hours. The reaction solution was cooled, and then extracted with ethyl acetate (20 mL). The organic layer was extracted twice with 2 mol/L hydrochloric acid (5 mL). The aqueous layers were combined, basified with a 2 mol/L aqueous solution of sodium hydroxide, and extracted three times with chloroform (20 mL). The organic layer was dried over anhydrous sodium sulfate, and then the solvent was distilled off under reduced pressure to afford Compound 21 (1.39 g, 97%) as a colorless oil.

1H-NMR (CDCl3) δ: 0.94 (3H, t, J=7.3 Hz), 1.63 (2H, sextet, J=7.7 Hz), 2.57 (2H, t, J=7.7 Hz), 3.83 (2H, s), 7.15 (2H, d, J=8.0 Hz), 7.22 (2H, d, J=8.0 Hz).

Step 3 Synthesis of Compound 22

Compound 22 (680 mg, yield 83%) was synthesized in the same manner as in Step 1 of Example 1 by using Compound 21 and 2-methyl-4-oxazole-carbaldehyde.

1H-NMR (CDCl3) δ: 0.93 (3H, t, J=7.5 Hz), 1.63 (2H, sextet, J=7.5 Hz), 2.43 (3H, s), 2.57 (2H, t, J=7.5 Hz), 3.67 (2H, s), 3.78 (2H, s), 7.13 (2H, d, J=8.0 Hz), 7.24 (2H, d, J=8.0 Hz).

Step 4 Synthesis of Compound (I-108)

Compound (I-108) (374 mg, yield 95%) was synthesized in the same manner as in Step 2 of Example 1 by using Compound 22 and 1-methylpiperidine-4-amine.

1H-NMR (CDCl3) δ: 0.93 (3H, t, J=7.3 Hz), 1.40-1.50 (2H, m), 1.58-1.71 (2H, m), 1.92-1.96 (2H, m), 2.11 (2H, t, J=10.2 Hz), 2.26 (3H, s), 2.41 (3H, s), 2.57 (2H, t, J=7.6 Hz), 2.68 (2H, br), 3.69 (1H, br), 4.18 (2H, s), 4.47 (2H, s), 5.59 (1H, br), 7.13 (2H, d, J=8.0 Hz), 7.17 (2H, d, J=8.0 Hz), 7.18 (1H, s).

The following compounds were synthesized according to the above general synthesis method and the method described in Examples. The structure and physical properties (LC/MS data, NMR spectra) are shown in the table below.

Incidentally, in the structural formula, "wedge shape" and "dashed line" indicate the configuration. Particularly, with regard to compounds whose configurations are described, a compound described as "a" in the item of "Configuration" is a racemic compound whose relative configuration has been specified. A compound described as "b" in the item of "Configuration" is a single enantiomer whose relative configuration has been specified and whose absolute configuration is unknown. A compound described as "c" in the item of "Configuration" indicates that the configuration is determined as shown in the chemical structure.

In addition, with regard to compounds in which the bonds forming an asymmetric carbon are described by solid lines, a compound described as "d" in the item of "Configuration" is a racemic compound. A compound described as "e" in the item of "Configuration" is a racemic compound and a diastereomer mixture thereof. A compound described as "f" in the item of "Configuration" is a single enantiomer whose configuration has not been specified.

TABLE 1
| Compound No. | Structural formula | LC/MS Measurement condition | Retention time (min) | m/z | Configuration |
|---|---|---|---|---|---|
| I-001 | 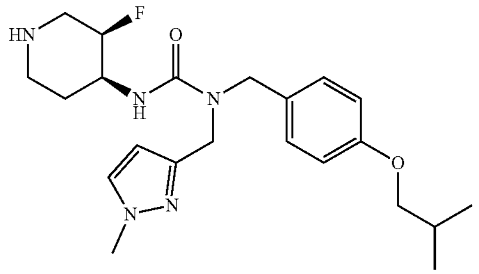 [SMILES: CC(C)COc1ccc(CN(Cc2ccn(C)n2)C(=O)N[C@H]2CCNC[C@H]2F)cc1] | 1 | 1.23 | 418 | a |
| I-002 | 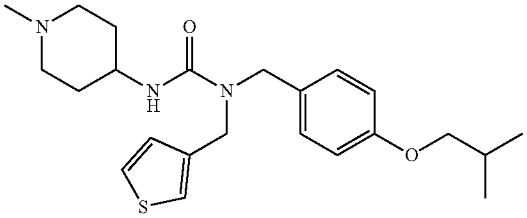 [SMILES: CC(C)COc1ccc(CN(Cc2ccsc2)C(=O)NC2CCN(C)CC2)cc1] | 1 | 1.83 | 416 | |
| I-003 | 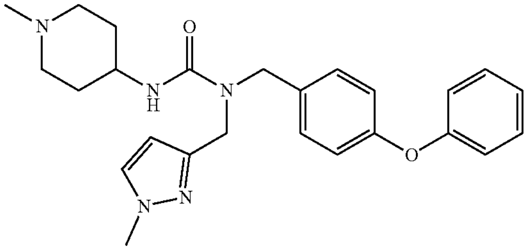 [SMILES: CN1CCC(NC(=O)N(Cc2ccc(Oc3ccccc3)cc2)Cc2ccn(C)n2)CC1] | 1 | 2.09 | 434 | |
| I-004 | 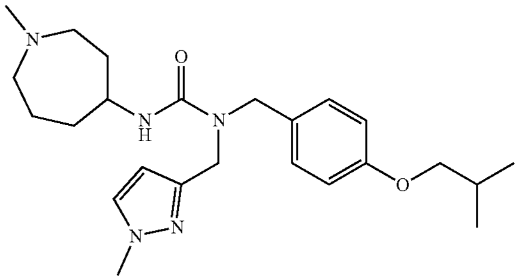 [SMILES: CC(C)COc1ccc(CN(Cc2ccn(C)n2)C(=O)NC2CCCN(C)CC2)cc1] | 1 | 1.42 | 428 | d |
| I-005 | 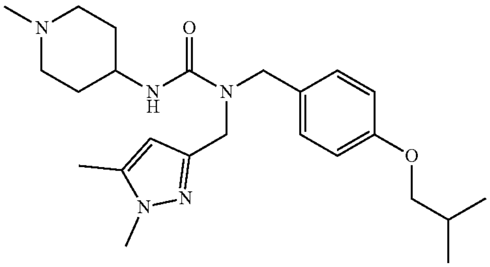 [SMILES: Cc1cc(CN(Cc2ccc(OCC(C)C)cc2)C(=O)NC2CCN(C)CC2)nn1C] | 1 | 1.24 | 428 | |

TABLE 1-continued
| Compound No. | Structural formula | LC/MS Measurement condition | Retention time (min) | m/z | Configuration |
|---|---|---|---|---|---|
| I-006 | 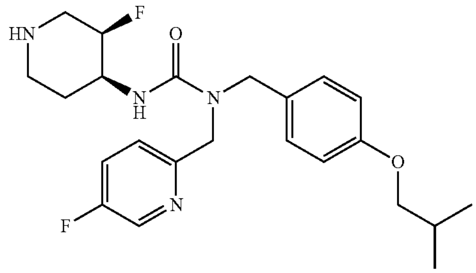 [SMILES: CC(C)COc1ccc(CN(Cc2ccc(F)cn2)C(=O)N[C@H]2CCNC[C@H]2F)cc1] | 1 | 1.3 | 433 | b |
TABLE 2
| Compound No. | Structural formula | LC/MS Measurement condition | Retention time (min) | m/z | Configuration |
|---|---|---|---|---|---|
| I-007 | 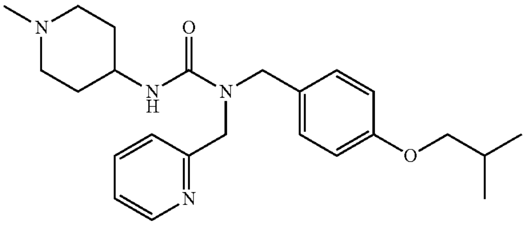 [SMILES: CC(C)COc1ccc(CN(Cc2ccccn2)C(=O)NC2CCN(C)CC2)cc1] | 1 | 1.34 | 411 | |
| I-008 | 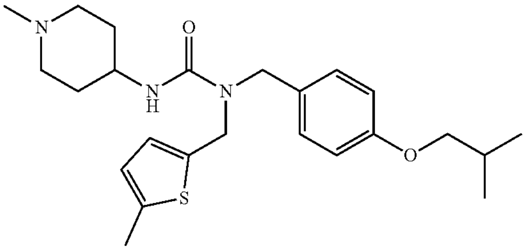 [SMILES: Cc1ccc(CN(Cc2ccc(OCC(C)C)cc2)C(=O)NC2CCN(C)CC2)s1] | 1 | 1.92 | 430 | |
| I-009 | 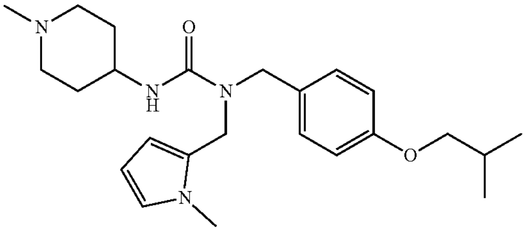 [SMILES: CC(C)COc1ccc(CN(Cc2cccn2C)C(=O)NC2CCN(C)CC2)cc1] | 1 | 1.8 | 413 | |
| I-010 | 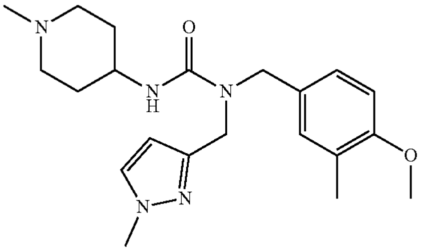 | 1 | 1.73 | 386 | |

TABLE 2-continued
| Compound No. | Structural formula | LC/MS Measurement condition | Retention time (min) | m/z | Configuration |
|---|---|---|---|---|---|
| I-011 | 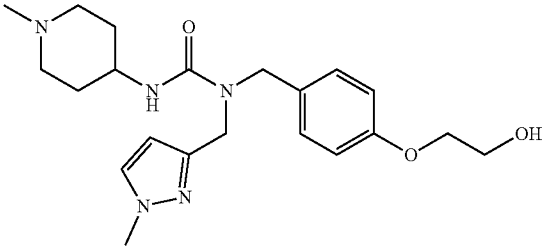 [SMILES: CN1CCC(NC(=O)N(Cc2ccc(OCCO)cc2)Cc2ccn(C)n2)CC1] | 1 | 1.3 | 402 | |
| I-012 | 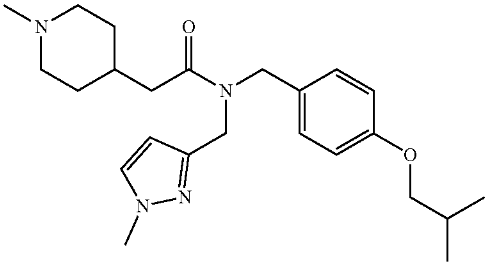 [SMILES: CC(C)COc1ccc(CN(Cc2ccn(C)n2)C(=O)CC2CCN(C)CC2)cc1] | 1 | 1.3 | 413 | |
TABLE 3
| Compound No. | Structural formula | LC/MS Measurement condition | Retention time (min) | m/z | Configuration |
|---|---|---|---|---|---|
| I-013 | 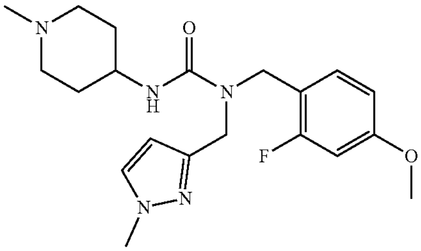 | 1 | 1.66 | 390 | |
| I-014 | 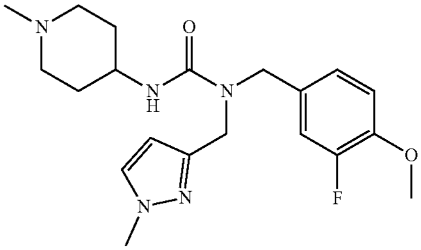 | 1 | 1.61 | 390 | |
| I-015 | 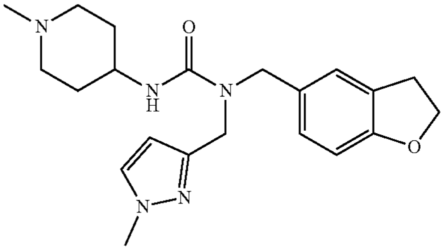 [SMILES: CN1CCC(NC(=O)N(Cc2ccc3c(c2)CCO3)Cc2ccn(C)n2)CC1] | 1 | 1.57 | 384 | |

TABLE 3-continued
| Compound No. | Structural formula | LC/MS Measurement condition | Retention time (min) | m/z | Configuration |
|---|---|---|---|---|---|
| I-016 | 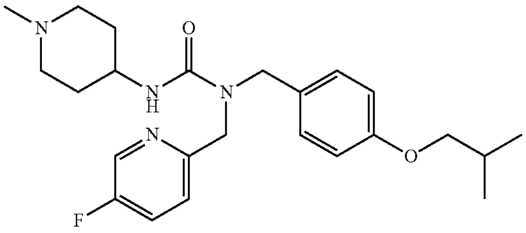 [SMILES: CC(C)COc1ccc(CN(Cc2ccc(F)cn2)C(=O)NC2CCN(C)CC2)cc1] | 2 | 1.69 | 429 | |
| I-017 | 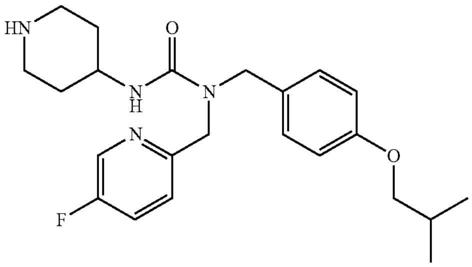 [SMILES: CC(C)COc1ccc(CN(Cc2ccc(F)cn2)C(=O)NC2CCNCC2)cc1] | 1 | 1.32 | 415 | |
| I-018 | 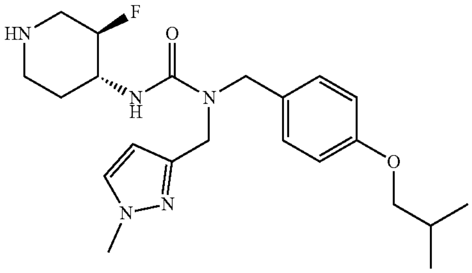 [SMILES: CC(C)COc1ccc(CN(Cc2ccn(C)n2)C(=O)N[C@@H]2CCNC[C@H]2F)cc1] | 1 | 1.23 | 418 | a |
TABLE 4
| Compound No. | Structural formula | LC/MS Measurement condition | Retention time (min) | m/z | Configuration |
|---|---|---|---|---|---|
| I-019 | 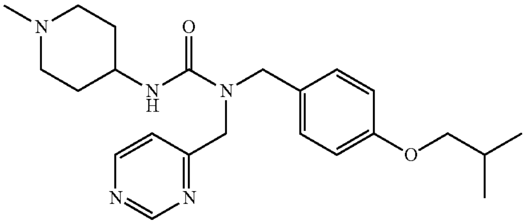 [SMILES: CC(C)COc1ccc(CN(Cc2ccncn2)C(=O)NC2CCN(C)CC2)cc1] | 1 | 1.47 | 412 | |
| I-020 | 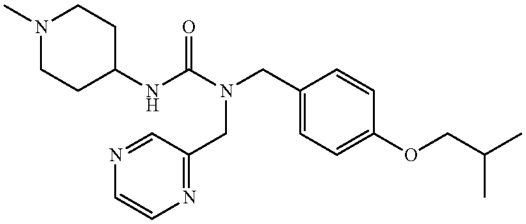 [SMILES: CC(C)COc1ccc(CN(Cc2cnccn2)C(=O)NC2CCN(C)CC2)cc1] | 1 | 1.5 | 412 | |

TABLE 4-continued
| Compound No. | Structural formula | LC/MS Measurement condition | Retention time (min) | m/z | Configuration |
|---|---|---|---|---|---|
| I-021 | 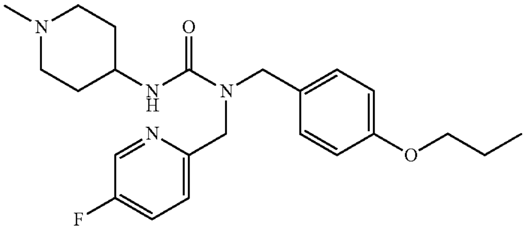 [SMILES: CCCOc1ccc(CN(Cc2ccc(F)cn2)C(=O)NC2CCN(C)CC2)cc1] | 2 | 1.57 | 415 | |
| I-022 | 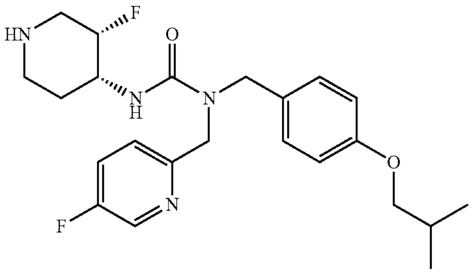 [SMILES: CC(C)COc1ccc(CN(Cc2ccc(F)cn2)C(=O)N[C@@H]2CCNC[C@@H]2F)cc1] | 1 | 1.33 | 433 | b |
| I-023 | 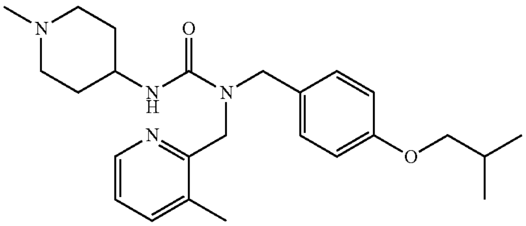 [SMILES: Cc1cccnc1CN(Cc1ccc(OCC(C)C)cc1)C(=O)NC1CCN(C)CC1] | 1 | 1.28 | 425 | |
| I-024 | 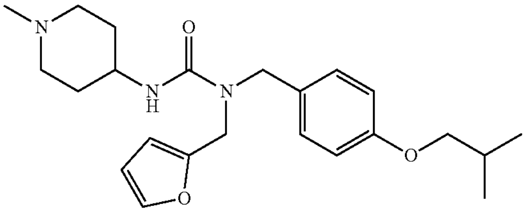 [SMILES: CC(C)COc1ccc(CN(Cc2ccco2)C(=O)NC2CCN(C)CC2)cc1] | 1 | 1.76 | 400 | |
TABLE 5
| Compound No. | Structural formula | LC/MS Measurement condition | Retention time (min) | m/z | Configuration |
|---|---|---|---|---|---|
| I-025 | 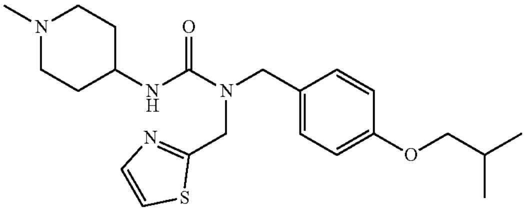 [SMILES: CC(C)COc1ccc(CN(Cc2nccs2)C(=O)NC2CCN(C)CC2)cc1] | 1 | 1.61 | 417 | |

TABLE 5-continued
| Compound No. | Structural formula | LC/MS Measurement condition | Retention time (min) | m/z | Configuration |
|---|---|---|---|---|---|
| I-026 | 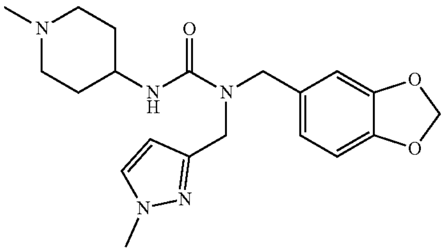 [SMILES: CN1CCC(NC(=O)N(Cc2ccc3c(c2)OCO3)Cc2ccn(C)n2)CC1] | 1 | 1.57 | 386 | |
| I-027 | 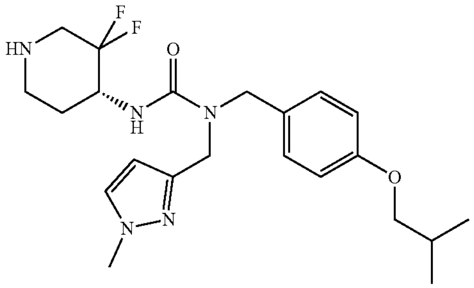 [SMILES: CC(C)COc1ccc(CN(Cc2ccn(C)n2)C(=O)N[C@@H]2CCNCC2(F)F)cc1] | 1 | 1.29 | 436 | c |
| I-028 | 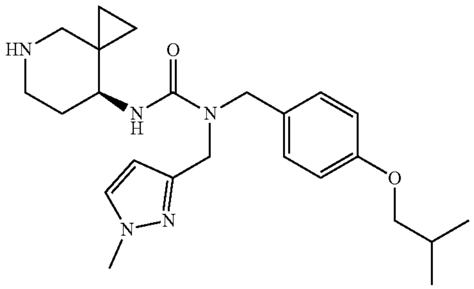 [SMILES: CC(C)COc1ccc(CN(Cc2ccn(C)n2)C(=O)N[C@H]2CCNCC23CC3)cc1] | 1 | 1.51 | 426 | c |
| I-029 | 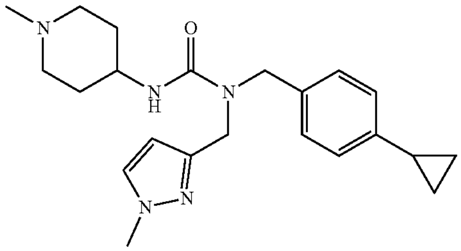 [SMILES: CN1CCC(NC(=O)N(Cc2ccc(C3CC3)cc2)Cc2ccn(C)n2)CC1] | 1 | 1.25 | 382 | |
| I-030 | 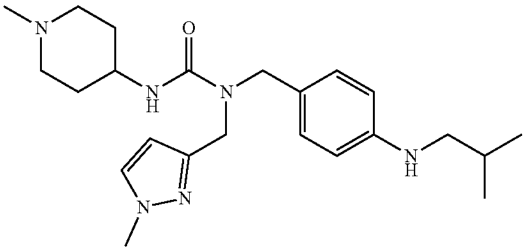 [SMILES: CC(C)CNc1ccc(CN(Cc2ccn(C)n2)C(=O)NC2CCN(C)CC2)cc1] | 1 | 0.9 | 414 | |

TABLE 6
| Compound No. | Structural formula | LC/MS Measurement condition | Retention time (min) | m/z | Configuration |
|---|---|---|---|---|---|
| I-031 | 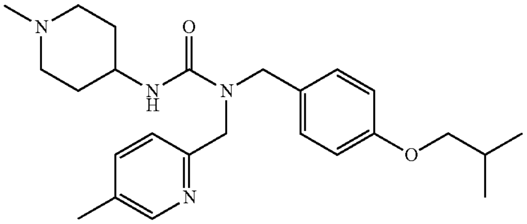 [SMILES: Cc1ccc(CN(Cc2ccc(OCC(C)C)cc2)C(=O)NC2CCN(C)CC2)nc1] | 1 | 1.34 | 425 | |
| I-032 | 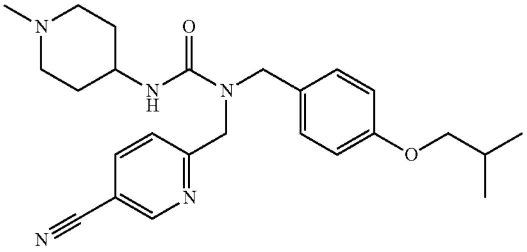 [SMILES: CC(C)COc1ccc(CN(Cc2ccc(C#N)cn2)C(=O)NC2CCN(C)CC2)cc1] | 1 | 1.66 | 436 | |
| I-033 | 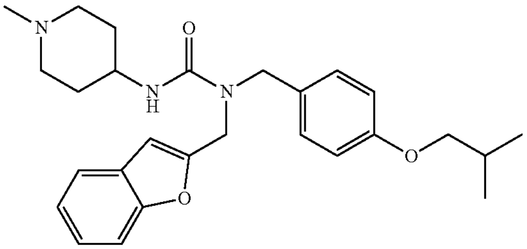 [SMILES: CC(C)COc1ccc(CN(Cc2cc3ccccc3o2)C(=O)NC2CCN(C)CC2)cc1] | 1 | 1.96 | 450 | |
| I-034 | 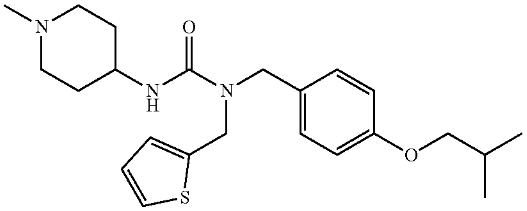 | 1 | 1.82 | 416 | |
| I-035 | 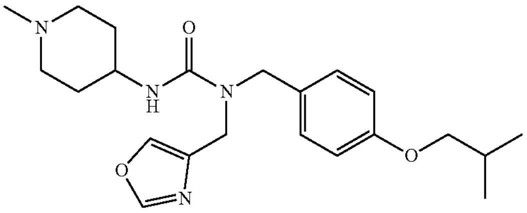 [SMILES: CC(C)COc1ccc(CN(Cc2cocn2)C(=O)NC2CCN(C)CC2)cc1] | 1 | 1.57 | 401 | |
| I-036 | 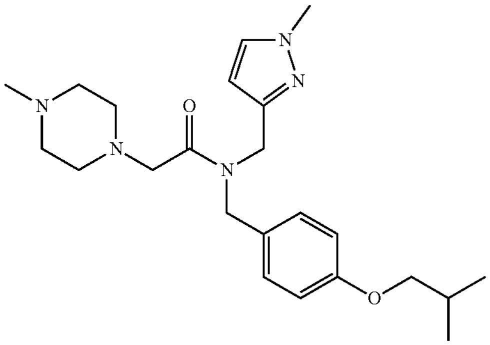 [SMILES: CC(C)COc1ccc(CN(Cc2ccn(C)n2)C(=O)CN2CCN(C)CC2)cc1] | 1 | 1.16 | 414 | |

TABLE 7
| Compound No. | Structural formula | LC/MS Measurement condition | Retention time (min) | m/z | Configuration |
|---|---|---|---|---|---|
| I-037 | 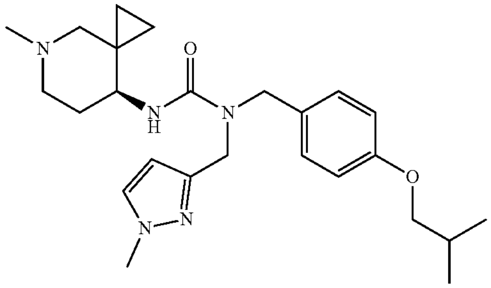 [SMILES: CC(C)COc1ccc(CN(Cc2ccn(C)n2)C(=O)N[C@H]2CCN(C)CC23CC3)cc1] | 1 | 1.44 | 440 | c |
| I-038 | 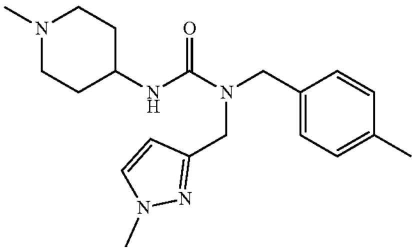 | 1 | 1.03 | 356 | |
| I-039 | 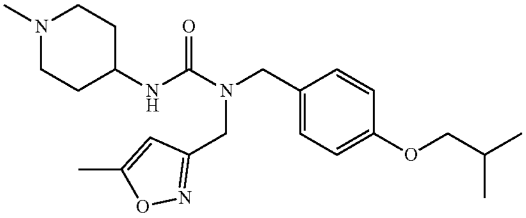 [SMILES: Cc1cc(CN(Cc2ccc(OCC(C)C)cc2)C(=O)NC2CCN(C)CC2)no1] | 1 | 1.67 | 415 | |
| I-040 | 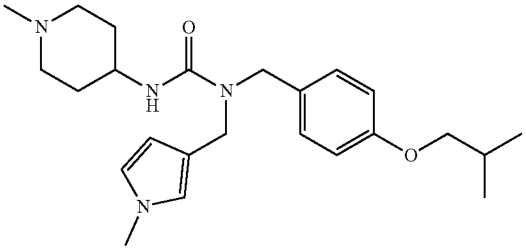 [SMILES: CC(C)COc1ccc(CN(Cc2ccn(C)c2)C(=O)NC2CCN(C)CC2)cc1] | 1 | 1.76 | 413 | |
| I-041 | 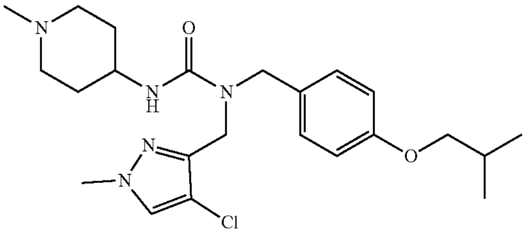 [SMILES: CC(C)COc1ccc(CN(Cc2nn(C)cc2Cl)C(=O)NC2CCN(C)CC2)cc1] | 1 | 1.75 | 448 | |
| I-042 | 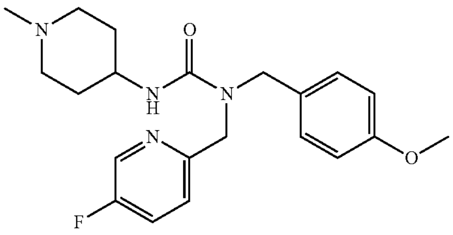 | 2 | 1.31 | 387 | |

TABLE 8
| Compound No. | Structural formula | LC/MS Measurement condition | Retention time (min) | m/z | Configuration |
|---|---|---|---|---|---|
| I-043 | 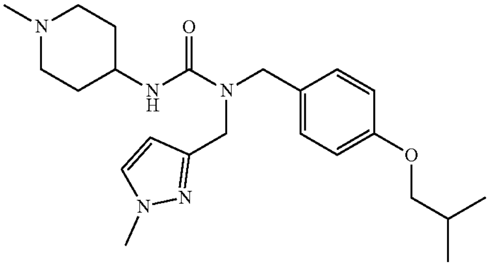 [SMILES: CC(C)COc1ccc(CN(Cc2ccn(C)n2)C(=O)NC2CCN(C)CC2)cc1] | 1 | 1.22 | 414 | |
| I-044 | 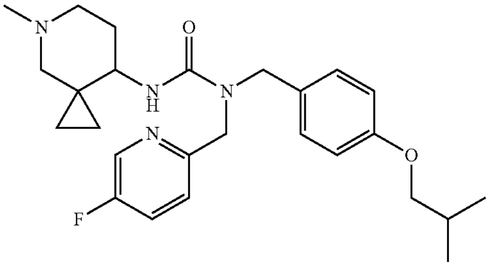 [SMILES: CC(C)COc1ccc(CN(Cc2ccc(F)cn2)C(=O)NC2CCN(C)CC23CC3)cc1] | 1 | 1.37 | 455 | d |
| I-045 | 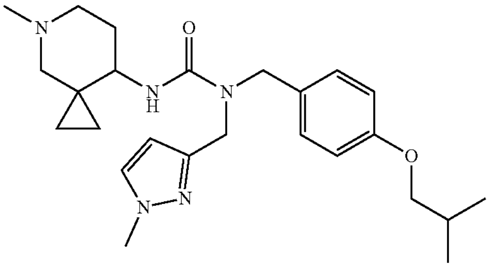 [SMILES: CC(C)COc1ccc(CN(Cc2ccn(C)n2)C(=O)NC2CCN(C)CC23CC3)cc1] | 1 | 1.23 | 440 | d |
| I-046 | 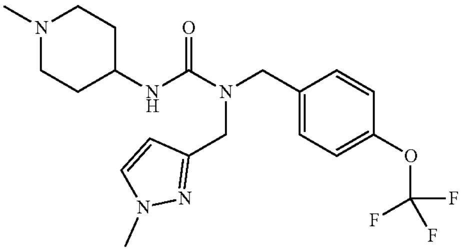 [SMILES: CN1CCC(NC(=O)N(Cc2ccc(OC(F)(F)F)cc2)Cc2ccn(C)n2)CC1] | 1 | 1.95 | 426 | |
| I-047 | 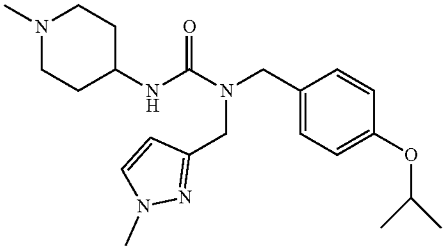 [SMILES: CC(C)Oc1ccc(CN(Cc2ccn(C)n2)C(=O)NC2CCN(C)CC2)cc1] | 1 | 1.84 | 400 | |

TABLE 8-continued
| Compound No. | Structural formula | LC/MS Measurement condition | Retention time (min) | m/z | Configuration |
|---|---|---|---|---|---|
| I-048 | 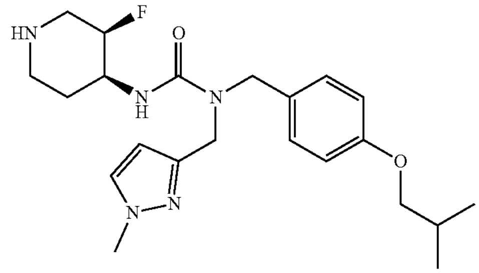 [SMILES: CC(C)COc1ccc(CN(Cc2ccn(C)n2)C(=O)N[C@H]2CCNC[C@H]2F)cc1] | 1 | 1.29 | 418 | c |
TABLE 9
| Compound No. | Structural formula | LC/MS Measurement condition | Retention time (min) | m/z | Configuration |
|---|---|---|---|---|---|
| I-049 | 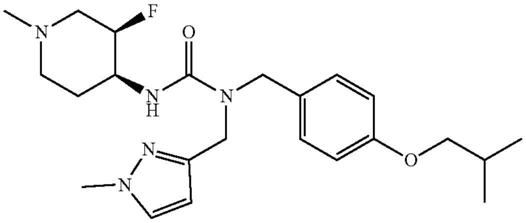 [SMILES: CC(C)COc1ccc(CN(Cc2ccn(C)n2)C(=O)N[C@H]2CCN(C)C[C@H]2F)cc1] | 1 | 1.3 | 432 | c |
| I-050 | 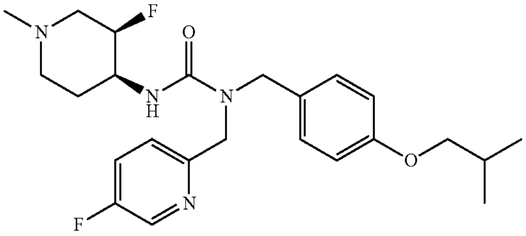 [SMILES: CC(C)COc1ccc(CN(Cc2ccc(F)cn2)C(=O)N[C@H]2CCN(C)C[C@H]2F)cc1] | 1 | 1.37 | 447 | c |
| I-051 | 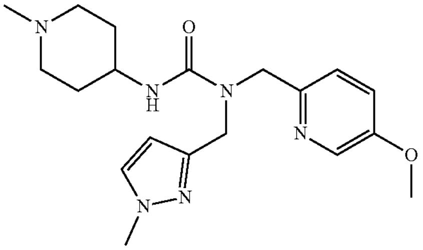 | 1 | 1.38 | 373 | |
| I-052 | 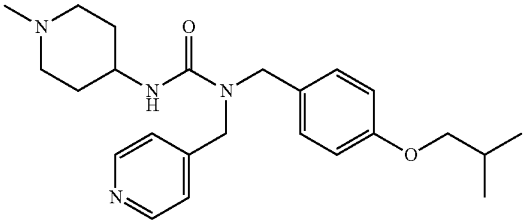 [SMILES: CC(C)COc1ccc(CN(Cc2ccncc2)C(=O)NC2CCN(C)CC2)cc1] | 1 | 1.17 | 411 | |

TABLE 9-continued
| Compound No. | Structural formula | LC/MS Measurement condition | Retention time (min) | m/z | Configuration |
|---|---|---|---|---|---|
| I-053 | 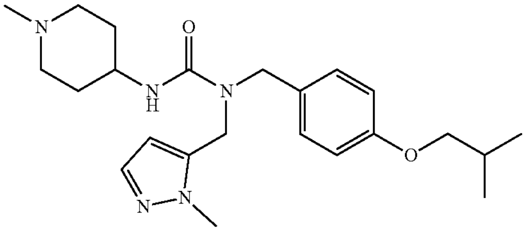 [SMILES: CC(C)COc1ccc(CN(Cc2ccnn2C)C(=O)NC2CCN(C)CC2)cc1] | 1 | 1.54 | 414 | |
| I-054 | 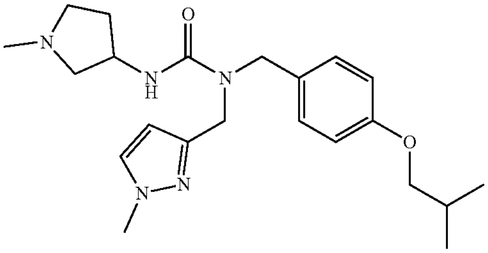 [SMILES: CC(C)COc1ccc(CN(Cc2ccn(C)n2)C(=O)NC2CCN(C)C2)cc1] | 1 | 1.2 | 400 | d |
TABLE 10
| Compound No. | Structural formula | LC/MS Measurement condition | Retention time (min) | m/z | Configuration |
|---|---|---|---|---|---|
| I-055 | 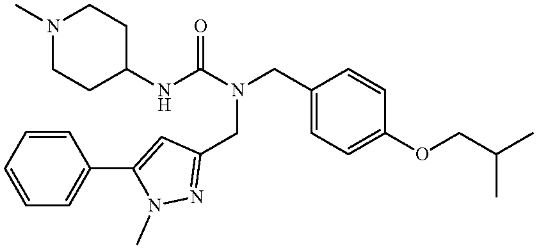 [SMILES: CC(C)COc1ccc(CN(Cc2cc(-c3ccccc3)n(C)n2)C(=O)NC2CCN(C)CC2)cc1] | 1 | 1.91 | 490 | |
| I-056 | 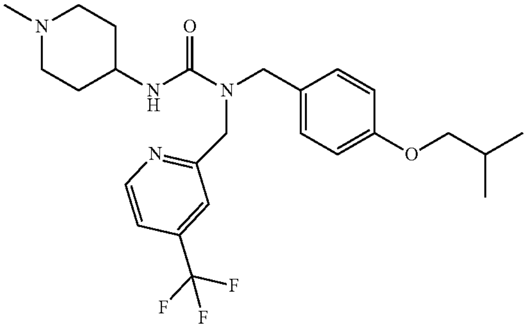 [SMILES: CC(C)COc1ccc(CN(Cc2cc(C(F)(F)F)ccn2)C(=O)NC2CCN(C)CC2)cc1] | 1 | 1.83 | 479 | |
| I-057 | 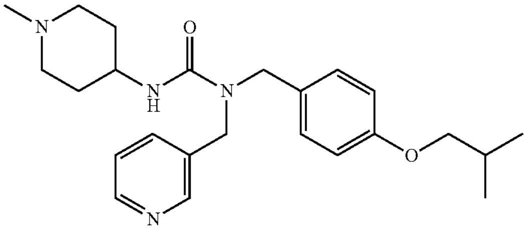 [SMILES: CC(C)COc1ccc(CN(Cc2cccnc2)C(=O)NC2CCN(C)CC2)cc1] | 1 | 1.21 | 411 | |

TABLE 11
| Compound No. | Structural formula | LC/MS Measurement condition | Retention time (min) | m/z | Configuration |
|---|---|---|---|---|---|
| I-058 | 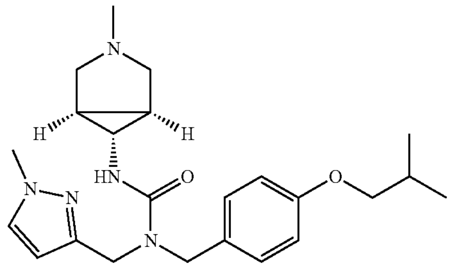 [SMILES: CC(C)COc1ccc(CN(Cc2ccn(C)n2)C(=O)N[C@H]2[C@@H]3CN(C)C[C@@H]32)cc1] | 1 | 1.51 | 412 | c |
| I-059 | 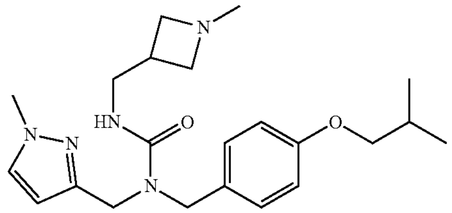 [SMILES: CC(C)COc1ccc(CN(Cc2ccn(C)n2)C(=O)NCC2CN(C)C2)cc1] | 2 | 1.48 | 400 | |
| I-060 | 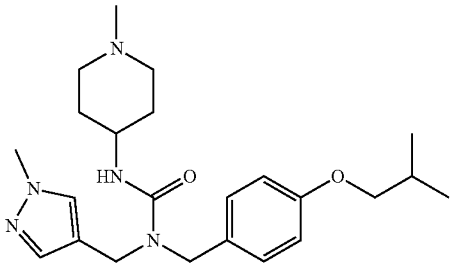 [SMILES: CC(C)COc1ccc(CN(Cc2cnn(C)c2)C(=O)NC2CCN(C)CC2)cc1] | 1 | 1.19 | 414 | |
| I-061 | 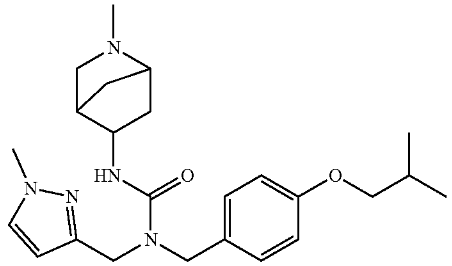 [SMILES: CC(C)COc1ccc(CN(Cc2ccn(C)n2)C(=O)NC2CC3CC2CN3C)cc1] | 1 | 1.5 | 426 | e |
| I-062 | 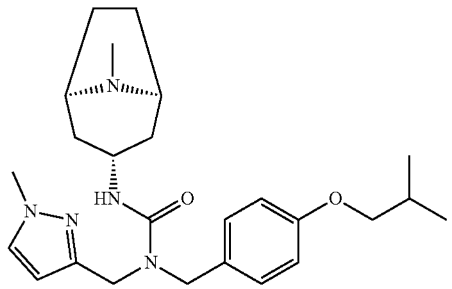 [SMILES: CC(C)COc1ccc(CN(Cc2ccn(C)n2)C(=O)N[C@@H]2C[C@H]3CC[C@@H](C2)N3C)cc1] | 1 | 1.41 | 440 | c |

TABLE 11-continued
| Compound No. | Structural formula | LC/MS Measurement condition | Retention time (min) | m/z | Configuration |
|---|---|---|---|---|---|
| I-063 | 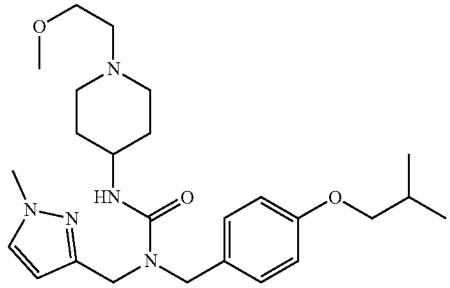 [SMILES: COCCN1CCC(NC(=O)N(Cc2ccc(OCC(C)C)cc2)Cc2ccn(C)n2)CC1] | 2 | 1.59 | 458 | |
TABLE 12
| Compound No. | Structural formula | LC/MS Measurement condition | Retention time (min) | m/z | Configuration |
|---|---|---|---|---|---|
| I-064 | 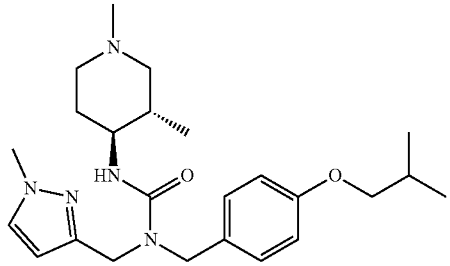 [SMILES: CC(C)COc1ccc(CN(Cc2ccn(C)n2)C(=O)N[C@H]2CCN(C)C[C@@H]2C)cc1] | 2 | 1.58 | 428 | c |
| I-065 | 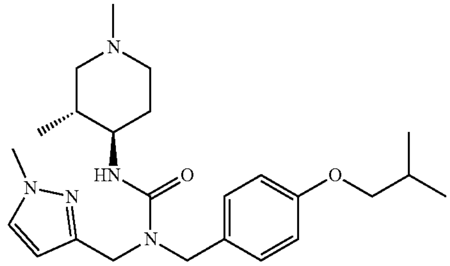 [SMILES: CC(C)COc1ccc(CN(Cc2ccn(C)n2)C(=O)N[C@@H]2CCN(C)C[C@H]2C)cc1] | 2 | 1.58 | 428 | c |
| I-066 | 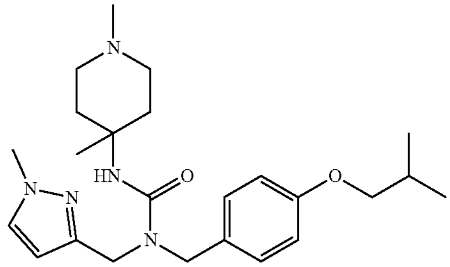 [SMILES: CC(C)COc1ccc(CN(Cc2ccn(C)n2)C(=O)NC2(C)CCN(C)CC2)cc1] | 2 | 1.6 | 428 | |

TABLE 12-continued
| Compound No. | Structural formula | LC/MS Measurement condition | Retention time (min) | m/z | Configuration |
|---|---|---|---|---|---|
| I-067 | 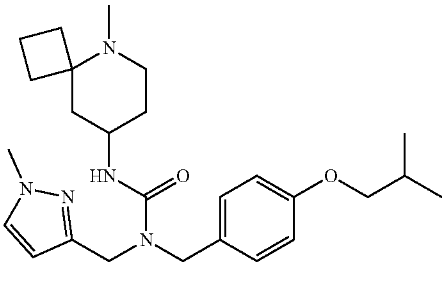 [SMILES: CC(C)COc1ccc(CN(Cc2ccn(C)n2)C(=O)NC2CCN(C)C3(CCC3)C2)cc1] | 2 | 1.64 | 454 | d |
| I-068 | 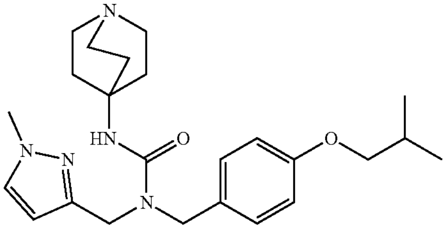 [SMILES: CC(C)COc1ccc(CN(Cc2ccn(C)n2)C(=O)NC23CCN(CC2)CC3)cc1] | 1 | 1.635 | 426.3 | |
| I-069 | 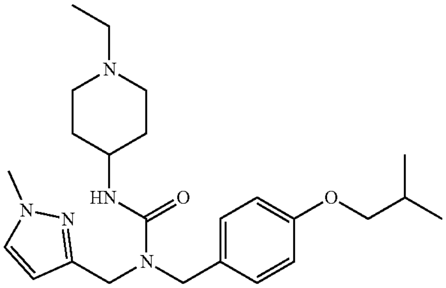 [SMILES: CCN1CCC(NC(=O)N(Cc2ccc(OCC(C)C)cc2)Cc2ccn(C)n2)CC1] | 1 | 1.595 | 428.3 | |
TABLE 13
| Compound No. | Structural formula | LC/MS Measurement condition | Retention time (min) | m/z | Configuration |
|---|---|---|---|---|---|
| I-070 | 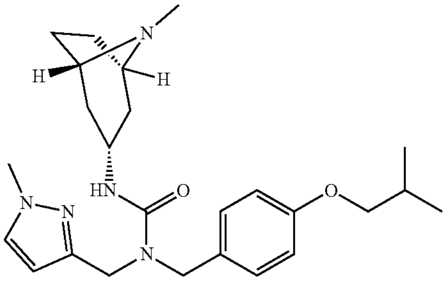 [SMILES: CC(C)COc1ccc(CN(Cc2ccn(C)n2)C(=O)N[C@H]2C[C@H]3CC[C@@H](C2)N3C)cc1] | 1 | 1.67 | 440.2 | c |

TABLE 13-continued
| Compound No. | Structural formula | LC/MS Measurement condition | Retention time (min) | m/z | Configuration |
|---|---|---|---|---|---|
| I-071 | 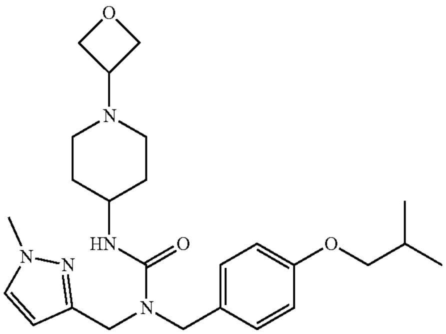 [SMILES: CC(C)COc1ccc(CN(Cc2ccn(C)n2)C(=O)NC2CCN(C3COC3)CC2)cc1] | 1 | 1.585 | 456.3 | |
| I-072 | 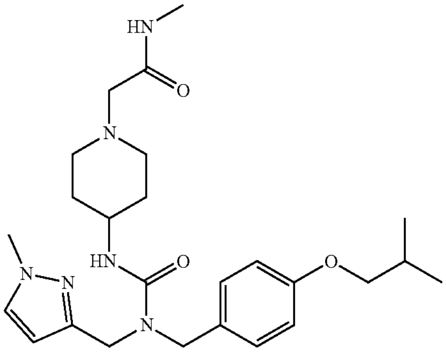 [SMILES: CNC(=O)CN1CCC(NC(=O)N(Cc2ccc(OCC(C)C)cc2)Cc2ccn(C)n2)CC1] | 1 | 1.567 | 471.3 | |
| I-073 | 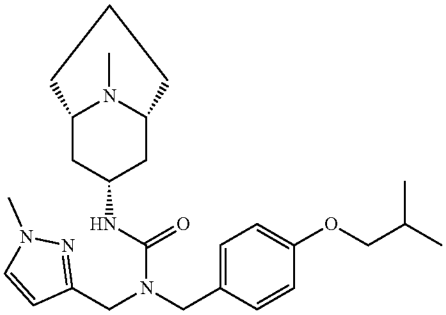 [SMILES: CC(C)COc1ccc(CN(Cc2ccn(C)n2)C(=O)N[C@H]2C[C@H]3CCC[C@@H](C2)N3C)cc1] | 1 | 1.718 | 454.3 | c |
| I-074 | 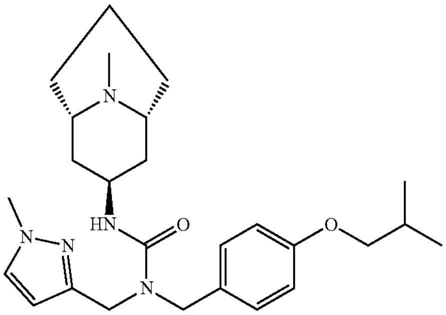 [SMILES: CC(C)COc1ccc(CN(Cc2ccn(C)n2)C(=O)N[C@@H]2C[C@H]3CCC[C@@H](C2)N3C)cc1] | 1 | 1.682 | 454.3 | c |

TABLE 14
| Compound No. | Structural formula | LC/MS Measurement condition | Retention time (min) | m/z | Configuration |
|---|---|---|---|---|---|
| I-075 | 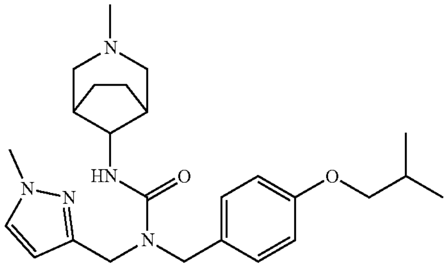 [SMILES: CC(C)COc1ccc(CN(Cc2ccn(C)n2)C(=O)NC2C3CCC2CN(C)C3)cc1] | 1 | 1.635 | 440.2 | f |
| I-076 | 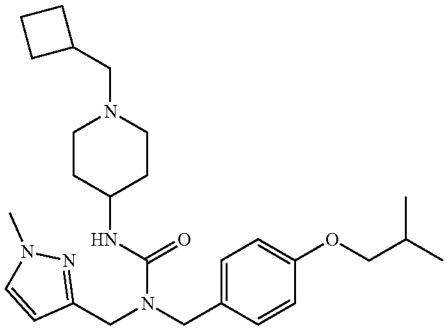 [SMILES: CC(C)COc1ccc(CN(Cc2ccn(C)n2)C(=O)NC2CCN(CC3CCC3)CC2)cc1] | 1 | 1.52 | 468 | |
| I-077 | 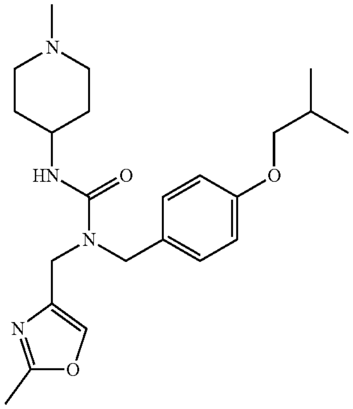 [SMILES: Cc1nc(CN(Cc2ccc(OCC(C)C)cc2)C(=O)NC2CCN(C)CC2)co1] | 1 | 1.57 | 415.2 | |
| I-078 | 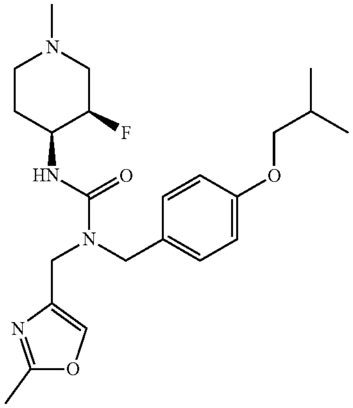 [SMILES: Cc1nc(CN(Cc2ccc(OCC(C)C)cc2)C(=O)N[C@H]2CCN(C)C[C@H]2F)co1] | 1 | 1.59 | 433.2 | c |

TABLE 14-continued
| Compound No. | Structural formula | LC/MS Measurement condition | Retention time (min) | m/z | Configuration |
|---|---|---|---|---|---|
| I-079 | 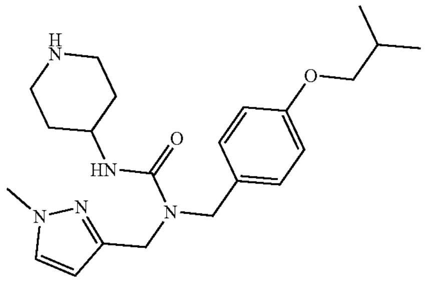 [SMILES: CC(C)COc1ccc(CN(Cc2ccn(C)n2)C(=O)NC2CCNCC2)cc1] | 1 | 1.38 | 400 | |
TABLE 15
| Compound No. | Structural formula | LC/MS Measurement condition | Retention time (min) | m/z | Configuration |
|---|---|---|---|---|---|
| I-080 | 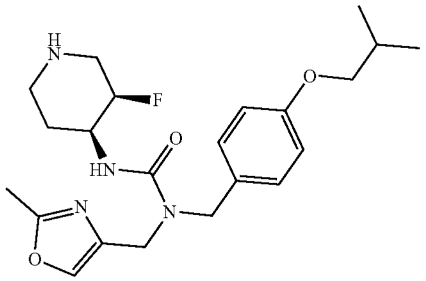 [SMILES: Cc1nc(CN(Cc2ccc(OCC(C)C)cc2)C(=O)N[C@H]2CCNC[C@H]2F)co1] | 1 | 1.42 | 419 | c |
| I-081 | 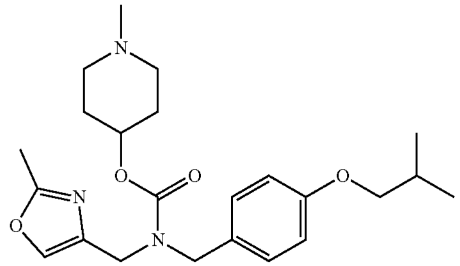 [SMILES: Cc1nc(CN(Cc2ccc(OCC(C)C)cc2)C(=O)OC2CCN(C)CC2)co1] | 1 | 1.57 | 416 | |
| I-082 | 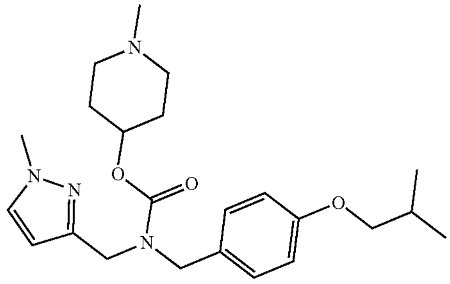 [SMILES: CC(C)COc1ccc(CN(Cc2ccn(C)n2)C(=O)OC2CCN(C)CC2)cc1] | 1 | 1.46 | 415 | |

TABLE 15-continued
| Compound No. | Structural formula | LC/MS Measurement condition | Retention time (min) | m/z | Configuration |
|---|---|---|---|---|---|
| I-083 | 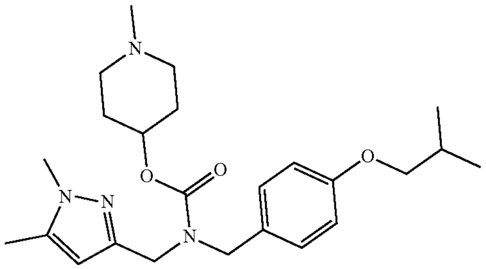 [SMILES: Cc1cc(CN(Cc2ccc(OCC(C)C)cc2)C(=O)OC2CCN(C)CC2)nn1C] | 1 | 1.69 | 429 | |
| I-084 | 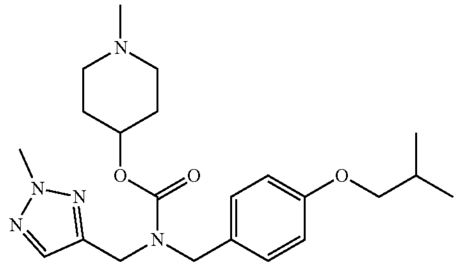 [SMILES: CC(C)COc1ccc(CN(Cc2cnn(C)n2)C(=O)OC2CCN(C)CC2)cc1] | 1 | 1.63 | 416 | |
| I-085 | 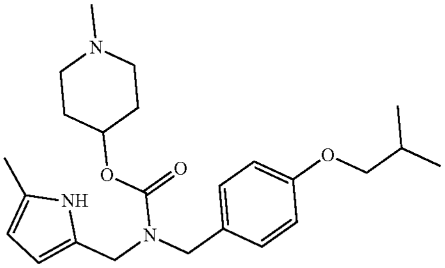 [SMILES: Cc1ccc(CN(Cc2ccc(OCC(C)C)cc2)C(=O)OC2CCN(C)CC2)[nH]1] | 1 | 1.92 | 414 | |
TABLE 16
| Compound No. | Structural formula | LC/MS Measurement condition | Retention time (min) | m/z | Configuration |
|---|---|---|---|---|---|
| I-086 | 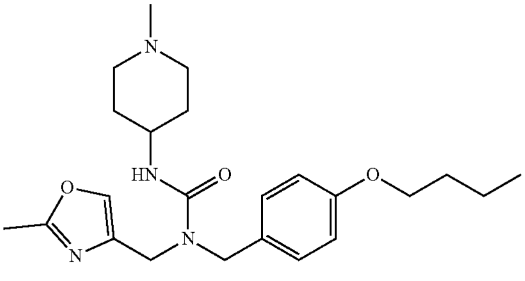 [SMILES: CCCCOc1ccc(CN(Cc2coc(C)n2)C(=O)NC2CCN(C)CC2)cc1] | 1 | 1.34 | 415 | |

TABLE 16-continued
| Compound No. | Structural formula | LC/MS Measurement condition | Retention time (min) | m/z | Configuration |
|---|---|---|---|---|---|
| I-087 | 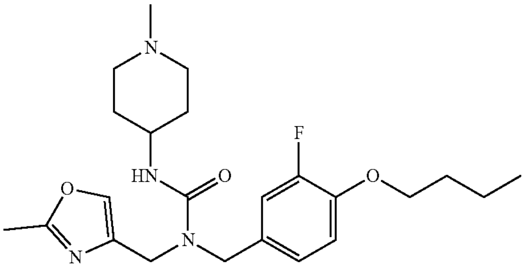 [SMILES: CCCCOc1ccc(CN(Cc2coc(C)n2)C(=O)NC2CCN(C)CC2)cc1F] | 1 | 1.37 | 433 | |
| I-088 | 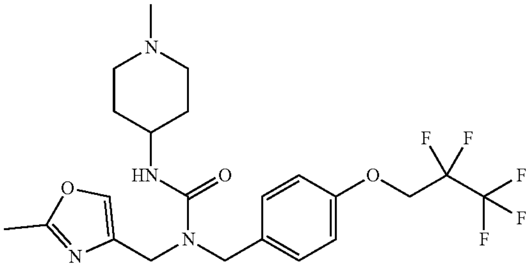 [SMILES: Cc1nc(CN(Cc2ccc(OCC(F)(F)C(F)(F)F)cc2)C(=O)NC2CCN(C)CC2)co1] | 1 | 1.39 | 491 | |
| I-089 | 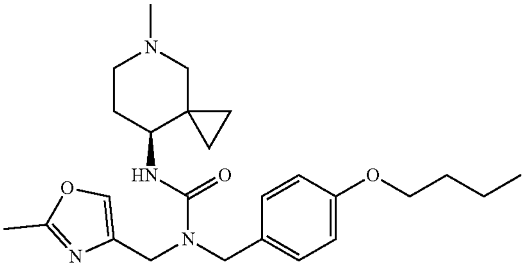 [SMILES: CCCCOc1ccc(CN(Cc2coc(C)n2)C(=O)N[C@H]2CCN(C)CC23CC3)cc1] | 2 | 1.65 | 441 | c |
| I-090 | 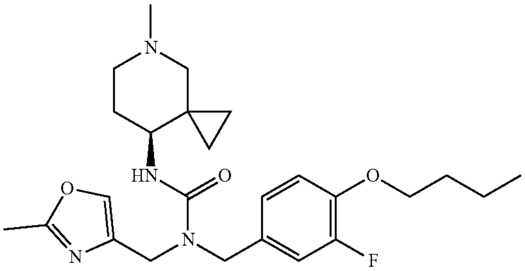 [SMILES: CCCCOc1ccc(CN(Cc2coc(C)n2)C(=O)N[C@H]2CCN(C)CC23CC3)cc1F] | 2 | 1.68 | 459 | c |
| I-091 | 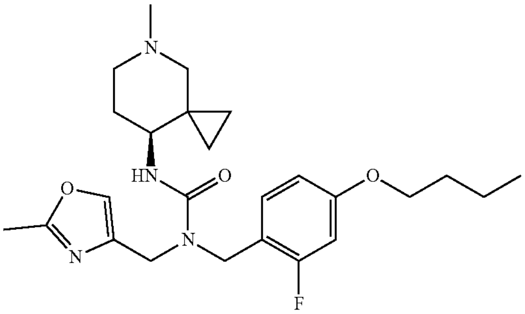 [SMILES: CCCCOc1ccc(CN(Cc2coc(C)n2)C(=O)N[C@H]2CCN(C)CC23CC3)c(F)c1] | 2 | 1.72 | 459 | c |

TABLE 17
| Compound No. | Structural formula | LC/MS Measurement condition | Retention time (min) | m/z | Configuration |
|---|---|---|---|---|---|
| I-092 | 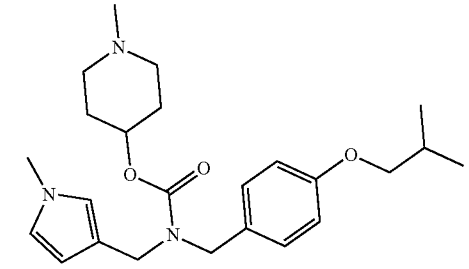 [SMILES: CC(C)COc1ccc(CN(Cc2ccn(C)c2)C(=O)OC2CCN(C)CC2)cc1] | 1 | 1.89 | 414.1 | |
| I-093 | 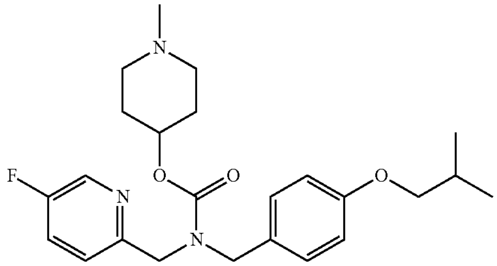 [SMILES: CC(C)COc1ccc(CN(Cc2ccc(F)cn2)C(=O)OC2CCN(C)CC2)cc1] | 2 | 1.77 | 430.1 | |
| I-094 | 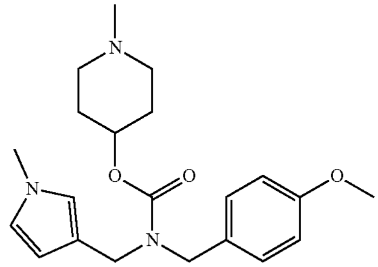 [SMILES: COc1ccc(CN(Cc2ccn(C)c2)C(=O)OC2CCN(C)CC2)cc1] | 2 | 1.49 | 372.1 | |
| I-095 | 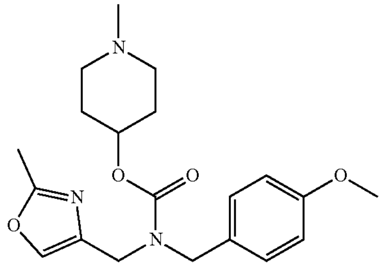 [SMILES: COc1ccc(CN(Cc2coc(C)n2)C(=O)OC2CCN(C)CC2)cc1] | 2 | 1.31 | 374.1 | |
| I-096 | 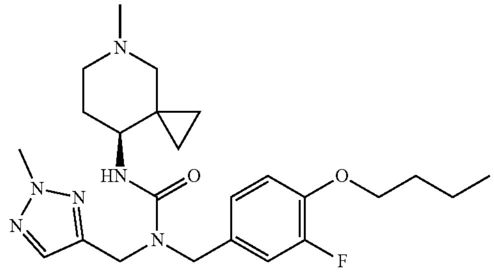 [SMILES: CCCCOc1ccc(CN(Cc2cnn(C)n2)C(=O)N[C@H]2CCN(C)CC23CC3)cc1F] | 1 | 1.39 | 459 | c |

TABLE 17-continued
| Compound No. | Structural formula | LC/MS Measurement condition | Retention time (min) | m/z | Configuration |
|---|---|---|---|---|---|
| I-097 | 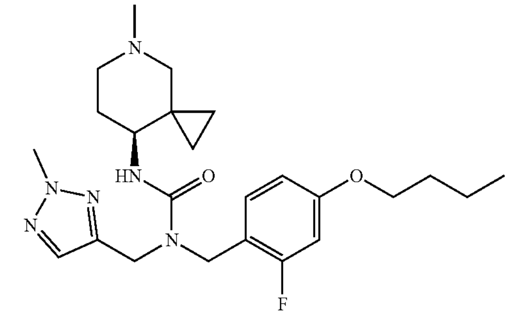 [SMILES: CCCCOc1ccc(CN(Cc2cnn(C)n2)C(=O)N[C@H]2CCN(C)CC23CC3)c(F)c1] | 1 | 1.45 | 459 | c |
TABLE 18
| Compound No. | Structural formula | LC/MS Measurement condition | Retention time (min) | m/z | Configuration |
|---|---|---|---|---|---|
| I-098 | 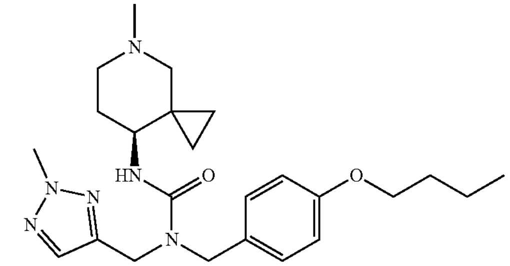 [SMILES: CCCCOc1ccc(CN(Cc2cnn(C)n2)C(=O)N[C@H]2CCN(C)CC23CC3)cc1] | 1 | 1.38 | 441 | c |
| I-099 | 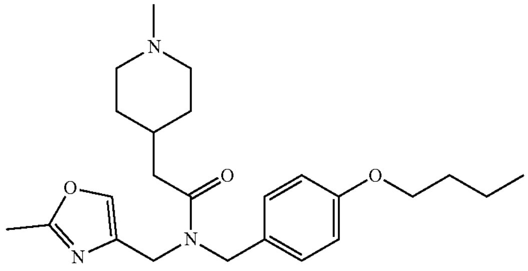 [SMILES: CCCCOc1ccc(CN(Cc2coc(C)n2)C(=O)CC2CCN(C)CC2)cc1] | 2 | 1.64 | 414 | |
| I-100 | 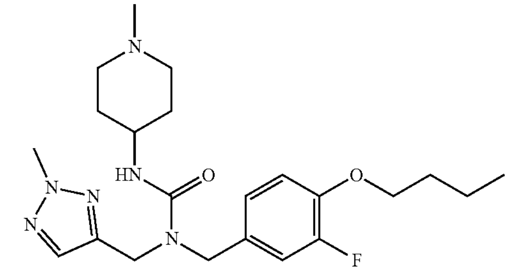 [SMILES: CCCCOc1ccc(CN(Cc2cnn(C)n2)C(=O)NC2CCN(C)CC2)cc1F] | 1 | 1.36 | 433.15 | |

TABLE 18-continued
| Compound No. | Structural formula | LC/MS Measurement condition | Retention time (min) | m/z | Configuration |
|---|---|---|---|---|---|
| I-101 | 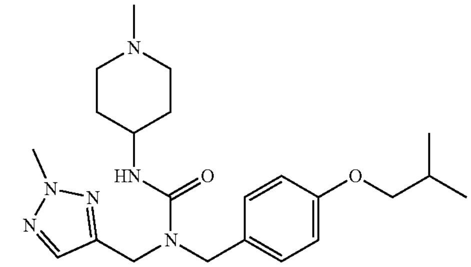 [SMILES: CC(C)COc1ccc(CN(Cc2cnn(C)n2)C(=O)NC2CCN(C)CC2)cc1] | 1 | 1.34 | 415.1 | |
| I-102 | 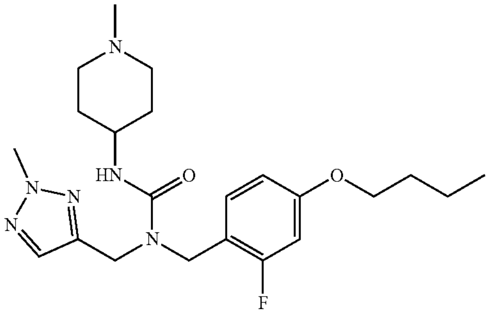 [SMILES: CCCCOc1ccc(CN(Cc2cnn(C)n2)C(=O)NC2CCN(C)CC2)c(F)c1] | 1 | 1.39 | 433.1 | |
| I-103 | 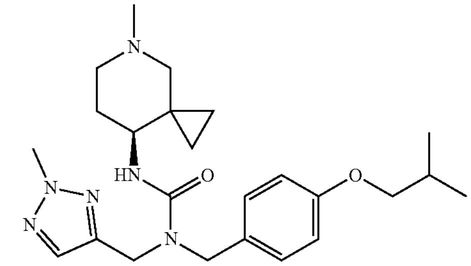 [SMILES: CC(C)COc1ccc(CN(Cc2cnn(C)n2)C(=O)N[C@H]2CCN(C)CC23CC3)cc1] | 1 | 1.34 | 441 | c |
TABLE 19
| Compound No. | Structural formula | LC/MS Measurement condition | Retention time (min) | m/z | Configuration |
|---|---|---|---|---|---|
| I-104 | 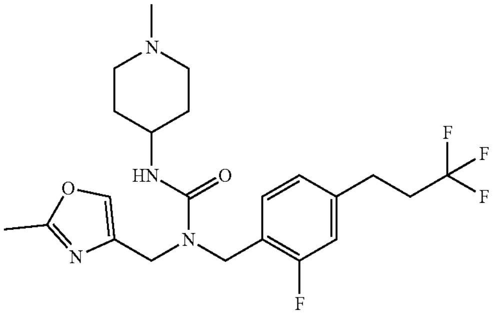 [SMILES: Cc1nc(CN(Cc2ccc(CCC(F)(F)F)cc2F)C(=O)NC2CCN(C)CC2)co1] | 2 | 1.6 | 457.2 | |

TABLE 19-continued
| Compound No. | Structural formula | LC/MS Measurement condition | Retention time (min) | m/z | Configuration |
|---|---|---|---|---|---|
| I-105 | 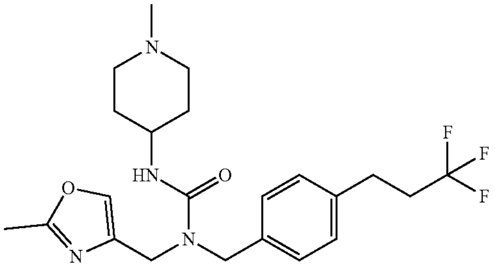 [SMILES: Cc1nc(CN(Cc2ccc(CCC(F)(F)F)cc2)C(=O)NC2CCN(C)CC2)co1] | 2 | 1.55 | 439.2 | |
| I-106 | 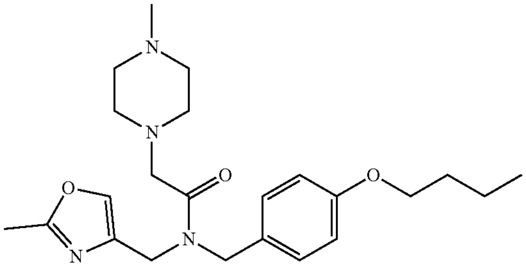 [SMILES: CCCCOc1ccc(CN(Cc2coc(C)n2)C(=O)CN2CCN(C)CC2)cc1] | 1 | 1.38 | 415 | |
| I-107 | 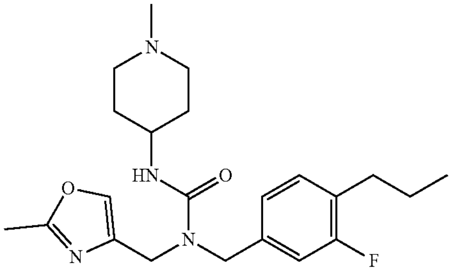 [SMILES: CCCc1ccc(CN(Cc2coc(C)n2)C(=O)NC2CCN(C)CC2)cc1F] | 2 | 1.36 | 403 | |
| I-108 | 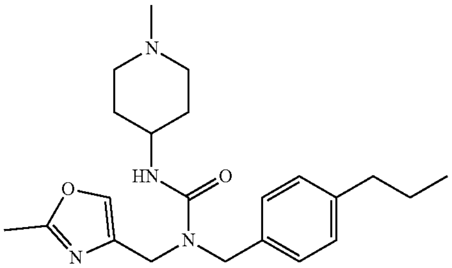 [SMILES: CCCc1ccc(CN(Cc2coc(C)n2)C(=O)NC2CCN(C)CC2)cc1] | 2 | 1.58 | 385 | |
| I-109 | 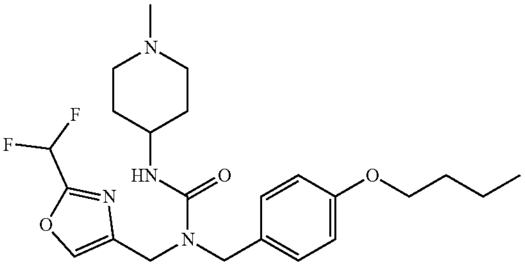 [SMILES: CCCCOc1ccc(CN(Cc2coc(C(F)F)n2)C(=O)NC2CCN(C)CC2)cc1] | 1 | 1.49 | 451.1 | |

TABLE 20
| Compound No. | Structural formula | LC/MS Measurement condition | Retention time (min) | m/z | Configuration |
|---|---|---|---|---|---|
| I-110 | 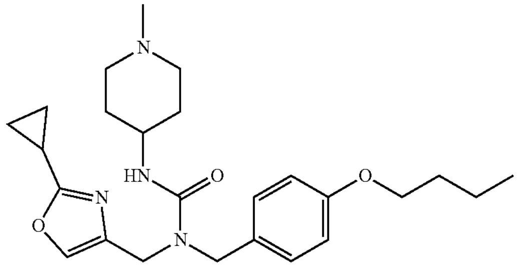 [SMILES: CCCCOc1ccc(CN(Cc2coc(C3CC3)n2)C(=O)NC2CCN(C)CC2)cc1] | 1 | 1.55 | 441.15 | |
| I-111 | 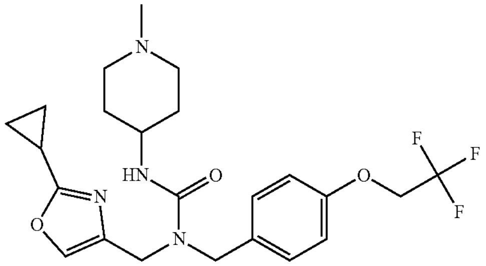 [SMILES: CN1CCC(NC(=O)N(Cc2ccc(OCC(F)(F)F)cc2)Cc2coc(C3CC3)n2)CC1] | 1 | 1.37 | 467.1 | |
| I-112 | 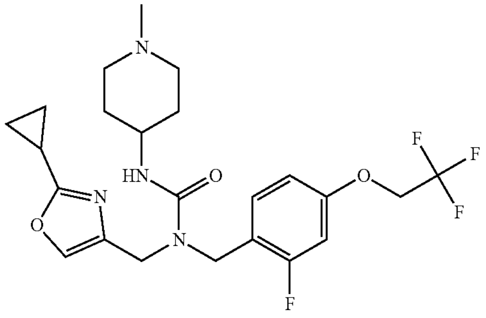 [SMILES: CN1CCC(NC(=O)N(Cc2coc(C3CC3)n2)Cc2ccc(OCC(F)(F)F)cc2F)CC1] | 1 | 1.41 | 485.3 | |
| I-113 | 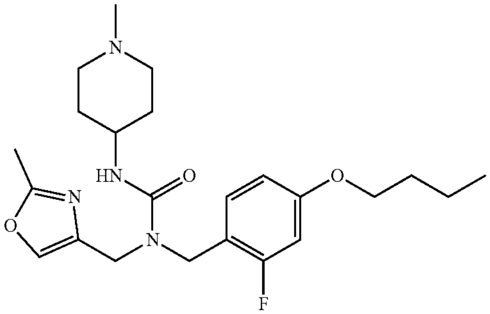 [SMILES: CCCCOc1ccc(CN(Cc2coc(C)n2)C(=O)NC2CCN(C)CC2)c(F)c1] | 1 | 1.47 | 433.1 | |
| I-114 | 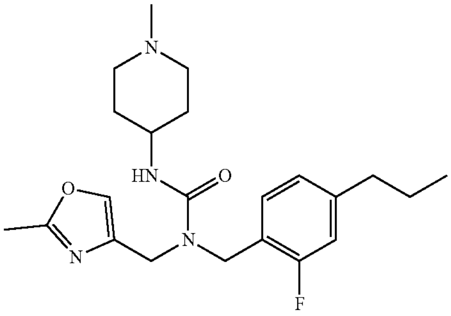 [SMILES: CCCc1ccc(CN(Cc2coc(C)n2)C(=O)NC2CCN(C)CC2)c(F)c1] | 2 | 1.59 | 403.3 | |

TABLE 20-continued
| Compound No. | Structural formula | LC/MS Measurement condition | Retention time (min) | m/z | Configuration |
|---|---|---|---|---|---|
| I-115 | 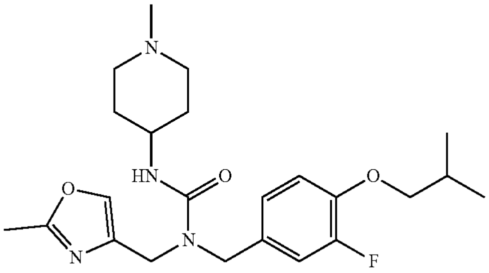 [SMILES: Cc1nc(CN(Cc2ccc(OCC(C)C)c(F)c2)C(=O)NC2CCN(C)CC2)co1] | 2 | 1.82 | 433 | |
TABLE 21
| Compound No. | Structural formula | LC/MS Measurement condition | Retention time (min) | m/z | Configuration |
|---|---|---|---|---|---|
| I-116 | 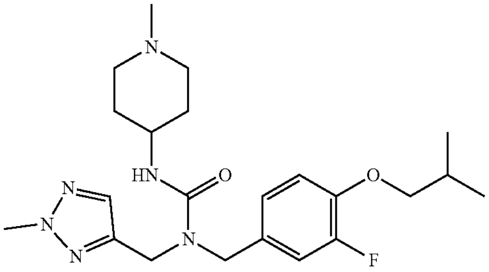 [SMILES: CC(C)COc1ccc(CN(Cc2cnn(C)n2)C(=O)NC2CCN(C)CC2)cc1F] | 2 | 1.77 | 433 | |
| I-117 | 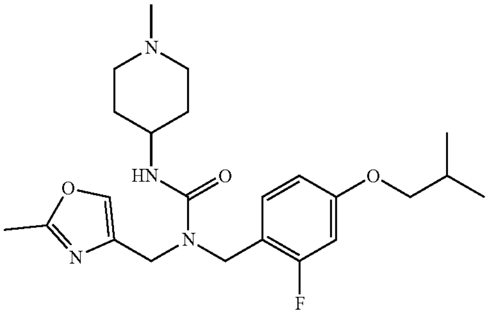 [SMILES: Cc1nc(CN(Cc2ccc(OCC(C)C)cc2F)C(=O)NC2CCN(C)CC2)co1] | 2 | 1.86 | 433 | |
| I-118 | 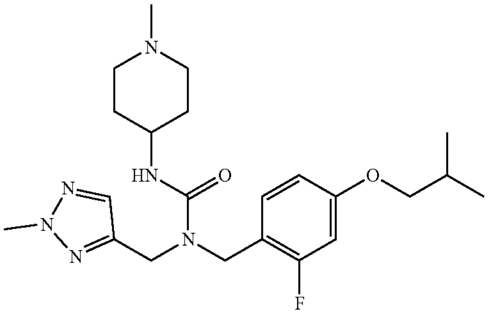 [SMILES: CC(C)COc1ccc(CN(Cc2cnn(C)n2)C(=O)NC2CCN(C)CC2)c(F)c1] | 2 | 1.75 | 433 | |

TABLE 21-continued
| Compound No. | Structural formula | LC/MS Measurement condition | Retention time (min) | m/z | Configuration |
|---|---|---|---|---|---|
| I-119 | 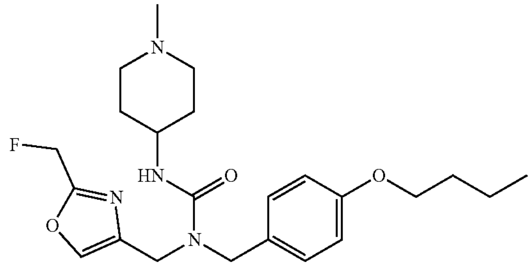 [SMILES: CCCCOc1ccc(CN(Cc2coc(CF)n2)C(=O)NC2CCN(C)CC2)cc1] | 1 | 1.42 | 433.35 | |
| I-120 | 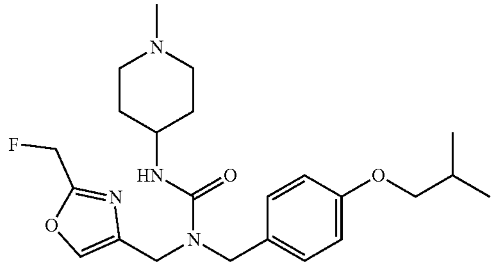 [SMILES: CC(C)COc1ccc(CN(Cc2coc(CF)n2)C(=O)NC2CCN(C)CC2)cc1] | 1 | 1.42 | 433.1 | |
| I-121 | 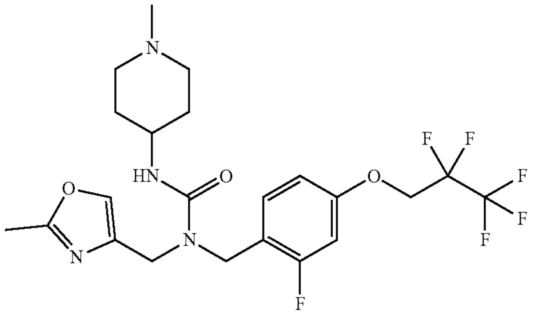 [SMILES: Cc1nc(CN(Cc2ccc(OCC(F)(F)C(F)(F)F)cc2F)C(=O)NC2CCN(C)CC2)co1] | 2 | 1.73 | 509.2 | |
TABLE 22
| Compound No. | Structural formula | LC/MS Measurement condition | Retention time (min) | m/z | Configuration |
|---|---|---|---|---|---|
| I-122 | 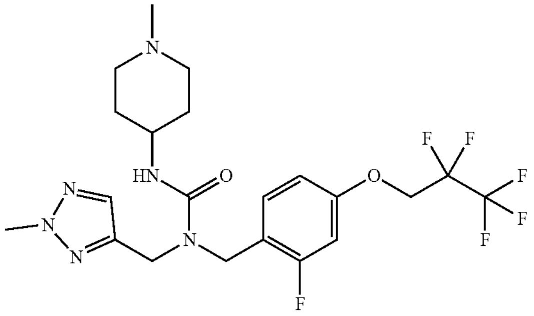 [SMILES: CN1CCC(NC(=O)N(Cc2cnn(C)n2)Cc2ccc(OCC(F)(F)C(F)(F)F)cc2F)CC1] | 2 | 1.68 | 509.25 | |

TABLE 22-continued
| Compound No. | Structural formula | LC/MS Measurement condition | Retention time (min) | m/z | Configuration |
|---|---|---|---|---|---|
| I-123 | 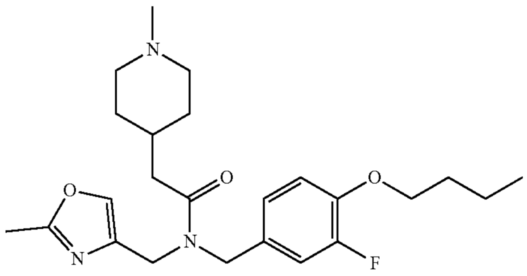 [SMILES: CCCCOc1ccc(CN(Cc2coc(C)n2)C(=O)CC2CCN(C)CC2)cc1F] | 2 | 1.67 | 432 | |
| I-124 | 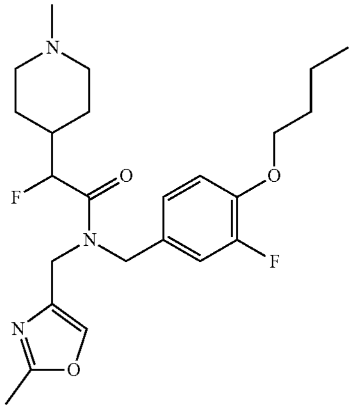 [SMILES: CCCCOc1ccc(CN(Cc2coc(C)n2)C(=O)C(F)C2CCN(C)CC2)cc1F] | 2 | 1.71 | 450 | d |
| I-125 | 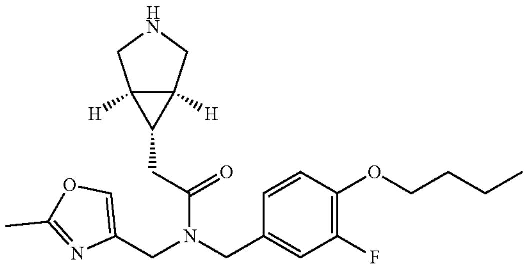 [SMILES: CCCCOc1ccc(CN(Cc2coc(C)n2)C(=O)C[C@H]2[C@@H]3CNC[C@@H]32)cc1F] | 2 | 1.66 | 426 | c |
| I-126 | 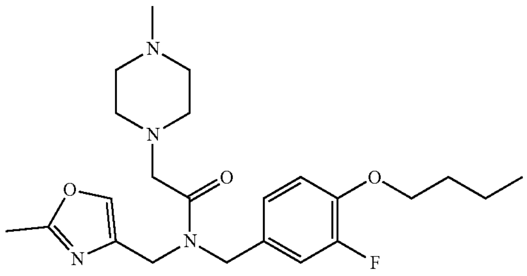 [SMILES: CCCCOc1ccc(CN(Cc2coc(C)n2)C(=O)CN2CCN(C)CC2)cc1F] | 2 | 1.59 | 433 | |

TABLE 23

| Compound No. | Structural formula | LC/MS Measurement condition | Retention time (min) | m/z | Configuration |
|---|---|---|---|---|---|
| I-127 | 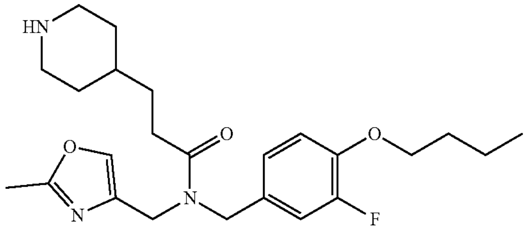 [SMILES: CCCCOc1ccc(CN(Cc2coc(C)n2)C(=O)CCC2CCNCC2)cc1F] | 2 | 1.68 | 432 | |

TABLE 24

| Compound No. | NMR |
|---|---|
| I-001 | 1H-NMR (CDCl3) δ: 1.02 (6H, d, J = 6.8 Hz), 1.67-1.77 (1H, m), 1.99-2.16 (1H, m), 2.66 (1H, t, J = 12.8 Hz), 2.78 (1H, dd, J = 38.9, 14.3 Hz), 3.08 (1H, d, J = 14.1 Hz), 3.27 (1H, t, J = 13.2 Hz), 3.49 (2H, s), 3.71 (2H, d, J = 6.5 Hz), 3.85 (3H, s), 3.86-4.03 (1H, m), 4.29 (2H, s), 4.49 (2H, s), 4.59 (1H, d, J = 49.4 Hz), 5.80 (1H, br s), 5.91 (1H, d, J = 1.3 Hz), 6.86 (2H, d, J = 8.5 Hz), 7.21 (2H, d, J = 8.5 Hz), 7.24 (1H, d, J = 1.8 Hz). |
| I-002 | 1H-NMR (CDCl3) δ: 1.02 (6H, d, J = 6.7 Hz), 1.21-1.30 (2H, m), 1.85 (2H, d, J = 11.8 Hz), 2.04-2.10 (3H, m), 2.20 (3H, s), 2.54 (2H, br s), 3.65-3.71 (3H, m), 4.23 (1H, d, J = 7.5 Hz), 4.40 (2H, s), 4.45 (2H, s), 6.85 (2H, d, J = 8.4 Hz), 6.98 (1H, d, J = 4.8 Hz), 7.08 (1H, s), 7.13 (2H, d, J = 8.2 Hz), 7.29-7.31 (1H, m). |
| I-003 | 1H-NMR (CDCl3) δ: 1.39-1.47 (2H, m), 1.92 (2H, d, J = 11.9 Hz), 2.09-2.14 (2H, m), 2.26 (3H, s), 2.68-2.71 (2H, br m), 3.68 (1H, br s), 3.84 (3H, s), 4.27 (2H, s), 4.54 (2H, s), 5.46 (1H, d, J = 5.9 Hz), 5.90 (1H, s), 6.96-7.01 (4H, m), 7.09 (1H, dd, J = 7.0, 3.5 Hz), 7.24-7.26 (3H, m), 7.33 (2H, dd, J = 7.3, 7.0 Hz). |
| I-004 | 1H-NMR (CDCl3) δ: 1.01 (3H, s), 1.03 (3H, s), 1.59-1.64 (3H, m), 1.66-1.73 (1H, m), 1.74-1.82 (1H, m), 1.85-1.88 (1H, m), 2.02-2.12 (1H, m), 2.26 (3H, s), 2.37-2.47 (2H, m), 2.54-2.57 (2H, m), 3.71 (2H, d, J = 6.5 Hz), 3.84 (3H, s), 4.04-4.07 (1H, m), 4.31 (2H, s), 4.46 (2H, s), 5.60 (1H, d, J = 7.8 Hz), 5.96 (1H, s), 6.85 (2H, d, J = 8.3 Hz), 7.19 (2H, d, J = 8.3 Hz), 7.24 (1H, s). |
| I-005 | 1H-NMR (CDCl3) δ: 1.02 (6H, d, J = 6.8 Hz), 1.33-1.50 (2H, m), 1.85-1.97 (2H, m), 2.01-2.16 (3H, m), 2.21 (3H, s), 2.26 (3H, s), 2.60-2.77 (2H, m), 3.62-3.72 (1H, m), 3.70 (3H, s), 3.71 (2H, d, J = 6.3 Hz), 4.17 (2H, s), 4.47 (2H, s), 5.45 (1H, br s), 5.70 (1H, s), 6.85 (2H, d, J = 8.5 Hz), 7.21 (2H, d, J = 8.5 Hz). |
| I-006 | 1H-NMR (CDCl3) δ: 1.02 (6H, d, J = 6.7 Hz), 1.22-1.30 (1H, m), 1.47-1.64 (1H, m), 1.69-1.79 (1H, m), 2.01-2.15 (1H, m), 2.62-2.71 (1H, m), 2.79 (1H, dd, J = 39.1, 14.5 Hz), 3.04-3.13 (1H, m), 3.24 3.35 (1H, m), 3.71 (2H, d, J = 6.5 Hz), 3.85-4.04 (1H, m), 4.40 (1H, d, J = 15.9 Hz), 4.46 (1H, d, J = 16.1 Hz), 4.50 (2H, s), 4.62 (1H, d, J = 50.6 Hz), 6.23 (1H, s), 6.84 (2H, d, J = 8.5 Hz), 7.02 (1H, dd, J = 8.2, 4.2 Hz), 7.16 (2H, d, J = 8.5 Hz), 7.31 (1H, td, J = 8.4, 2.8 Hz), 8.38 (1H, d, J = 2.6 Hz). |
| I-007 | 1H-NMR (CDCl3) δ: 1.02 (6H, d, J = 6.7 Hz), 1.81-1.90 (2H, m), 2.04-2.11 (3H, m), 2.60 (3H, s), 2.67 (2H, br s), 3.71 (2H, d, J = 6.5 Hz), 3.85 (1H, br s), 4.35 (2H, s), 4.50 (2H, s), 6.83 (2H, d, J =8.4 Hz), 6.95 (1H, d, J = 7.7 Hz), 7.16 (2H, d, J = 8.4 Hz), 7.21 (1H, dd, J = 6.1, 6.1 Hz), 7.60 (1H, dd, J = 7.8, 7.7 Hz), 8.48 (1H, s), 8.51 (1H, d, J = 4.4 Hz). |
| I-008 | 1H-NMR (CDCl3) δ: 1.02 (6H, d, J = 6.7 Hz), 1.23-1.31 (2H, m), 1.86-1.88 (2H, m), 2.03-2.11 (3H, m), 2.21 (3H, s), 2.44 (3H, s), 2.56 (2H, br s), 3.67 (1H, br s), 3.70 (2H, d, J = 6.5 Hz), 4.29 (1H, d, J = 7.3 Hz), 4.39 (2H, s), 4.52 (2H, s), 6.57 (1H, s), 6.69 (1H, d, J = 3.0 Hz), 6.86 (2H, d, J = 8.4 Hz), 7.14 (2H, d, J = 8.3 Hz). |
| I-009 | 1H-NMR (CDCl3) δ: 1.02 (6H, d, J = 6.7 Hz), 1.21-1.29 (2H, m), 1.81-1.85 (2H, m), 2.02-2.12 (3H, m), 2.20 (3H, s), 2.56 (2H, br s), 3.58 (3H, s), 3.63 (1H, br s), 3.69 (2H, d, J = 8.0 Hz), 4.29 (2H, s), 4.37 (1H, d, J = 7.5 Hz), 4.54 (2H, s), 6.04 (1H, s), 6.04 (1H, s), 6.62 (1H, s), 6.83 (2H, d, J = 8.4 Hz), 6.97 (2H, d, J = 8.4 Hz). |
| I-010 | 1H-NMR (CDCl3) δ: 1.36-1.45 (2H, m), 1.89-1.93 (2H, m), 2.08-2.13 (2H, m), 2.19 (3H, s), 2.24 (3H, s), 2.65 (2H, br s), 3.68 (1H, br s), 3.82 (3H, s), 3.84 (3H, s), 4.28 (2H, s), 4.45 (2H, s), 5.31 (1H, d, J = 6.3 Hz), 5.92 (1H, s), 6.77 (1H, d, J = 8.0 Hz), 7.06-7.09 (2H, m), 7.24 (1H, s). |
| I-011 | 1H-NMR (CDCl3) δ: 1.37-1.44 (2H, m), 1.89-1.92 (2H, m), 2.07-2.13 (2H, m), 2.25 (3H, s), 2.67 (2H, br s), 3.66 (1H, br s), 3.83 (3H, s), 3.96 (2H, s), 4.08 (2H, s), 4.26 (2H, s), 4.49 (2H, s), 5.37-5.39 (1H, br m), 5.88 (1H, s), 6.88 (2H, d, J = 8.3 Hz), 7.23-7.22 (3H, m). |
| I-013 | 1H-NMR (CDCl3) δ: 1.40-1.50 (2H, m), 1.92 (2H, d, J = 11.3 Hz), 2.10 (2H, br s), 2.27 (3H, s), 2.71 (2H, br s), 3.66 (1H, br s), 3.79 (3H, s), 3.84 (3H, s), 4.26 (2H, s), 4.54 (2H, s), 5.54 (1H, br s), 5.95 (1H, d, J = 1.8 Hz), 6.61 (1H, dd, J = 11.9, 2.3 Hz), 6.67 (1H, dd, J = 8.5, 2.0 Hz), 7.24 (1H, s), 7.32 (1H, dd, J = 8.7, 8.5 Hz). |
| I-014 | 1H-NMR (CDCl3) δ: 1.38-1.48 (2H, m), 1.91-1.93 (2H, br m), 2.08-2.13 (2H, br m), 2.26 (3H, s), 2.69 (2H, br s), 3.66 (1H, br s), 3.84 (3H, s), 3.86 (3H, s), 4.24 (2H, s), 4.48 (2H, s), 5.47-5.49 (1H, br m), 5.89 (1H, s), 6.90 (1H, dd, J = 8.2, 8.2 Hz), 7.00-7.05 (2H, m), 7.27-7.24 (1H, m). |

TABLE 25

| Compound No. | NMR |
|---|---|
| I-015 | 1H-NMR (CDCl3) δ: 1.37-1.45 (2H, m), 1.89-1.93 (2H, m), 2.07-2.14 (2H, m), 2.25 (3H, s), 2.66 (2H, br s), 3.18 (2H, t, J = 8.7 Hz), 3.68 (1H, br s), 3.84 (3H, s), 4.26 (2H, s), 4.46 (2H, s), 4.56 (2H, t, J = 8.7 Hz), 5.39 (1H, d, J = 6.5 Hz), 5.91 (1H, s), 6.72 (1H, d, J = 8.2 Hz), 7.02 (1H, d, J = 8.0 Hz), 7.17 (1H, s), 7.23 (1H, s). |
| I-017 | 1H-NMR (CDCl3) δ: 1.03 (6H, d, J = 6.5 Hz), 1.19-1.34 (2H, m), 1.45-1.68 (1H, m), 1.85-1.96 (2H, m), 2.01-2.14 (1H, m), 2.63-2.75 (2H, m), 2.97-3.08 (2H, m), 3.68-3.82 (1H, m), 3.71 (2H, d, J = 6.5 Hz), 4.42 (2H, s), 4.49 (2H, s), 5.77 (1H, br s), 6.84 (2H, d, J = 8.3 Hz), 7.03 (1H, dd, J = 8.4, 4.4 Hz), 7.16 (2H, d, J = 8.5 Hz), 7.29-7.33 (1H, m), 8.36 (1H, d, J = 2.8 Hz). |
| I-018 | 1H-NMR (CDCl3) δ: 1.02 (6H, d, J = 6.8 Hz), 1.30-1.44 (1H, m), 1.56-1.74 (1H, m), 1.98-2.17 (2H, m), 2.65-2.95 (3H, m), 3.07-3.24 (1H, m), 3.71 (2H, d, J = 6.5 Hz), 3.84 (3H, s), 3.97-4.09 (1H, m), 4.22-4.41 (1H, m), 4.25 (2H, s), 4.51 (2H, s), 5.85 (1H, s), 5.92 (1H, br s), 6.86 (2H, d, J = 8.5 Hz), 7.22 (2H, d, J = 9.0 Hz), 7.22 (1H, br s). |
| I-019 | 1H-NMR (CDCl3) δ: 1.03 (6H, d, J = 6.8 Hz), 1.32-1.42 (2H, m), 1.90 (2H, d, J = 9.8 Hz), 2.05-2.11 (3H, m), 2.23 (3H, br s), 2.63 (2H, br s), 3.66 (1H, br s), 3.70 (2H, d, J = 6.5 Hz), 4.47 (2H, s), 4.50 (2H, s), 5.18 (1H, br s), 6.85 (2H, d, J = 8.5 Hz), 7.15-7.11 (3H, m), 8.63 (1H, d, J = 5.1 Hz), 9.12 (1H, s). |
| I-020 | 1H-NMR (CDCl3) δ: 1.02 (6H, d, J = 6.7 Hz), 1.37-1.42 (2H, m), 1.89-1.94 (2H, m), 2.04-2.13 (3H, m), 2.24 (3H, s), 2.65 (2H, br s), 3.67 (1H, br s), 4.49 (2H, s), 4.52 (2H, s), 5.44 (1H, br s), 6.84 (2H, d, J = 8.4 Hz), 7.15 (2H, d, J = 8.3 Hz), 8.39 (1H, s), 8.48 (2H, d, J = 4.6 Hz). |
| I-021 | 1H-NMR (400 MHZ, CDCl3) 8 1.04 (t, J = 7.4 Hz, 3H), 1.35-1.49 (m, 2H), 1.74-1.86 (m, 2H), 1.88-1.96 (m, 2H), 2.04-2.17 (m, 2H), 2.25 (s, 3H), 2.59-2.75 (m, 2H), 3.61-3.74 (m, 2H), 3.91 (t, J = 6.5 Hz, 2H), 4.42 (s, 2H), 4.49 (s, 2H), 5.78 (brs, 1H), 6.84 (d, J = 8.5 Hz, 2H), 6.98-7.07 (m, 1H), 7.16 (d, J = 8.5 Hz, 2H), 7.26-7.35 (m, 1H), 8.35 (d, J = 2.5 Hz, 1H). |
| I-022 | 1H-NMR (CDCl3) δ: 1.02 (6H, d, J = 6.7 Hz), 1.14-1.39 (1H, m), 1.51-1.61 (1H, m), 1.69-1.79 (1H, m), 2.00-2.14 (1H, m), 2.61-2.71 (1H, m), 2.79 (1H, dd, J = 39.5, 14.7 Hz), 3.02-3.15 (1H, m), 3.18-3.35 (1H, m), 3.71 (2H, d, J = 6.7 Hz), 3.83-4.05 (1H, m), 4.43 (2H, dd, J = 22.0, 16.0 Hz), 4.50 (2H, s), 4.62 (1H, d, J = 50.7 Hz), 6.22 (1H, s), 6.84 (2H, d, J = 8.5 Hz), 7.02 (1H, dd, J = 8.5, 4.0 Hz), 7.16 (2H, d, J = 8.4 Hz), 7.31 (1H, td, J = 8.3, 2.8 Hz), 8.38 (1H, d, J = 2.8 Hz). |
| I-023 | 1H-NMR (CDCl3) δ: 1.02 (6H, d, J = 6.7 Hz), 1.41-1.50 (2H, m), 1.94 (2H, d, J = 10.2 Hz), 2.03-2.15 (3H, m), 2.26 (3H, s), 2.28 (3H, s), 2.68 (2H, br s), 3.66-3.71 (3H, m), 4.43 (2H, s), 4.53 (2H, s), 6.65 (1H, br s), 6.82 (2H, d, J = 8.4 Hz), 7.10-7.15 (3H, m), 7.44 (1H, d, J = 7.5 Hz). |
| I-024 | 1H-NMR (CDCl3) δ: 1.02 (6H, d, J = 6.7 Hz), 1.29-1.38 (2H, m), 1.89 (2H, d, J = 11.0 Hz), 2.02-2.10 (4H, m), 2.23 (3H, s), 2.61 (2H, br s), 3.66 (1H, br s), 3.70 (2H, d, J = 6.5 Hz), 4.41 (4H, s), 4.46 (1H, d, J = 8.0 Hz), 6.17 (1H, d, J = 2.8 Hz), 6.31 (1H, s), 6.84 (2H, d, J = 8.4 Hz), 7.12 (2H, d, J = 8.3 Hz), 7.36 (1H, s). |
| I-025 | 1H-NMR (CDCl3) δ: 1.02 (6H, d, J = 6.7 Hz), 1.34-1.43 (2H, m), 1.90 (2H, d, J = 10.0 Hz), 2.04-2.11 (3H, m), 2.23 (3H, s), 2.63 (2H, br s), 3.67 (1H, br s), 3.71 (2H, d, J = 6.5 Hz), 4.49 (2H, s), 4.68 (2H, s), 5.19 (1H, d, J = 6.5 Hz), 6.86 (2H, d, J = 8.2 Hz), 7.17 (2H, d, J = 8.2 Hz), 7.28 (1H, d, J = 3.0 Hz), 7.69 (1H, d, J = 3.0 Hz). |
| I-026 | 1H-NMR (CDCl3) δ: 1.38-1.46 (2H, m), 1.91 (2H, d, J = 11.0 Hz), 2.10 (2H, dd, J = 11.0, 11.0 Hz), 2.25 (3H, s), 2.67 (2H, br s), 3.66 (1H, br s), 3.84 (3H, s), 4.25 (2H, s), 4.46 (2H, s), 5.42 (1H, d, J = 6.5 Hz), 5.94 (3H, br s), 6.75 (2H, s), 6.81 (1H, s), 7.24 (1H, s). |
| I-027 | 1H-NMR (CDCl3) δ: 1.02 (6H, d, J = 6.8 Hz), 1.42-1.56 (1H, m), 1.57-1.65 (1H, m), 1.95-2.14 (2H, m), 2.63-2.75 (1H, m), 2.84 (1H, dd, J = 29.4, 13.9 Hz), 2.98-3.09 (1H, m), 3.17-3.28 (1H, m), 3.71 (2H, d, J = 6.7 Hz), 3.84 (3H, s), 4.21-4.37 (1H, m), 4.28 (2H, dd, J = 27.7, 15.9 Hz), 4.51 (2H, dd, J = 23.7, 15.2 Hz), 5.88 (1H, s), 5.98 (1H, s), 6.86 (2H, d, J = 8.5 Hz), 7.21 (2H, d, J = 8.5 Hz), 7.23 (1H, d, J = 1.8 Hz). |
| I-029 | 1H-NMR (CDCl3) δ: 0.67 (2H, ddd, J = 8.6, 4.1, 1.5 Hz), 0.95 (2H, ddd, J = 8.6, 4.1, 1.5 Hz), 1.40-1.42 (2H, m), 1.86-1.90 (3H, m), 2.07-2.10 (2H, m), 2.25 (3H, s), 2.66 (2H, br s), 3.66 (1H, br s), 3.83 (3H, s), 4.26 (2H, s), 4.50 (2H, s), 5.34 (1H, br s), 5.91 (1H, d, J = 1.8 Hz), 7.03 (2H, d, J = 8.0 Hz), 7.18 (2H, d, J = 8.0 Hz), 7.24 (1H, d, J = 1.8 Hz). |

TABLE 26

| Compound No. | NMR |
|---|---|
| I-031 | 1H-NMR (CDCl3) δ: 1.02 (6H, d, J = 6.8 Hz), 1.41-1.50 (2H, m), 1.93 (2H, d, J = 10.7 Hz), 2.04-2.15 (3H, m), 2.26 (3H, s), 2.31 (3H, s), 2.69 (2H, br s), 3.67 (1H, br s), 3.71 (2H, d, J = 8.0 Hz), 4.33 (2H, s), 4.49 (2H, s), 6.28 (1H, br s), 6.84 (2H, d, J = 8.4 Hz), 6.90 (1H, d, J = 7.8 Hz), 7.18 (2H, d, J = 8.3 Hz), 7.40 (1H, d, J = 7.9 Hz), 8.32 (1H, s). |
| I-032 | 1H-NMR (CDCl3) δ: 1.03 (6H, d, J = 6.7 Hz), 1.31-1.41 (2H, m), 1.89 (2H, d, J = 9.8 Hz), 2.04-2.12 (3H, m), 2.23 (3H, s), 2.62 (2H, br s), 3.66 (1H, br s), 3.70 (2H, d, J = 6.5 Hz), 4.47 (2H, s), 4.59 (2H, s), 5.11 (1H, br s), 6.84 (2H, d, J = 8.4 Hz), 7.13 (2H, d, J = 8.4 Hz), 7.25 (1H, d, J = 8.0 Hz), 7.86 (1H, d, J = 8.0 Hz), 8.78 (1H, s). |
| I-033 | 1H-NMR (CDCl3) δ: 1.02 (6H, d, J = 6.7 Hz), 1.31-1.38 (2H, m), 1.90 (2H, d, J = 10.8 Hz), 2.04-2.11 (3H, m), 2.22 (3H, s), 2.60 (2H, br s), 3.66-3.74 (3H, br m), 4.47 (2H, s), 4.52 (1H, d, J = 7.4 Hz), 4.57 (2H, s), 6.56 (1H, s), 6.85 (2H, d, J = 8.4 Hz), 7.16-7.28 (4H, m), 7.43 (1H, d, J = 8.0 Hz), 7.51 (1H, d, J = 7.5 Hz). |

TABLE 26-continued

| Compound No. | NMR |
|---|---|
| I-034 | 1H-NMR (CDCl3) δ: 1.02 (6H, d, J = 6.7 Hz), 1.24-1.30 (2H, m), 1.86 (2H, d, J = 10.9 Hz), 2.03-2.10 (3H, m), 2.20 (3H, s), 2.56 (2H, br s), 3.67 (1H, br s), 3.70 (2H, d, J = 6.5 Hz), 4.28 (1H, d, J = 7.5 Hz), 4.39 (2H, s), 4.63 (2H, s), 6.86 (2H, d, J = 8.5 Hz), 6.93-6.95 (2H, m), 7.13 (2H, d, J = 8.3 Hz), 7.24-7.22 (1H, m). |
| I-035 | 1H-NMR (CDCl3) δ: 1.02 (6H, d, J = 6.7 Hz), 1.37-1.46 (2H, m), 1.92 (2H, d, J = 10.3 Hz), 2.04-2.12 (3H, m), 2.24 (3H, s), 2.67 (2H, br s), 3.66 (1H, br s), 3.70 (2H, d, J = 6.5 Hz), 4.29 (2H, s), 4.45 (2H, s), 5.28 (1H, d, J = 6.9 Hz), 6.85 (2H, d, J = 8.3 Hz), 7.16 (2H, d, J = 8.4 Hz), 7.37 (1H, s), 7.81 (1H, s). |
| I-036 | 1H-NMR (CDCl3) δ: 1.02 (2.7H, d, J = 6.8 Hz), 1.03 (3.3H, d, J = 6.3 Hz), 1.99-2.13 (1H, m), 2.28 (1.35H, s), 2.28 (1.65H, s), 2.33-2.74 (8H, m), 3.22 (0.9H, s), 3.33 (1.1H, s), 3.66-3.74 (2H, m), 3.84 (1.35H, s), 3.87 (1.65H, s), 4.49-4.55 (3.1H, m), 4.58 (0.9H, s), 6.04 (0.55H, d, J = 1.8 Hz), 6.17 (0.45H, d, J = 1.5 Hz), 6.83 (1.1H, d, J = 8.3 Hz), 6.86 (0.9H, d, J = 8.5 Hz), 7.11 (1H, d, J = 8.5 Hz), 7.19 (1.1H, d, J = 8.5 Hz), 7.24-7.32 (0.9H, m). |
| I-038 | 1H-NMR (CDCl3) δ: 1.40 (2H, td, J = 10.2, 5.1 Hz), 1.89-1.92 (2H, br m), 2.10 (2H, td, J = 10.2, 5.1 Hz), 2.25 (3H, s), 2.34 (3H, s), 2.65-2.67 (2H, br m), 3.67 (1H, br s), 3.84 (3H, s), 4.27 (2H, s), 4.51 (2H, s), 5.35 (1H, br s), 5.91 (1H, d, J = 1.9 Hz), 7.13 (2H, d, J = 7.9 Hz), 7.19 (2H, d, J = 7.9 Hz), 7.24 (1H, d, J = 1.9 Hz). |
| I-039 | 1H-NMR (CDCl3) δ: 1.02 (6H, d, J = 6.7 Hz), 1.29-1.37 (2H, m), 1.87 (2H, d, J = 10.3 Hz), 2.05-2.11 (2H, m), 2.22 (3H, s), 2.38 (3H, s), 2.58 (2H, br s), 3.65 (1H, br s), 3.71 (2H, d, J = 6.5 Hz), 4.39 (2H, s), 4.46 (2H, s), 4.54 (1H, d, J = 7.3 Hz), 5.84 (1H, s), 6.86 (2H, d, J = 8.3 Hz), 7.14 (2H, d, J = 8.3 Hz). |
| I-040 | 1H-NMR (CDCl3) δ: 1.02 (6H, d, J = 6.7 Hz), 1.25-1.32 (2H, m), 1.86 (2H, d, J = 11.0 Hz), 2.04-2.10 (3H, m), 2.21 (3H, s), 2.55 (2H, br s), 3.59 (3H, s), 3.70 (3H, d, J = 6.5 Hz), 4.22 (2H, s), 4.41 (1H, d, J = 7.9 Hz), 4.44 (2H, s), 5.96 (1H, s), 6.44 (1H, s), 6.51 (1H, s), 6.84 (2H, d, J = 8.2 Hz), 7.18 (2H, d, J = 8.2 Hz). |
| I-041 | 1H-NMR (CDCl3) δ: 1.02 (6H, d, J = 5.6 Hz), 1.41-1.50 (2H, m), 1.95 (2H, d, J = 12.0 Hz), 2.04-2.14 (3H, m), 2.26 (3H, s), 2.72 (2H, br s), 3.69-3.72 (3H, br m), 3.82 (2H, s), 3.83 (2H, s), 4.21 (2H, s), 4.52 (2H, s), 5.58 (1H, s), 6.85 (2H, d, J = 6.7 Hz), 7.26 (3H, d, J = 2.3 Hz). |
| I-042 | 1H-NMR (400 MHZ, CDCl3) 6 1.36-1.50 (m, 2H), 1.88-1.98 (m, 2H), 2.06-2.19 (m, 2H), 2.27 (s, 3H), 2.61-2.76 (m, 2H), 3.61-3.73 (m, 1H), 3.80 (s, 3H), 4.41 (s, 2H), 4.50 (s, 2H), 5.83 (brs, 1H), 6.85 (d, J = 8.7 Hz, 2H), 6.97-7.07 (m, 1H), 7.18 (d, J = 8.7 Hz, 2H), 7.26-7.36 (m, 1H), 8.35 (d, J =2.5 Hz, 1H). |
| I-044 | 1H-NMR (CDCl3) δ: 0.20-0.28 (1H, m), 0.33-0.56 (3H, m), 1.02 (6H, d, J = 6.8 Hz), 1.66-1.83 (1H, m), 1.84-1.96 (1H, m), 1.99-2.29 (3H, m), 2.23 (3H, s), 2.33-2.52 (2H, m), 3.48-3.70 (1H, m), 3.70 (2H, d, J = 6.8 Hz), 4.41 (2H, s), 4.49 (2H, d, J = 2.8 Hz), 5.98 (1H, br s), 6.84 (2H, d, J = 8.3 Hz), 7.00 (1H, dd, J = 8.2, 4.6 Hz), 7.16 (2H, d, J = 8.5 Hz), 7.31 (1H, td, J = 8.4, 2.9 Hz), 8.36 (1H, d, J = 2.8 Hz). |
| I-045 | 1H-NMR (CDCl3) δ: 0.18-0.26 (1H, m), 0.30-0.51 (3H, m), 1.02 (6H, d, J = 6.7 Hz), 1.62-1.78 (1H, m), 1.83-1.94 (1H, m), 2.00-2.26 (3H, m), 2.23 (3H, s), 2.28-2.60 (2H, m), 3.52-3.75 (1H, m), 3.71 (2H, d, J = 6.5 Hz), 3.84 (3H, s), 4.26 (2H, s), 4.45 (1H, d, J = 15.3 Hz), 4.51 (1H, d, J = 15.3 Hz), 5.36 (1H, br s), 5.87 (1H, d, J = 1.3 Hz), 6.86 (2H, d, J = 8.5 Hz), 7.21 (2H, d, J = 8.5 Hz), 7.24 (1H, d, J = 2.0 Hz). |

TABLE 27

| Compound No. | NMR |
|---|---|
| I-046 | 1H-NMR (CDCl3) δ: 1.40-1.50 (2H, m), 1.94 (2H, d, J = 13.2 Hz), 2.09-2.14 (2H, br m), 2.27 (3H, br s), 2.70 (2H, br s), 3.67 (1H, br s), 3.84 (3H, s), 4.23 (2H, s), 4.57 (2H, s), 5.60 (1H, d, J = 6.8 Hz), 5.84 (1H, d, J = 1.9 Hz), 7.16 (2H, d, J = 8.2 Hz), 7.23 (1H, d, J = 1.9 Hz), 7.33 (2H, d, J = 8.2 Hz). |
| I-047 | 1H-NMR (CDCl3) δ: 1.33 (6H, d, J = 6.0 Hz), 1.39-1.45 (2H, m), 1.91 (2H, d, J = 11.3 Hz), 2.07-2.14 (2H, br m), 2.25 (3H, s), 2.67 (2H, br s), 3.66 (1H, br s), 3.83 (3H, s), 4.26 (2H, s), 4.48 (2H, s), 4.50-4.57 (3H, m), 5.38 (1H, br s), 5.87 (1H, d, J = 1.8 Hz), 6.84 (2H, d, J = 9.0 Hz), 7.23-7.19 (4H, m). |
| I-048 | 1H-NMR (CDCl3) δ: 1.02 (6H, d, J = 6.7 Hz), 1.50-1.58 (1H, m), 1.72 (1H, d, J = 12.0 Hz), 2.01-2.13 (1H, m), 2.63-2.85 (2H, m), 3.08 (1H, d, J = 13.2 Hz), 3.27 (1H, t, J = 12.7 Hz), 3.71 (2H, d, J = 12.6 Hz), 3.85-4.02 (4H, m), 4.29 (2H, s), 4.49-4.66 (3H, m), 5.81 (1H, d, J = 6.7 Hz), 5.91 (1H, s), 6.86 (2H, d, J = 8.4 Hz), 7.20-7.26 (3H, m). |
| I-049 | 1H-NMR (CDCl3) δ: 1.02 (6H, d, J = 6.8 Hz), 1.72-1.85 (2H, m), 2.03-2.29 (6H, m), 2.85 (1H, d, J = 10.8 Hz), 3.12 (1H, t, J = 10.7 Hz), 3.62-3.75 (2H, m), 3.77-3.93 (2H, m), 4.28 (2H, s), 4.49 (2H, s), 4.61-4.98 (3H, m), 5.85 (1H, br s), 5.90 (1H, s), 6.85 (2H, d, J = 8.5 Hz), 7.20-7.23 (3H, m). |
| I-050 | 1H-NMR (CDCl3) δ: 1.02 (6H, d, J = 6.7 Hz), 1.76-1.85 (1H, m), 2.02-2.14 (1H, m), 2.29 (3H, s), 2.86 (1H, d, J = 11.7 Hz), 3.13 (1H, t, J = 11.0 Hz), 3.62-3.89 (4H, m), 4.43 (2H, d, J = 7.9 Hz), 4.49 (2H, s), 4.64-4.99 (3H, m), 6.33 (1H, br s), 6.83 (2H, d, J = 8.5 Hz), 7.01 (1H, dd, J = 8.3 Hz, 4.0 Hz), 7.16 (2H, J = 8.5 Hz), 7.29 (1H, td, J = 9.8 Hz, 4.6 Hz), 8.37 (1H, d, J = 2.6 Hz). |
| I-051 | 1H-NMR (CDCl3) δ: 1.41-1.49 (2H, m), 1.93 (2H, d, J = 10.4 Hz), 2.10-2.15 (2H, m), 2.26 (3H, s), 2.69 (2H, br s), 3.66 (1H, br s), 3.84 (3H, s), 3.93 (3H, s), 4.19 (2H, s), 4.50 (2H, |

TABLE 27-continued

| Compound No. | NMR |
|---|---|
| | s), 5.62 (1H, d, J = 7.2 Hz), 5.87 (1H, s), 6.71 (1H, d, J = 8.5 Hz), 7.23-8.26 (1H, m), 7.59 (1H, d, J = 6.7 Hz), 8.06 (1H, s). |
| I-052 | 1H-NMR (CDCl3) δ: 1.03 (6H, d, J = 6.8 Hz), 1.22-1.32 (2H, m), 1.85-1.89 (2H, br m), 2.04-2.13 (3H, m), 2.21 (3H, s), 2.57 (2H, br s), 3.67 (1H, br s), 3.70 (2H, d, J = 6.5 Hz), 4.23 (1H, d, J = 7.7 Hz), 4.34 (2H, s), 4.54 (2H, s), 6.86 (2H, d, J = 8.5 Hz), 7.11 (2H, d, J = 8.4 Hz), 7.17 (2H, d, J = 5.6 Hz), 8.55 (2H, d, J = 5.6 Hz). |
| I-053 | 1H-NMR (CDCl3) δ: 1.02 (6H, d, J = 6.8 Hz), 1.21-1.30 (2H, m), 1.85 (2H, d, J = 10.4 Hz), 2.03-2.12 (3H, m), 2.20 (3H, s), 2.56 (2H, br s), 3.64 (1H, br s), 3.70 (2H, d, J = 6.5 Hz), 3.87 (3H, s), 4.27 (2H, s), 4.29 (1H, d, J = 7.9 Hz), 4.65 (2H, s), 6.15 (1H, s), 6.85 (2H, d, J = 8.4 Hz), 6.98 (2H, d, J = 8.4 Hz), 7.40 (1H, s). |
| I-054 | 1H-NMR (CDCl3) δ: 1.02 (6H, d, J = 6.7 Hz), 1.47-1.63 (1H, m), 2.07 (1H, dd, J = 12.4, 5.6 Hz), 2.20-2.35 (2H, m), 2.32 (3H, s), 2.46 (1H, dd, J = 9.9, 3.2 Hz), 2.64 (1H, dd, J = 9.7, 7.0 Hz), 2.68-2.76 (1H, m), 3.71 (2H, d, J = 6.7 Hz), 3.84 (3H, s), 4.23 (1H, d, J = 16.1 Hz), 4.29 (1H, d, J = 16.1 Hz), 4.33-4.41 (1H, m), 4.48 (2H, s), 5.69 (1H, d, J = 6.4 Hz), 5.90 (1H, d, J = 1.9 Hz), 6.85 (2H, d, J = 8.5 Hz), 7.19 (2H, d, J = 8.5 Hz), 7.24 (1H, d, J = 1.8 Hz). |
| I-055 | 1H-NMR (CDCl3) δ: 1.01 (6H, d, J = 6.8 Hz), 1.40-1.50 (2H, m), 1.94 (2H, d, J = 10.8 Hz), 2.02-2.15 (3H, m), 2.25 (3H, s), 2.68 (2H, br s), 3.68-3.72 (3H, br m), 3.81 (3H, s), 4.28 (2H, s), 4.52 (2H, s), 5.47 (1H, d, J = 6.8 Hz), 5.93 (1H, s), 6.85 (2H, d, J = 8.3 Hz), 7.22 (2H, d, J = 8.3 Hz), 7.35 (2H, d, J = 7.3 Hz), 7.46-7.40 (3H, m). |
| I-056 | 1H-NMR (CDCl3) δ: 1.02 (6H, d, J = 6.7 Hz), 1.39-1.47 (2H, m), 1.93 (2H, d, J = 10.5 Hz), 2.02-2.15 (3H, m), 2.26 (3H, s), 2.67 (2H, br s), 3.67-3.73 (3H, br m), 4.52 (2H, s), 4.53 (2H, s), 5.80 (1H, br s), 6.82 (2H, d, J = 8.4 Hz), 7.05 (1H, s), 7.13 (2H, d, J = 8.4 Hz), 7.38 (1H, d, J = 5.0 Hz), 8.67 (1H, d, J = 5.0 Hz). |
| I-057 | 1H-NMR (CDCl3) δ: 1.02 (6H, d, J = 6.8 Hz), 1.23-1.31 (2H, m), 1.87 (2H, d, J = 10.3 Hz), 2.03-2.11 (3H, m), 2.20 (3H, s), 2.57 (2H, br s), 3.66 (1H, s), 3.70 (2H, d, J = 6.5 Hz), 4.24 (1H, d, J = 7.8 Hz), 4.31 (2H, s), 4.57 (2H, s), 6.86 (2H, d, J = 8.5 Hz), 7.09 (2H, d, J = 8.4 Hz), 7.25-7.28 (1H, m), 7.64 (1H, d, J = 7.7 Hz), 8.53-8.50 (2H, m). |

TABLE 28

| Compound No. | NMR |
|---|---|
| I-058 | 1H-NMR (CDCl3) δ: 1.02 (6H, d, J = 6.7 Hz), 1.44 (2H, s), 2.02-2.12 (1H, m), 2.25 (3H, s), 2.34 (2H, d, J = 8.7 Hz), 2.86 (1H, s), 3.07 (2H, d, J = 8.9 Hz), 3.71(2H, d, J = 6.5 Hz), 3.84 (3H, s), 4.21 (2H, s), 4.46 (2H, s), 5.43 (1H, s), 5.89(1H, s), 6.84 (2H, d, J = 8.3 Hz), 7.19 (2H, d, J = 8.3 Hz), 7.23 (1H, s). |
| I-059 | 1H-NMR (CDCl3) δ: 1.02 (6H, d, J = 6.7 Hz), 2.05-2.11 (2H, m), 2.25 (3H, s), 2.55-2.61 (1H, m), 2.87 (2H, dd, J = 6.4, 6.4 Hz), 3.30 (2H, dd, J = 7.3, 7.3 Hz), 3.38 (2H, dd, J = 6.0, 6.0 Hz), 3.71 (2H, d, J = 6.4 Hz), 4.27 (2H, s), 4.49 (2H, s), 5.67 (1H, br s), 5.90 (1H, s), 6.85 (2H, d, J = 8.5 Hz), 7.19-7.24 (3H, m). |
| I-060 | 1H-NMR (CDCl3) δ: 1.02 (6H, d, J = 6.5 Hz), 1.23-1.31 (3H, m), 1.71 (2H, br s), 1.85-1.90 (2H, br m), 2.04-2.10 (2H, m), 2.21 (3H, s), 2.58 (2H, br s), 3.65 (1H, br s), 3.70 (2H, d, J = 6.5 Hz), 3.86 (3H, s), 4.21 (1H, d, J = 7.8 Hz), 4.34 (2H, s), 4.34 (2H, s), 6.86 (2H, d, J = 8.8 Hz), 7.13 (2H, d, J = 8.8 Hz), 7.28 (1H, s), 7.36 (1H, s). |
| I-062 | 1H-NMR (CDCl3) δ: 1.02 (6H, d, J = 6.7 Hz), 1.60 (2H, br s), 1.81 (2H, d, J = 8.0 Hz), 1.88 (2H, d, J = 13.2 Hz), 2.02-2.12 (3H, m), 2.38 (3H, s), 3.30 (2H, s), 3.70 (2H, d, J = 6.7 Hz), 3.84 (2H, s), 4.02-4.10 (1H, m), 4.23 (2H, d, J = 9.7 Hz), 4.45 (2H, s), 5.29 (1H, s), 5.91 (1H, d, J = 2.0 Hz), 6.84 (2H, d, J = 8.5 Hz), 7.18 (2H, d, J = 8.5 Hz), 7.23 (1H, d, J = 2.1 Hz). |
| I-064 | 1H-NMR (CDCl3) δ: 0.81 (3H, d, J = 6.7 Hz), 1.02 (6H, d, J = 6.7 Hz), 1.34 (1H, ddd, J = 23.9, 12.2, 4.1 Hz), 1.47-1.56 (1H, m), 1.72-1.75 (1H, m), 1.94-2.02 (2H, m), 2.04-2.12 (1H, m), 2.25 (3H, s), 2.78 (2H, br s), 3.30-3.39 (1H, m), 3.71 (2H, d, J = 6.7 Hz), 3.82 (3H, s), 4.23-4.31 (2H, m), 4.46-4.55 (2H, m), 5.24 (1H, d, J = 7.3 Hz), 5.87 (1H, d, J = 2.0 Hz), 6.85 (2H, d, J = 8.5 Hz), 7.23-7.20 (3H, m). |
| I-065 | 1H-NMR (CDCl3) δ: 0.81 (3H, d, J = 6.5 Hz), 1.02 (6H, d, J = 6.7 Hz), 1.34 (1H, ddd, J = 24.0, 12.2, 4.1 Hz), 1.45-1.56 (1H, m), 1.72 (1H, dd, J = 11.2, 11.2 Hz), 1.94-2.12 (3H, m), 2.24 (3H, s), 2.75-2.81 (2H, br m), 3.31-3.38 (1H, m), 3.71 (2H, d, J = 6.5 Hz), 3.82 (3H, s), 4.23-4.32 (2H, m), 4.55-4.46 (2H, m), 5.24 (1H, d, J = 7.7 Hz), 5.87 (1H, d, J = 2.0 Hz), 6.85 (2H, d, J = 8.7 Hz), 7.20-7.23 (3H, m). |
| I-066 | 1H-NMR (CDCl3) δ: 1.02 (6H, d, J = 6.8 Hz), 1.37 (3H, s), 1.63-1.72 (2H, br m), 2.05-2.12 (5H, m), 2.26 (3H, s), 2.60-2.63 (2H, br m), 3.71 (2H, d, J = 6.5 Hz), 3.84 (3H, s), 4.32 (2H, s), 4.46 (2H, s), 5.05 (1H, br s), 5.92 (1H, d, J = 2.0 Hz), 6.87 (2H, d, J = 8.5 Hz), 7.21 (2H, t, J = 9.0 Hz), 7.26 (1H, s). |
| I-067 | 1H-NMR (CDCl3) δ: 1.02 (6H, d, J = 6.7 Hz), 1.31-1.46 (2H, m), 1.65-1.78 (3H, m), 1.83-1.88 (2H, m), 2.03-2.13 (1H, m), 2.21-2.16 (2H, m), 2.30-2.36 (1H, m), 2.39 (3H, s), 2.44-2.52 (1H, br m), 2.72 (1H, d, J = 12.5 Hz), 3.71 (2H, d, J = 6.5 Hz), 3.74-3.81 (1H, m), 3.84 (3H, s), 4.25 (2H, s), 4.44-4.54 (2H, m), 5.44 (1H, br s), 5.89 (1H, d, J = 2.1 Hz), 6.86 (2H, d, J = 8.7 Hz), 7.21 (2H, d, J = 8.5 Hz), 7.24 (1H, d, J = 2.1 Hz). |
| I-068 | 1H-NMR (CDCl3) δ: 1.02 (6H, d, J = 6.7 Hz), 1.79-1.83 (6H, m), 2.03-2.13 (1H, m), 2.93-2.96 (6H, m), 3.71 (2H, d, J = 6.5 Hz), 3.84 (3H, s), 4.25 (2H, s), 4.43 (2H, s), 5.18 (1H, |

TABLE 28-continued

| Compound No. | NMR |
|---|---|
| | s), 5.89 (1H, d, J = 2.1 Hz), 6.85 (2H, d, J = 8.5 Hz), 7.19 (2H, d, J = 8.5 Hz), 7.24 (1H, d, J = 2.1 Hz). |

TABLE 29

| Compound No. | NMR |
|---|---|
| I-069 | 1H-NMR (CDCl3) δ: 1.02 (6H, d, J = 6.7 Hz), 1.07 (3H, t, J = 7.2 Hz), 1.35-1.45 (2H, m), 1.90-1.94 (2H, m), 2.02-2.12 (3H, m), 2.37 (2H, q, J = 7.2 Hz), 2.76 (2H, br s), 3.65-3.71 (1H, m), 3.71 (2H, d, J = 6.5 Hz), 3.83 (3H, s), 4.27 (2H, s), 4.47 (2H, s), 5.31-5.29 (1H, br m), 5.91 (1H, d, J = 2.0 Hz), 6.85 (2H, d, J = 8.7 Hz), 7.20 (2H, d, J = 8.7 Hz), 7.23 (1H, d, J = 2.1 Hz). |
| I-071 | 1H-NMR (CDCl3) δ: 1.02 (6H, d, J = 6.7 Hz), 1.38-1.47 (2H, m), 1.93-2.00 (4H, m), 2.03-2.13 (1H, m), 2.58-2.61 (2H, br m), 3.40-3.47 (1H, m), 3.71 (3H, d, J = 6.5 Hz), 3.84 (3H, s), 4.27 (2H, s), 4.47 (2H, s), 4.59 (2H, t, J = 6.1 Hz), 4.64 (2H, t, J = 6.5 Hz), 5.37 (1H, s), 5.90 (1H, d, J = 2.1 Hz), 6.85 (2H, d, J = 8.5 Hz), 7.24-7.19 (3H, m). |
| I-072 | 1H-NMR (CDCl3) δ: 1.02 (6H, d, J = 6.7 Hz), 1.50-1.41 (2H, m), 1.88-1.92 (2H, m), 2.03-2.13 (1H, m), 2.32-2.38 (2H, m), 2.61-2.66 (2H, m), 2.84 (3H, d, J = 5.0 Hz), 2.97 (2H, s), 3.72 (1H, d, J = 8.0 Hz), 3.74-3.77 (1H, m), 3.85 (3H, s), 4.26 (2H, s), 4.48 (2H, s), 5.43 (1H, br s), 5.89 (1H, d, J = 2.1 Hz), 6.86 (2H, d, J = 8.5 Hz), 7.14 (1H, br s), 7.21 (2H, d, J = 8.5 Hz), 7.24 (1H, d, J = 2.1 Hz). |
| I-073 | 1H-NMR (CDCl3) δ: 1.00-1.10 (2H, m), 1.02 (6H, d, J = 6.8 Hz), 1.42-1.49 (1H, br m), 1.72 (2H, br s), 1.89 (3H, d, J = 6.8 Hz), 2.02-2.12 (1H, m), 2.34-2.42 (2H, m), 2.46 (3H, s), 2.98-3.02 (2H, br m), 3.71 (2H, d, J = 6.7 Hz), 3.84 (3H, s), 4.11-4.22 (1H, m), 4.26 (2H, s), 4.49 (2H, s), 5.19 (1H, d, J = 7.0 Hz), 5.89 (1H, d, J = 2.1 Hz), 6.85 (2H, d, J = 8.5 Hz), 7.25-7.19 (3H, m). |
| I-074 | 1H-NMR (CDCl3) δ: 1.02 (6H, d, J = 6.8 Hz), 1.51-1.46 (2H, m), 1.61-1.70 (2H, m), 1.75 (2H, br s), 1.83-1.89 (2H, m), 1.94-2.02 (2H, m), 2.04-2.12 (1H, m), 2.49 (3H, s), 2.86 (2H, s), 3.71 (2H, t, J = 5.3 Hz), 3.84 (3H, s), 4.27 (2H, s), 4.47-4.58 (1H, m), 4.48 (2H, s), 5.09 (1H, d, J = 7.4 Hz), 5.93 (1H, d, J = 2.1 Hz), 6.85 (2H, d, J = 8.5 Hz), 7.21 (3H, dd, J = 14.4, 5.3 Hz). |
| I-076 | 1H-NMR (CDCl3) δ: 1.02 (6H, d, J = 6.8 Hz), 1.33-1.42 (2H, br m), 1.63-1.70 (2H, br m), 1.73-1.82 (1H, m), 1.82-1.91 (3H, m), 2.03-2.10 (5H, m), 2.36-2.38 (2H, m), 2.47-2.55 (1H, m), 2.66 (2H, br s), 3.66 (1H, br s), 3.71 (2H, d, J = 6.7 Hz), 3.84 (3H, s), 4.27 (2H, s), 4.47 (2H, s), 5.26 (1H, br s), 5.91 (1H, d, J = 2.0 Hz), 6.85 (2H, d, J = 8.7 Hz), 7.21 (3H, dd, J = 12.4, 5.3 Hz). |
| I-077 | 1H-NMR (CDCl3) δ: 1.02 (6H, d, J = 6.8 Hz), 1.46 (2H, m), 1.94 (2H, m), 2.07 (1H, septd, J = 6.8, 6.5 Hz), 2.12 (2H, m), 2.26 (3H, s), 2.41 (3H, s), 2.70 (2H, m), 3.67 (1H, m), 3.70 (2H, d, J = 6.5 Hz), 4.16 (2H, s), 4.43 (2H, s), 5.60 (1H, brs), 6.84 (2H, m), 7.18 (2H, m), 7.21 (1H, s). |
| I-078 | 1H-NMR (CDCl3) δ: 1.02 (6H, d, J = 6.7 Hz), 1.75-1.89 (2H, m), 2.02-2.28 (3H, m), 2.30 (3H, s), 2.41 (3H, s), 2.86 (1H, m), 3.14 (1H, m), 3.70 (2H, d, J = 6.5 Hz), 3.84 (1H, m), 4.16 (1H, d, J = 16.3 Hz), 4.22 (1H, d, J = 16.3 Hz), 4.43 (1H, d, J = 15.7 Hz), 4.46 (1H, d, J = 15.7 Hz), 4.72 (1H, d, J = 49.4 Hz), 5.95 (1H, brs), 6.84 (2H, m), 7.18 (2H, m), 7.23 (1H, s). |
| I-079 | 1H-NMR (CDCl3) δ: 7.23 (1H, d, J = 2.1 Hz), 7.21 (2H, d, J = 8.7 Hz), 6.85 (2H, d, J = 8.7 Hz), 5.89 (1H, d, J = 2.1 Hz), 5.40 (1H, d, J = 7.0 Hz), 4.49 (2H, s), 4.26 (2H, s), 3.84 (3H, s), 3.80-3.70 (3H, m), 3.02-2.98 (2H, m), 2.71-2.64 (2H, m), 2.13-2.03 (1H, m), 1.92-1.88 (2H, m), 1.60-1.58 (1H, m), 1.30-1.19 (2H, m), 1.03 (3H, s), 1.01 (3H, s). |

TABLE 30

| Compound No. | NMR |
|---|---|
| I-080 | 1H-NMR (CDCl3) δ: 7.24 (1H, s), 7.18 (2H, d, J = 8.5 Hz), 6.85 (2H, d, J = 8.5 Hz), 5.88 (1H, d, J = 7.0 Hz), 4.64 (1H, d, J = 50.4 Hz), 4.45 (2H, s), 4.23-4.17 (2H, m), 4.02-3.87 (1H, m), 3.71 (2H, d, J = 6.5 Hz), 3.29 (1H, t, J = 12.2 Hz), 3.09 (1H, dt, J = 12.2, 2.0 Hz), 2.79 (1H, dd, J = 39.0, 12.2 Hz), 2.67 (1H, t, J = 12.2 Hz), 2.42 (3H, s), 2.10-2.05 (1H, m), 1.75 (1H, dt, J = 12.2, 2.0 Hz), 1.60-1.54 (2H, m), 1.03 (3H, s), 1.01 (3H, s). |
| I-081 | 1H-NMR (CDCl3) δ: 1.02 (6H, d, J = 6.7 Hz), 1.69-1.75 (2H, br m), 1.91-1.97 (2H, br m), 2.02-2.12 (1H, m), 2.25 (5H, br s), 2.25 (3H, s), 2.43 (3H, s), 2.55 (2H, br s), 3.70 (2H, d, J = 8.0 Hz), 4.20-4.29 (2H, br m), 4.47 (2H, d, J = 9.2 Hz), 4.77 (1H, br s), 6.84 (2H, d, J = 8.0 Hz), 7.14-7.23 (2H, br m), 7.40 (1H, br s). |
| I-083 | 1H-NMR (CDCl3) δ: 1.02 (6H, d, J = 6.8 Hz), 1.75 (2H, br s), 1.95 (2H, br s), 2.02-2.11 (1H, m), 2.23-2.26 (8H, br m), 2.58 (2H, s), 3.70 (2H, d, J = 6.7 Hz), 3.73 (3H, s), 4.27-4.38 (4H, br m), 4.79 (1H, tt, J = 10.2, 4.0 Hz), 5.87-5.96 (1H, br m), 6.83 (2H, d, J = 8.4 Hz), 7.19 (2H, dd, J = 30.0, 7.5 Hz). |

TABLE 30-continued

| Compound No. | NMR |
|---|---|
| I-084 | 1H-NMR (CDCl3) δ: 1.02 (6H, d, J = 6.7 Hz), 1.70-1.79 (2H, br m), 1.92-1.99 (2H, br m), 2.03-2.13 (1H, br m), 2.26 (5H, br s), 2.57 (2H, s), 3.71 (2H, d, J = 6.8 Hz), 4.15 (3H, s), 4.37-4.45 (4H, br m), 4.77-4.83 (1H, br m), 6.85 (2H, d, J = 8.5 Hz), 7.12-7.24 (2H, br m), 7.48-7.34 (1H, br m). |
| I-085 | 1H-NMR (CDCl3) δ: 1.02 (7H, d, J = 6.7 Hz), 1.75 (2H, br s), 1.94 (2H, s), 2.03-2.13 (1H, m), 2.20-2.29 (8H, br m), 2.55 (2H, br s), 3.71 (2H, d, J = 6.5 Hz), 4.18 (2H, s), 4.34 (2H, s), 4.78 (1H, br s), 5.74 (1H, s), 5.90 (1H, t, J = 2.6 Hz), 6.86 (2H, d, J = 8.5 Hz), 7.14 (2H, d, J = 8.2 Hz), 8.62 (1H, br s). |
| I-087 | 1H-NMR (CDCl3) δ: 7.24 (1H, s), 7.01 (1H, dd, J = 11.9, 1.9 Hz), 6.95 (1H, dd, J = 8.3, 1.9 Hz), 6.89 (1H, t, J = 8.3 Hz), 5.77 (1H, d, J = 6.3 Hz), 4.42 (2H, s), 4.14 (2H, s), 4.01 (2H, t, J = 6.5 Hz), 3.68 (1H, br s), 2.71 (2H, br s), 2.42 (3H, s), 2.27 (3H, s), 2.14-2.11 (2H, m), 1.98-1.95 (2H, m), 1.81-1.76 (2H, m), 1.53-1.46 (4H, m), 0.98 (3H, t, J = 7.4 Hz). |
| I-088 | 1H-NMR (CDCl3) δ: 7.25 (1H, s), 7.22 (2H, d, J = 7.0 Hz), 6.89 (2H, d, J = 7.0 Hz), 5.75 (1H, d, J = 5.6 Hz), 4.46 (2H, s), 4.41 (2H, td, J = 12.3, 1.0 Hz), 4.13 (2H, s), 3.68 (1H, br s), 2.71 (2H, br s), 2.42 (3H, s), 2.27 (3H, s), 2.13-2.10 (2H, m), 1.97-1.94 (2H, m), 1.51-1.44 (2H, m). |
| I-089 | 1H-NMR (CDCl3) δ: 0.25-0.29 (1H, m), 0.37-0.40 (1H, m), 0.49-0.54 (2H, m), 0.92-1.03 (3H, m), 1.42-1.54 (2H, m), 1.74-1.78 (2H, m), 1.90-1.94 (1H, m), 2.23 (2H, s), 2.42 (2H, s), 3.60 (1H, br s), 3.95 (2H, t, J = 6.5 Hz), 4.16 (2H, s), 4.38-4.47 (2H, m), 5.77 (1H, br s), 6.81-6.90 (2H, m), 7.14-7.23 (3H, m). |
| I-090 | 1H-NMR (CDCl3) δ: 0.25-0.31 (1H, m), 0.38-0.41 (1H, m), 0.51-0.58 (2H, m), 0.95-1.01 (3H, m), 1.45-1.57 (2H, m), 1.74-1.84 (2H, m), 1.88-2.01 (1H, m), 2.25 (2H, s), 2.43 (2H, s), 3.60 (1H, br s), 3.98-4.05 (2H, m), 4.07-4.18 (2H, m), 4.35-4.46 (2H, m), 5.95 (1H, s), 6.85-7.04 (3H, m), 7.22-7.26 (1H, m). |
| I-091 | 1H-NMR (CDCl3) δ: 0.26-0.34 (1H, m), 0.35-0.44 (1H, m), 0.49-0.64 (2H, m), 0.93-1.02 (3H, m), 1.43-1.54 (2H, m), 1.71-1.81 (2H, m), 1.89-2.00 (1H, m), 2.26 (2H, s), 2.42 (2H, s), 3.62 (1H, br s), 3.90-3.96 (2H, m), 4.08-4.18 (2H, m), 4.39-4.51 (5H, m), 6.04 (1H, br s), 6.54-6.62 (1H, m), 6.65-6.68 (1H, m), 7.26-7.32 (4H, m). |

TABLE 31

| Compound No. | NMR |
|---|---|
| I-092 | 1H-NMR (CDCl3) δ: 1.02 (6H, d, J = 6.7 Hz), 1.72-1.83 (2H, br m), 1.93-2.00 (2H, br m), 2.04-2.13 (1H, m), 2.24-2.28 (5H, br m), 2.53-2.64 (2H, br m), 3.62 (3H, s), 3.71 (2H, d, J = 6.5 Hz), 4.16-4.26 (2H, br m), 4.36 (2H, d, J = 7.0 Hz), 4.80 (1H, br s), 6.05 (1H, d, J = 16.8 Hz), 6.49 (1H, d, J = 28.0 Hz), 6.53 (1H, s), 6.85 (2H, d, J = 8.3 Hz), 7.16 (2H, dd, J = 23.2, 6.9 Hz). |
| I-093 | 1H-NMR (CDCl3) δ: 1.02 (6H, d, J = 6.7 Hz), 1.67-1.80 (2H, br m), 1.91-2.10 (3H, m), 2.24-2.34 (5H, br m), 2.46-2.58 (2H, br m), 3.70 (2H, d, J = 6.5 Hz), 4.45 (2H, d, J = 6.3 Hz), 4.52 (2H, d, J = 14.7 Hz), 4.81 (1H, br s), 6.83 (2H, d, J = 8.5 Hz), 7.21-7.12 (2H, m), 7.36-7.27 (2H, m), 8.39 (1H, d, J = 2.8 Hz). |
| I-094 | 1H-NMR (CDCl3) δ: 1.72-1.79 (2H, br m), 1.93-2.02 (2H, br m), 2.24-2.28 (5H, br m), 2.53-2.64 (2H, br m), 3.62 (3H, s), 3.80 (3H, s), 4.17-4.25 (2H, br m), 4.37 (2H, d, J = 7.3 Hz), 4.80 (1H, br s), 6.05 (1H, d, J = 15.8 Hz), 6.53-6.45 (2H, br m), 6.86 (2H, d, J = 8.5 Hz), 7.18 (2H, dd, J = 22.8, 7.5 Hz). |
| I-095 | 1H-NMR (CDCl3) δ: 1.70-1.76 (2H, br m), 1.92-1.97 (2H, br m), 2.25 (5H, br s), 2.43 (3H, s), 2.56 (2H, br s), 3.80 (3H, s), 4.21-4.28 (2H, br m), 4.48 (2H, d, J = 11.5 Hz), 4.78 (1H, br s), 6.86 (2H, d, J = 8.7 Hz), 7.20 (2H, dd, J = 23.1, 6.7 Hz), 7.41 (1H, s). |
| I-096 | 1H-NMR (CDCl3) δ: 0.21-0.26 (1H, m), 0.36-0.37 (2H, m), 0.44-0.50 (1H, m), 0.98 (3H, t, J = 7.4 Hz), 1.46-1.55 (2H, m), 1.78-1.82 (2H, m), 1.87-1.91 (1H, m), 2.11 (2H, s), 2.23 (3H, s), 3.58 (1H, br s), 4.01-4.03 (2H, m), 4.14 (3H, s), 4.40-4.44 (4H, m), 4.91 (1H, br s), 6.90-7.05 (4H, m). |
| I-097 | 1H-NMR (CDCl3) δ: 0.25-0.27 (1H, m), 0.41-0.43 (2H, m), 0.46-0.51 (1H, m), 0.96-0.98 (3H, m), 1.44-1.50 (2H, m), 1.73-1.80 (2H, m), 1.88-1.92 (1H, m), 2.24 (3H, s), 2.43 (2H, br s), 3.60 (1H, br s), 3.90-3.97 (2H, m), 4.14 (3H, s), 4.36-4.52 (4H, m), 5.02 (1H, br s), 6.61-6.67 (2H, m), 7.22-7.25 (2H, m). |
| I-098 | 1H-NMR (CDCl3) δ: 0.17-0.22 (1H, m), 0.33-0.36 (2H, m), 0.43-0.48 (1H, m), 0.96-0.98 (3H, m), 1.26 (3H, t, J = 7.2 Hz), 1.47-1.51 (2H, m), 1.74-1.78 (2H, m), 1.85-1.89 (1H, m), 2.05 (3H, s), 2.21 (3H, s), 2.39 (2H, s), 3.92-3.98 (2H, m), 4.10-4.15 (4H, m), 4.41-4.47 (4H, m), 4.83 (1H, br s), 6.85-6.90 (2H, m), 7.15-7.17 (2H, m), 7.23 (1H, s). |
| I-099 | 1H-NMR (CDCl3) δ: 0.92-1.05 (3H, m), 1.18-1.41 (3H, m), 1.42-1.56 (2H, m), 1.69-1.86 (4H, m), 1.88-2.14 (3H, m), 2.27-2.32 (4H, m), 2.41-2.43 (4H, m), 2.86-2.91 (2H, m), 3.94-3.96 (2H, m), 4.23 (1H, s), 4.38 (1H, s), 4.56 (2H, d, J = 6.7 Hz), 6.82-6.88 (2H, m), 7.07 (1H, d, J = 8.5 Hz), 7.16 (1H, d, J = 8.7 Hz), 7.24 (0.5H, s), 7.43 (0.5H, s). |
| I-100 | 1H-NMR (CDCl3) δ: 0.98 (3H, t, J = 7.4 Hz), 1.32-1.44 (2H, m), 1.45-1.56 (2H, m), 1.77-1.84 (2H, m), 1.87-1.96 (2H, m), 2.04-2.14 (2H, m), 2.25 (3H, s), 2.61-2.75 (2H, m), 3.66-3.68 (1H, m), 4.02 (2H, t, J = 6.5 Hz), 4.14 (3H, s), 4.40 (2H, s), 4.42 (2H, s), 4.86 (1H, d, J = 7.5 Hz), 6.87-7.02 (3H, m), 7.28 (1H, s). |
| I-101 | 1H-NMR (CDCl3) δ: 1.03 (6H, d, J = 6.8 Hz), 1.29-1.41 (2H, m), 1.85-1.94 (2H, m), 2.02-2.14 (3H, m), 2.24 (3H, s), 2.56-2.73 (2H, m), 3.62-3.72 (1H, m), 3.70 (2H, d, J = 6.5 Hz), |

TABLE 31-continued

| Compound No. | NMR |
|---|---|
| | 4.13 (3H, s), 4.42 (2H, s), 4.44 (2H, s), 4.79 (1H, d, J = 7.5 Hz), 6.86 (2H, d, J = 8.7 Hz), 7.15 (2H, d, J = 8.7 Hz), 7.26 (1H, s). |

TABLE 32

| Compound No. | NMR |
|---|---|
| I-102 | 1H-NMR (CDCl3) δ: 0.98 (3H, t, J = 7.3 Hz), 1.35-1.54 (4H, m), 1.71-1.81 (2H, m), 1.88-1.96 (2H, m), 2.04-2.14 (2H, m), 2.26 (3H, s), 2.64-2.76 (2H, m), 3.61-3.72 (1H, m), 3.93 (2H, t, J = 6.5 Hz), 4.14 (3H, s), 4.41 (2H, s), 4.45 (2H, s), 4.97 (1H, d, J = 7.2 Hz), 6.58-6.69 (2H, m), 7.22 (1H, t, J = 8.7 Hz), 7.30 (1H, s). |
| I-103 | 1H-NMR (CDCl3) δ: 0.18-0.22 (1H, m), 0.32-0.37 (2H, m), 0.44-0.48 (1H, m), 1.02 (7H, d, J = 6.8 Hz), 1.26 (2H, t, J = 7.1 Hz), 1.85-1.89 (1H, m), 2.03-2.11 (3H, m), 2.20 (3H, s), 3.65-3.67 (2H, m), 3.71 (2H, d, J = 6.5 Hz), 4.13-4.16 (3H, m), 4.44 (4H, t, J = 5.5 Hz), 4.82 (1H, br s), 6.86-6.88 (2H, m), 7.16 (2H, d, J = 8.5 Hz), 7.23 (1H, s). |
| I-104 | 1H-NMR (CDCl3) δ: 1.47-1.56 (2H, br m), 1.95-1.99 (2H, br m), 2.11-2.14 (2H, m), 2.28 (3H, s), 2.35-2.38 (2H, m), 2.42 (3H, s), 2.74-2.77 (2H, br m), 2.83-2.87 (2H, m), 3.67-3.68 (1H, br m), 4.15 (2H, s), 4.51 (2H, s), 5.95 (1H, d, J = 5.5 Hz), 6.88 (1H, dd, J = 10.8, 1.4 Hz), 6.95 (1H, dd, J = 7.8, 1.4 Hz), 7.29 (1H, s), 7.35 (1H, dd, J = 7.9, 7.8 Hz). |
| I-105 | 1H-NMR (CDCl3) δ: 1.46-1.51 (2H, br m), 1.94-1.97 (2H, br m), 2.11-2.13 (2H, br m), 2.27 (3H, s), 2.34-2.40 (2H, m), 2.42 (3H, s), 2.69-2.75 (2H, m), 2.84-2.88 (2H, m), 3.67-3.71 (1H, m), 4.16 (2H, s), 4.48 (2H, s), 5.70 (1H, d, J = 4.5 Hz), 7.15 (2H, d, J = 8.2 Hz), 7.20 (1H, s), 7.22 (2H, d, J = 8.0 Hz). |
| I-106 | 1H-NMR (CDCl3) δ: 0.97-0.99 (3H, m), 1.46-1.52 (2H, m), 1.74-1.78 (2H, m), 2.28 (3H, d, J = 1.8 Hz), 2.42 (7H, d, J = 7.9 Hz), 3.22 (1H, s), 3.36 (1H, s), 3.95 (2H, dd, J = 12.0, 6.4 Hz), 4.34 (1H, s), 4.42 (1H, s), 4.54 (1H, s), 4.67 (1H, s), 6.85 (2H, dd, J = 17.3, 8.6 Hz), 7.15 (2H, t, J = 8.6 Hz), 7.42 (0.5H, s). |
| I-107 | 1H-NMR (CDCl3) δ: 0.94 (3H, t, J = 7.3 Hz), 1.45-1.53 (2H, m), 1.57-1.66 (2H, m), 1.94-1.98 (2H, m), 2.13 (2H, t, J = 10.1 Hz), 2.27 (3H, s), 2.42 (3H, s), 2.59 (2H, t, J = 7.5 Hz), 2.71 (2H, br), 3.70 (1H, br), 4.15 (2H, s), 4.46 (2H, s), 5.76 (1H, br), 6.91-6.97 (2H, m), 7.11 (2H, t, J = 7.7 Hz), 7.23 (1H, s). |
| I-109 | 1H-NMR (CDCl3) δ: 0.98 (3H, t, J = 7.4 Hz), 1.31-1.42 (2H, m), 1.50 (2H, td, J = 14.9, 7.4 Hz), 1.72-1.81 (2H, m), 1.85-1.94 (2H, m), 2.03-2.14 (2H, m), 2.23 (3H, s), 2.57-2.71 (2H, m), 3.60-3.71 (1H, m), 3.95 (2H, t, J = 6.5 Hz), 4.36 (2H, s), 4.45 (2H, s), 4.91 (1H, d, J = 6.7 Hz), 6.60 (1H, t, J = 52.6 Hz), 6.85 (2H, d, J = 8.6 Hz), 7.15 (2H, d, J = 8.6 Hz), 7.49 (1H, s). |
| I-110 | 1H-NMR (CDCl3) δ: 0.95-1.04 (7H, m), 1.40-1.55 (4H, m), 1.72-1.80 (2H, m), 1.91-1.98 (2H, m), 1.98-2.03 (1H, m), 2.06-2.16 (2H, m), 2.26 (3H, s), 2.67-2.77 (2H, m), 3.62-3.72 (1H, m), 3.94 (2H, t, J = 6.5 Hz), 4.11 (2H, s), 4.42 (2H, s), 5.75 (1H, s), 6.84 (2H, d, J = 8.6 Hz), 7.12 (1H, s), 7.18 (2H, d, J = 8.6 Hz). |
| I-111 | 1H-NMR (CDCl3) δ: 1.00-1.05 (4H, m), 1.42-1.54 (2H, m), 1.92-2.03 (3H, m), 2.07-2.17 (2H, m), 2.27 (3H, s), 2.70-2.79 (2H, m), 3.62-3.73 (1H, m), 4.09 (2H, s), 4.34 (2H, q, J = 8.2 Hz), 4.44 (2H, s), 5.86 (1H, br s), 6.89 (2H, d, J = 8.7 Hz), 7.14 (1H, s), 7.23 (2H, d, J = 8.7 Hz). |
| I-113 | 1H-NMR (CDCl3) δ: 0.97 (3H, t, J = 7.4 Hz), 1.43-1.56 (4H, m), 1.71-1.79 (2H, m), 1.92-2.00 (2H, m), 2.07-2.19 (2H, m), 2.28 (3H, s), 2.41 (3H, s), 2.70-2.81 (2H, m), 3.61-3.75 (1H, m), 3.93 (2H, t, J = 6.5 Hz), 4.15 (2H, s), 4.46 (2H, s), 5.86 (1H, s), 6.58 (1H, dd, J = 12.0, 2.4 Hz), 6.65 (1H, dd, J = 8.5, 2.4 Hz), 7.28 (1H, s), 7.30 (1H, t, J = 7.9 Hz). |

TABLE 33

| Compound No. | NMR |
|---|---|
| I-114 | 1H-NMR (CDCl3) δ: 0.93 (3H, t, J = 7.3 Hz), 1.47-1.54 (2H, m), 1.60-1.64 (2H, m), 1.95-1.98 (2H, br m), 2.11-2.16 (2H, br m), 2.28 (3H, s), 2.41 (3H, s), 2.56 (2H, t, J = 7.6 Hz), 2.73-2.76 (2H, br m), 3.67-3.68 (1H, br m), 4.17 (2H, s), 4.50 (2H, s), 5.86 (1H, d, J = 5.5 Hz), 6.85 (1H, dd, J = 11.2, 1.4 Hz), 6.92 (1H, dd, J = 7.8, 1.4 Hz), 7.26 (1H, s), 7.29 (1H, d, J = 7.9 Hz). |
| I-115 | 1H-NMR (CDCl3) δ: 1.03 (6H, d, J = 6.7 Hz), 1.44-1.53 (2H, m), 1.94-1.98 (2H, m), 2.07-2.17 (3H, m), 2.27 (3H, s), 2.42 (3H, s), 2.59 (2H, t, J = 7.5 Hz), 2.72 (2H, br), 3.68 (1H, br), 3.77 (2H, d, J = 6.5 Hz), 4.13 (2H, s), 4.42 (2H, s), 5.76 (1H, br), 6.88 (1H, t, J = 8.3 Hz), 6.95 (1H, d, J = 8.3 Hz), 7.01 (1H, dd, J = 11.9, 1.8 Hz). |
| I-116 | 1H-NMR (CDCl3) δ: 1.04 (6H, d, J = 6.7 Hz), 1.32-1.43 (2H, m), 1.90-1.94 (2H, m), 2.07-2.17 (3H, m), 2.25 (3H, s), 2.67 (2H, br), 3.67 (1H, br), 3.77 (2H, d, J = 6.5 Hz), 4.13 (3H, s), 4.40 (2H, s), 4.42 (2H, s), 4.86 (1H, d, J = 7.2 Hz), 6.87-6.95 (2H, m), 6.99 (1H, d, J = 12 Hz), 7.28 (1H, s). |

TABLE 33-continued

| Compound No. | NMR |
|---|---|
| I-117 | 1H-NMR (CDCl3) δ: 1.02 (6H, d, J = 6.7 Hz), 1.45-1.54 (2H, m), 1.94-1.98 (2H, m), 2.02-2.15 (3H, m), 2.27 (3H, s), 2.41 (3H, s), 2.74 (2H, br), 3.67 (1H, br), 3.68 (2H, d, J = 6.5 Hz), 4.15 (2H, s), 4.46 (2H, s), 5.85 (1H, br), 6.58 (1H, dd, J = 12.0, 2.4 Hz), 6.65 (1H, dd, J = 8.5, 2.4 Hz), 7.28-7.32 (2H, m). |
| I-118 | 1H-NMR (CDCl3) δ: 1.02 (6H, d, J = 6.8 Hz), 1.37-1.46 (2H, m), 1.91-1.95 (2H, m), 2.04-2.14 (3H, m), 2.26 (3H, s), 2.41 (3H, s), 2.71 (2H, br), 3.69 (1H, br), 3.69 (2H, d, J = 6.5 Hz), 4.14 (3H, s), 4.41 (2H, s), 4.45 (2H, s), 4.98 (1H, br), 6.61 (1H, dd, J = 12.0, 2.3 Hz), 6.66 (1H, dd, J = 8.5, 2.3 Hz), 7.23 (1H, t, J = 8.7 Hz), 7.31 (1H, s). |
| I-119 | 1H-NMR (CDCl3) δ: 0.98 (3H, t, J = 7.4 Hz), 1.34-1.45 (2H, m), 1.45-1.55 (2H, m), 1.72-1.81 (2H, m), 1.88-1.97 (2H, m), 2.05-2.16 (2H, m), 2.24 (3H, s), 2.61-2.73 (2H, m), 3.60-3.74 (1H, m), 3.95 (2H, t, J = 6.5 Hz), 4.30 (2H, s), 4.44 (2H, s), 5.18 (1H, s), 5.33 (2H, d, J = 47.4 Hz), 6.85 (2H, d, J = 8.5 Hz), 7.17 (2H, d, J = 8.5 Hz), 7.41 (1H, s). |
| I-120 | 1H-NMR () δ: 1.03 (6H, d, J = 6.8 Hz), 1.34-1.46 (2H, m), 1.87-1.96 (2H, m), 2.01-2.14 (4H, m), 2.24 (3H, s), 2.58-2.73 (2H, m), 3.61-3.71 (1H, m), 3.70 (2H, d, J = 6.7 Hz), 4.30 (2H, s), 4.44 (2H, s), 5.15 (1H, s), 5.33 (2H, d, J = 47.4 Hz), 6.85 (2H, d, J = 8.6 Hz), 7.17 (2H, d, J = 8.6 Hz), 7.41 (1H, s). |
| I-121 | 1H-NMR (CDCl3) δ: 1.48-1.55 (2H, br m), 1.95-1.99 (2H, br m), 2.11-2.14 (2H, br m), 2.28 (3H, s), 2.42 (3H, s), 2.75-2.77 (2H, br m), 3.66-3.67 (1H, br m), 4.13 (2H, s), 4.39 (2H, t, J = 12.2 Hz), 4.48 (2H, s), 5.98-6.00 (1H, br m), 6.66-6.70 (2H, m), 7.31 (1H, s), 7.40 (1H, dd, J = 8.6, 8.6 Hz). |
| I-122 | 1H-NMR (CDCl3) δ: 1.39-1.46 (2H, br m), 1.92-1.95 (2H, br m), 2.08-2.11 (2H, br m), 2.27 (3H, s), 2.71-2.73 (2H, br m), 3.63-3.70 (1H, br m), 4.14 (3H, s), 4.37-4.43 (4H, m), 4.49 (2H, s), 5.03 (1H, d, J = 7.2 Hz), 6.67-6.73 (2H, m), 7.32-7.34 (2H, m). |
| I-123 | 1H-NMR (CDCl3) δ: 0.92-1.04 (3H, m), 1.13-1.34 (2H, m), 1.42-1.59 (2H, m), 1.59-1.85 (5H, m), 1.86-2.00 (3H, m), 2.18-2.32 (4H, m), 2.35-2.49 (4H, m), 2.81 (2H, t, J = 12.1 Hz), 3.94-4.09 (2H, m), 4.24 (1H, s), 4.38 (1H, s), 4.54 (1H, s), 4.57 (1H, s), 6.84-7.00 (3H, m), 7.45 (0.5H, s). |

TABLE 34

| Compound No. | NMR |
|---|---|
| I-124 | 1H-NMR (CDCl3) δ: 0.94-1.06 (3H, m), 1.35-1.69 (5H, m), 1.71-2.16 (6H, m), 2.22-2.31 (3H, m), 2.37-2.47 (3H, m), 2.79-2.97 (2H, m), 3.94-4.09 (2H, m), 4.15-4.77 (4H, m), 4.77-5.16 (1H, m), 6.75-7.06 (3H, m), 7.34 (0.5H, s), 7.45 (0.5H, s). |
| I-125 | 1H-NMR (CDCl3) δ: 0.94-1.00 (3H, m), 1.16-1.37 (2H, m), 1.75-1.84 (2H, m), 2.27-2.52 (5H, m), 2.76-2.93 (2H, m), 2.95-3.10 (2H, m), 3.96-4.07 (2H, m), 4.22 (1H, s), 4.39 (1H, s), 4.53 (1H, s), 4.56 (1H, s), 6.84-7.00 (3H, m), 7.29 (0.5H, s), 7.46 (0.5H, s). |
| I-126 | 1H-NMR (CDCl3) δ: 0.90-1.04 (3H, m), 1.40-1.88 (5H, m), 2.22-2.33 (3H, m), 3.20 (1H, s), 3.37 (1H, s), 3.98-4.07 (2H, m), 4.34 (1H, s), 4.44 (1H, s), 4.52 (1H, s), 4.68 (1H, s), 6.76-7.10 (3H, m), 7.30 (0.5H, s), 7.43 (0.5H, s). |
| I-127 | 1H-NMR (CDCl3) δ: 0.94-1.03 (3H, m), 1.04-1.17 (2H, m), 1.34-1.84 (9H, m), 2.33-2.61 (8H, m), 3.03 (2H, t, J = 13.1 Hz), 3.97-4.09 (2H, m), 4.24 (1H, s), 4.38 (1H, s), 4.53 (1H, s), 4.58 (1H, s), 6.79-7.05 (3H, m), 7.28 (0.5H, s), 7.45 (0.5H, s). |

The following is a description of biological test examples of the compound according to the present invention. In the biological test of the compound according to the present invention, the test procedure described in the following biological test examples or essentially the same test procedure can be used.

The compound represented by Formula (I), Formula (I'), or Formula (II') according to the present invention may have serotonin 5-HT2A receptor antagonism and/or inverse agonism, and may antagonize the human serotonin 5-HT2A receptor.

The compound represented by Formula (I), Formula (I'), or Formula (II') according to the present invention may have serotonin 5-HT2A and 5-HT2C receptor antagonism and/or inverse agonism, and may antagonize the human serotonin 5-HT2A and 5-HT2C receptors.

Specifically, in the evaluation method described below, the Ki value is preferably 5000 nM or less, more preferably 1000 nM or less, and even more preferably 100 nM or less.

Test Example 1: 5-HT2A Receptor Binding Inhibition Test (Each Experimental Condition)

Cell membrane: Jump-In HEK cell membrane (expressing human recombinant 5-HT2A receptor)

Assay buffer: Tris-HCl 50 mmol/L (pH 7.4) containing NaCl 120 mmol/L, $MgCl_2 \cdot 6H_2O$ 1 mmol/L, KCl 5 mmol/L, 0.1% BSA, and $CaCl_2$ 2 mmol/L Radioactive ligand: [$^3$H]-Ketanserin around Kd value calculated by the following method Non-specific ligand: Serotonin HCl The Kd value was calculated when the lot of cell membrane was changed. In advance, 0.5 μL of a 1 mmol/L compound for non-specific binding calculation dissolved in DMSO or DMSO was dispensed into a microplate, and the cell membrane was diluted with an Assay buffer. The radioactive ligand solution was serially diluted and the count was confirmed with a liquid scintillator. Assay buffer containing diluted cell membrane was dispensed into a microplate at 50 μL/well. Then, the radioactive ligand solution was dispensed into a microplate at 50 μL/well, and the plate was sealed. It was allowed to stand at room temperature (25° C.) for 1.5 hours. During this period, 50 mmol/L Tris-HCl (pH 7.4) was dispensed into a GF/B UniFilter plate at 50 μL/well and allowed to stand at 4° C. for 1 hour or longer. After that, filtration was performed with Cell harvester (PerkinElmer). The radioactive ligand solution was dispensed into an empty well of the GF/B UniFilter plate at 10 μL/well. After the GF/B UniFilter plate was dried at room temperature, MicroScinti 20 was dispensed into the GF/B UniFilter plate at 50 μL/well, and the plate was sealed. The GF/B UniFilter plate was allowed to stand overnight at room temperature. The radioactivity of [$^3$H]-Ketanserin bound to the 5-HT2A receptor was measured using Microbeta2 (PerkinElmer) at a measurement time of 1 min/well. The Saturation curve was drawn from the measured value, and the Kd value was calculated from the slope of the Scatchard Plot.

(Binding Test of the Compound According to the Present Invention)

In advance, 0.5 μL of the compound solution dissolved in DMSO was dispensed into a microplate, and the cell membrane and the hot ligand were diluted with Assay buffer, respectively. Then, the Assay buffer containing the diluted cell membrane was dispensed into a microplate at 50 μL/well. Then, the radioactive ligand solution was dispensed into a microplate at 50 μL/well, and the plate was sealed. Then, it was allowed to stand at room temperature (25° C.) for 1.5 hours. During this period, 50 mmol/L Tris-HCl (pH 7.4) was dispensed into a GF/B UniFilter plate at 50 μL/well and allowed to stand at 4° C. for 1 hour or longer. After that, filtration was performed with Cell harvester (PerkinElmer). After the GF/B UniFilter plate was dried at room temperature, MicroScinti 20 was dispensed into the GF/B UniFilter plate at 50 μL/well, and the plate was sealed. The GF/B UniFilter plate was allowed to stand overnight at room temperature. The radioactivity of [$^3$H]-Ketanserin bound to the 5-HT2A receptor was measured using Microbeta2 (PerkinElmer) at a measurement time of 1 min/well. The non-specific binding was calculated from the radioactivity of [$^3$H]-Ketanserin in the presence of 500 μmol/L Serotonin HCl with the unlabeled ligand, and the total binding was calculated from the radioactivity of [$^3$H]-Ketanserin in the absence of the compound according to the present invention (Vehicle). Finally, the Ki value was calculated from the dose-response curve.

(The binding activity of the compound according to the present invention was calculated from the following binding inhibition rate (%).)

$$\text{Inhibition rate (\%)}=[1-(c-a)/(b-a)]\times 100$$

a; mean cpm of non-specific binding
b; mean cpm of total binding
c; cpm in the presence of the test compound (Results)

The evaluation results regarding the human serotonin 5-HT2A receptor binding activity of the compound according to the present invention are shown below. In the table shown below, "A" means that the Ki value is less than 10 nM, "B" means that the Ki value is 10 nM or more and less than 100 nM, and "C" means that the Ki value is 100 nM or more and 5000 nM or less.

Compound I-003: 9.93 nM
Compound I-004: 4.51 nM
Compound I-006: 0.968 nM
Compound I-012: 6.02 nM
Compound I-015: 45.5 nM
Compound I-029: 4.33 nM
Compound I-030: 2.17 nM
Compound I-031: 0.709 nM
Compound I-033: 4.01 nM
Compound I-037: 4.70 nM
Compound I-043: 2.14 nM
Compound I-046: 3.09 nM
Compound I-084: 2.61 nM
Compound I-086: 0.503 nM
Compound I-101: 0.683 nM
Compound I-102: 0.642 nM
Compound I-103: 1.89 nM
Compound I-104: 0.952 nM
Compound I-107: 0.549 nM
Compound I-109: 0.430 nM
Compound I-110: 0.537 nM
Compound I-117: 0.820 nM
Compound I-118: 1.03 nM
Compound I-122: 0.824 nM
Compound I-123: 0.506 nM
Compound I-126: 1.24 nM

TABLE 35

| Compound No. | h-5-HT2A Ki |
|---|---|
| I-001 | A |
| I-002 | A |
| I-005 | A |
| I-007 | A |
| I-008 | A |
| I-009 | A |
| I-010 | B |
| I-011 | C |
| I-013 | B |
| I-014 | A |
| I-016 | A |
| I-017 | A |
| I-018 | B |
| I-019 | B |
| I-020 | B |
| I-021 | A |
| I-022 | B |
| I-023 | A |
| I-024 | A |
| I-025 | B |
| I-026 | B |
| I-027 | C |
| I-028 | A |
| I-032 | B |
| I-034 | A |
| I-035 | A |
| I-036 | B |
| I-038 | B |
| I-039 | B |
| I-040 | A |
| I-041 | B |
| I-042 | A |
| I-044 | A |
| I-045 | A |
| I-047 | B |
| I-048 | A |
| I-049 | A |
| I-050 | A |
| I-051 | C |
| I-052 | B |
| I-053 | C |
| I-054 | A |
| I-055 | B |
| I-056 | B |
| I-057 | C |

TABLE 36

| Compound No. | h-5-HT2A Ki |
|---|---|
| I-058 | B |
| I-059 | B |
| I-060 | B |
| I-061 | A |
| I-062 | B |
| I-063 | B |
| I-064 | A |
| I-065 | A |
| I-066 | B |
| I-067 | A |
| I-068 | B |
| I-069 | A |
| I-070 | B |
| I-071 | C |
| I-072 | C |
| I-073 | C |
| I-074 | A |
| I-075 | B |
| I-076 | A |
| I-077 | A |
| I-078 | A |
| I-079 | A |
| I-080 | A |
| I-081 | A |
| I-082 | B |
| I-083 | B |
| I-085 | A |
| I-087 | A |
| I-088 | A |
| I-089 | A |
| I-090 | A |
| I-091 | A |
| I-092 | A |
| I-093 | A |
| I-094 | A |
| I-095 | B |
| I-096 | A |
| I-097 | A |
| I-098 | A |
| I-099 | A |
| I-100 | A |
| I-105 | A |
| I-106 | A |
| I-108 | A |
| I-111 | A |
| I-112 | A |
| I-113 | A |
| I-114 | A |
| I-115 | A |
| I-116 | A |
| I-119 | A |
| I-120 | A |
| I-121 | A |
| I-124 | A |
| I-125 | B |
| I-127 | B |

Test Example 2:5-HT2C Receptor Binding Inhibition Test (Each Experimental Condition)

Cell membrane: Jump-In HEK cell membrane (expressing human recombinant 5-HT2C receptor)

Assay buffer: Tris-HCl 50 mmol/L (pH 7.4) containing NaCl 120 mmol/L, $MgCl_2 \cdot 6H_2O$ 1 mmol/L, KCl 5 mmol/L, 0.1% BSA, and $CaCl_2$ 2 mmol/L Radioactive ligand: [$^3$H]-Mesulergine around Kd value calculated by the following method Non-specific ligand: Serotonin HCl The Kd value was calculated when the lot of cell membrane was changed. In advance, 0.5 μL of a 1 mmol/L compound for non-specific binding calculation dissolved in DMSO or DMSO was dispensed into a microplate, and the cell membrane was diluted with an Assay buffer. The radioactive ligand solution was serially diluted and the count was confirmed with a liquid scintillator. Assay buffer containing diluted cell membrane was dispensed into a microplate at 50 μL/well. Then, the radioactive ligand solution was dispensed into a microplate at 50 μL/well, and the plate was sealed. It was allowed to stand at room temperature (25° C.) for 1.5 hours. During this period, 50 mmol/L Tris-HCl (pH 7.4) was dispensed into a GF/B UniFilter plate at 50 μL/well and allowed to stand at 4° C. for 1 hour or longer. After that, filtration was performed with Cell harvester (PerkinElmer). The radioactive ligand solution was dispensed into an empty well of the GF/B UniFilter plate at 10 μL/well. After the GF/B UniFilter plate was dried at room temperature, MicroScinti 20 was dispensed into the GF/B UniFilter plate at 50 μL/well, and the plate was sealed. The GF/B UniFilter plate was allowed to stand overnight at room temperature. The radioactivity of [$^3$H]-Mesulergine bound to the 5-HT2C receptor was measured using Microbeta2 (PerkinElmer) at a measurement time of 1 min/well. The Saturation curve was drawn from the measured value, and the Kd value was calculated from the slope of the Scatchard Plot.

(Binding Test of the Compound According to the Present Invention)

In advance, 0.5 μL of the compound solution dissolved in DMSO was dispensed into a microplate, and the cell membrane and the hot ligand were diluted with Assay buffer, respectively. Then, the Assay buffer containing the diluted cell membrane was dispensed into a microplate at 50 μL/well. Then, the radioactive ligand solution was dispensed into a microplate at 50 μL/well, and the plate was sealed. Then, it was allowed to stand at 37° C. for 2 hours. During this period, 50 mmol/L Tris-HCl (pH 7.4) was dispensed into a GF/B UniFilter plate at 50 μL/well and allowed to stand at 4° C. for 1 hour or longer. After that, filtration was performed with Cell harvester (PerkinElmer). After the GF/B UniFilter plate was dried at room temperature, MicroScinti 20 was dispensed into the GF/B UniFilter plate at 50 μL/well, and the plate was sealed. The GF/B UniFilter plate was allowed to stand overnight at room temperature. The radioactivity of [$^3$H]-Mesulergine bound to the 5-HT2C receptor was measured using Microbeta2 (PerkinElmer) at a measurement time of 1 min/well. The non-specific binding was calculated from the radioactivity of [$^3$H]-Mesulergine in the presence of 500 μmol/L Serotonin HCl with the unlabeled ligand, and the total binding was calculated from the radioactivity of [$^3$H]-Mesulergine in the absence of the compound according to the present invention (Vehicle). Finally, the Ki value was calculated from the dose-response curve.

(The binding activity of the compound according to the present invention was calculated from the following binding inhibition rate (%).)

$$\text{Inhibition rate } (\%)=[1-(c-a)/(b-a)]\times 100$$

a; mean cpm of non-specific binding b; mean cpm of total binding c; cpm in the presence of the test compound (Results)

The evaluation results regarding the human serotonin 5-HT2C receptor binding inhibitory activity of the compound according to the present invention are shown below. In the table shown below, “A” means that the Ki value is less than 10 nM, “B” means that the Ki value is 10 nM or more and less than 100 nM, and "C" means that the Ki value is 100 nM or more and 5000 nM or less.

Compound I-003: 8.39 nM
Compound I-004: 11.5 nM
Compound I-006: 2.47 nM
Compound I-012: 33.0 nM
Compound I-015: 136 nM
Compound I-029: 20.5 nM
Compound I-030: 7.76 nM
Compound I-031: 1.89 nM
Compound I-033: 28.9 nM
Compound I-037: 2.11 nM
Compound I-043: 3.07 nM
Compound I-046: 14.5 nM
Compound I-084: 5.78 nM
Compound I-086: 0.241 nM
Compound I-101: 0.461 nM
Compound I-102: 0.412 nM
Compound I-103: 0.634 nM
Compound I-104: 0.484 nM
Compound I-107: 0.340 nM
Compound I-109: 0.463 nM
Compound I-110: 0.301 nM
Compound I-117: 0.315 nM
Compound I-118: 0.371 nM
Compound I-122: 0.281 nM
Compound I-123: 1.39 nM
Compound I-126: 6.25 nM

TABLE 37

| Compound No. | h-5-HT2C Ki |
|---|---|
| I-001 | A |
| I-002 | B |
| I-005 | B |
| I-007 | B |
| I-008 | A |
| I-009 | C |
| I-010 | C |
| I-011 | C |
| I-013 | B |
| I-014 | B |
| I-016 | A |
| I-017 | A |
| I-018 | B |
| I-019 | C |
| I-020 | B |
| I-021 | A |
| I-022 | B |
| I-023 | B |
| I-024 | A |
| I-025 | B |
| I-026 | C |
| I-027 | C |
| I-028 | A |
| I-032 | C |
| I-034 | B |
| I-035 | B |
| I-036 | C |
| I-038 | B |
| I-039 | B |
| I-040 | B |
| I-041 | B |
| I-042 | B |
| I-044 | A |
| I-045 | A |
| I-047 | B |
| I-048 | A |
| I-049 | A |
| I-050 | A |
| I-051 | C |

TABLE 38

| Compound No. | h-5-HT2C Ki |
|---|---|
| I-058 | B |
| I-059 | C |
| I-060 | B |
| I-061 | B |
| I-063 | B |
| I-064 | A |
| I-065 | A |
| I-066 | C |
| I-067 | A |
| I-068 | C |
| I-069 | B |
| I-070 | B |
| I-075 | B |
| I-076 | B |
| I-077 | A |
| I-078 | A |
| I-079 | A |
| I-080 | A |
| I-081 | A |
| I-082 | B |
| I-085 | B |
| I-087 | A |
| I-088 | A |
| I-089 | A |
| I-090 | A |
| I-091 | A |
| I-092 | A |
| I-093 | B |
| I-094 | B |
| I-095 | B |
| I-096 | A |
| I-097 | A |
| I-098 | A |
| I-099 | A |
| I-100 | A |
| I-105 | A |
| I-106 | A |
| I-108 | A |
| I-111 | A |
| I-112 | A |
| I-113 | A |
| I-114 | A |
| I-115 | A |
| I-116 | A |
| I-119 | A |
| I-120 | A |
| I-121 | A |
| I-124 | A |
| I-125 | B |
| I-127 | C |

Test Example 3: hERG Test

For the purpose of evaluating risk of an electrocardiogram QT interval prolongation of the compound according to the present invention, effects of the compound according to the present invention on delayed rectifier $K^+$ current ($I_{Kr}$), which plays an important role in the ventricular repolarization process, are studied using CHO cells expressing human ether-a-go-go related gene (hERG) channel.

After a cell was retained at a membrane potential of −80 mV by whole cell patch clamp method using an automated patch clamp system (QPatch; Sophion Bioscience A/S) and gave a leak potential of −50 mV, $I_{Kr}$ induced by depolarization pulse stimulation at +20 mV for 2 seconds, and further, repolarization pulse stimulation at −50 mV for 2 seconds, is recorded. A vehicle, which is the 0.1% dimethyl sulfoxide solution in extracellular solution (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethane-sulfonic acid): 10 mmol/L, pH=7.4), or the compound according to the present invention is dissolved at an objective concentration in the extracellular solution, and each of the extracellular solution is applied to the cell at room temperature for 15 minutes or more. From the obtained $I_{Kr}$, an absolute value of the tail peak current is measured based on the current value at the resting membrane potential using analysis software (QPatch Assay software; Sophion Bioscience A/S). The inhibition rate of the tail peak current after application of the compound according to the present invention relative to the tail peak current after application of the vehicle is calculated, and further correction is performed using the inhibition rate result of the negative control to evaluate influence of the compound according to the present invention on $I_{Kr}$. The dilution concentration is changed as necessary.

Test Example 3-2: hERG Test

For the purpose of evaluating risk of an electrocardiogram QT interval prolongation of the compound of the present invention, effects of the compound were studied by evaluating the activity of potassium channel using CHO cells expressing human ether-a-go-go related gene (hERG) channel.

Evaluation was performed using a FluxORII Green Potassium IonCgannel Assay kit (Invitrogen: Molecular Probes).

Cells were seeded in a 384-assay plate (8000 cells/well/40 μL) and incubated (37° C., 5% $CO_2$) overnight. After replacing the medium with a Wash buffer (1×HBSS, 20 mM HEPES) with a microplate washer, a fluorescent indicator was added to the medium and allowed to incubate (37° C., 5% $CO_2$) for 1 hour for incorporation of the fluorescent indicator into cells.

A cell plate was placed on a cell-based kinetic assay system FLIPR (Molecular Devices, LLC.), and the compound was added to the cells so as to have a desired concentration and reacted for 10 minutes. When a mixed solution of potassium and thallium as a stimulator was added thereto, the potassium channel was opened, and thallium that flowed into the cells bound to the fluorescent indicator, so that the intracellular fluorescence signal increased, and the potassium channel current was detected as a fluorescence signal. For the inhibition rate at each concentration, the signal intensity when E-4031 was added to cells at a final concentration of 10.3 μmol/L was defined as an inhibition rate of 100%, and the signal intensity when DMSO was added to cells at a final concentration of 0.7% was defined as an inhibition rate of 0%. Then, the inhibition rate was calculated from the signal intensity at each concentration. $IC_{50}$ was calculated from the inhibition rate at each concentration.

(Results)

Compound I-081: $IC_{50}$>52.0 μM
Compound I-082: $IC_{50}$>52.0 μM
Compound I-083: $IC_{50}$>52.0 μM
Compound I-084: $IC_{50}$>52.0 μM
Compound I-099: $IC_{50}$=46.8 μM Test Example 4: BA Test Materials and methods for experiments to evaluate oral absorption (1) Experimental animals: Mice or rats are used.
(2) Rearing condition: Mice or rats are allowed free access to solid feed and sterilized tap water.
(3) Setting of dosage and grouping: Oral administration and intravenous administration are performed with the predetermined dosage. Grouping is set as below. The dosage is changed per compound as necessary.

Oral administration 2 to 60 μmol/kg or 1 to 30 mg/kg (n=2 to 3)

Intravenous administration 1 to 30 μmol/kg or 0.5 to 10 mg/kg (n=2 to 3)

(4) Preparation of administration solutions: Oral administration is performed as solution or suspension. Intravenous administration is performed after solubilization.
(5) Routes of administration: Oral administration is performed mandatory into the stomach by oral sonde. Intravenous administration is performed from caudal vein by syringes with needle.
(6) Evaluation items: Blood is collected serially and concentration of a compound according to the present invention in plasma is measured by LC/MS/MS.
(7) Statistical analysis: About transition of concentration of a compound according to the present invention in plasma, the area under the plasma concentration versus time curve (AUC) is calculated by moment analysis method, and bioavailability (BA) of a compound according to the present invention is calculated from the dosage ratio and the AUC ratio between the oral administration group and the intravenous administration group.

The dilution concentration or the dilution solvent are changed as necessary.

Test Example 5: Clearance Evaluation Test

Materials and Methods for Experiments (1) Experimental animals: SD rats are used.
(2) Rearing condition: SD rats are allowed free access to solid feed and sterilized tap water.
(3) Setting of dosage and grouping: Intravenous administration was performed with the predetermined dosage. Grouping is set as below.

Intravenous administration 1 μmol/kg (n=2)

(4) Preparation of administration solutions: Administration is performed after solubilization by using dimethyl sulfoxide/propylene glycol=1/1 as the solvent.
(5) Routes of administration: Intravenous administration is performed from caudal vein by syringes with needle.
(6) Evaluation items: Blood is collected serially and concentration of a compound according to the present invention in plasma is measured by LC/MS/MS.
(7) Statistical analysis: About transition of concentration of a compound according to the present invention in plasma, total clearance (CLtot) of a compound according to the present invention is calculated by the moment analysis method. The dilution concentration or the dilution solvent are changed as necessary.

Test Example 6: Metabolic Stability Test

Using commercially available pooled human hepatic microsomes, a compound according to the present invention is reacted for a constant time, and a remaining rate is calculated by comparing a reacted sample and an unreacted sample, thereby, a degree of metabolism of the compound according to the present invention in liver is evaluated.

A reaction is performed (oxidative reaction) at 37° C. for 0 minutes or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human hepatic microsomes. After the reaction, 50 μL of the reaction solution is added to 100 μL of a solution of methanol/acetonitrile=1/1 (v/v), mixed and centrifuged at 3000 rpm for 15 minutes. The compound according to the present invention in the supernatant is quantified by LC/MS/MS or Solid Phase Extraction (SPE)/MS, and a remaining amount of the compound according to the present invention after the reaction is calculated, letting a compound amount at 0 minute reaction time be 100%. Hydrolysis reaction is performed in the absence of NADPH, and glucuronidation reaction is performed in the presence of 5 mmol/L UDP-glucuronic acid instead of NADPH. Then, the same operation is carried out. The dilution concentration or the dilution solvent are changed as necessary.

Test Example 6-2: Metabolic Stability Test

Using commercially available pooled human hepatic microsomes, a compound according to the present invention was reacted for a constant time, and a remaining rate was calculated by comparing a reacted sample and an unreacted sample, thereby, a degree of metabolism of the compound according to the present invention in liver was evaluated.

A reaction was performed (oxidative reaction) at 37° C. for 0 minutes or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human hepatic microsomes. After the reaction, 70 μL of the reaction solution was added to 140 μL of a solution of methanol/acetonitrile=1/1 (v/v), mixed and centrifuged at 3000 rpm for 15 minutes. The compound according to the present invention in the supernatant was quantified by LC/MS/MS or Solid Phase Extraction (SPE)/MS, and a remaining rate of the compound according to the present invention after the reaction was calculated, letting a compound amount at 0 minute reaction time be 100%.

(Results) The remaining rate of the compound at a concentration of 0.5 μmol/L is shown.

Compound I-016: 99.6%
Compound I-028: 90.2%
Compound I-043: 85.0%
Compound I-077: 85.3%
Compound I-086: 75.5%
Compound I-088: 80.0%
Compound I-102: 97.3%

Test Example 7: P-gp Substrate Test

The compound according to the present invention is added to one side of a Transwell (registered trademark, CORNING) in which human MDR1-expressing cells or parent cells are cultured in a single layer, and reacted for a certain period of time. For MDR1-expressing cells and parent cells, the membrane permeability coefficients from the Apical side to the Basolateral side (A→B) and from the Basolateral side to the Apical side (B→A) are calculated, and Efflux Ratio (ER; ratio of membrane permeability coefficients of B→A and A→B) value of the MDR1-expressing cells and the parent cells are calculated. The Efflux Ratio (ER value) of the MDR1-expressing cells and the parent cells are compared to determine whether the compound according to the present invention is a P-gp substrate or not.

Test Example 8: MK801-Induced Hyperactivity Inhibition Test 6 to 10-week-old Wistar male rats were used. For preparation of a test compound administration solution, 30 mmol/L HCl was used as a vehicle by dissolving the test compound, and for preparation of an MK801 administration solution, saline was used as a vehicle by dissolving MK801. Using SCANET manufactured by Melquest Ltd., a data collection program SCL-40, and a transparent plastic cage, the MK801-induced hyperactivity inhibition test was performed as follows.

In the rearing room, the compound administration solution (vehicle or test compound solution) was subcutaneously administered to animals, and the animals were returned to the rearing cage. After 30 minutes, the animals were brought into a laboratory and subjected to laboratory acclimation. 15 minutes after that, the rats were gently taken out, and the MK801 administration solution (vehicle or MK801 solution) was intraperitoneally administered to the rats and the rats were returned to the rearing cage. The rats were taken out 15 minutes after intraperitoneal administration, and placed gently into the SCANET, and measurement of the amount of motor activity was started. The measurement was ended 30 minutes after the start of the measurement, and the amounts of motor activity of the individuals for 30 minutes were summed.

Analysis of the test results was performed as follows.

One-way ANOVA (significance level: two-sided 5%) was performed in the test compound administration group and the vehicle administration group. When significant suppression of the amount of motor activity was shown in the test compound administration group as compared with the vehicle administration group, it was determined that the test compound had an antipsychotic effect.

Figure 2:
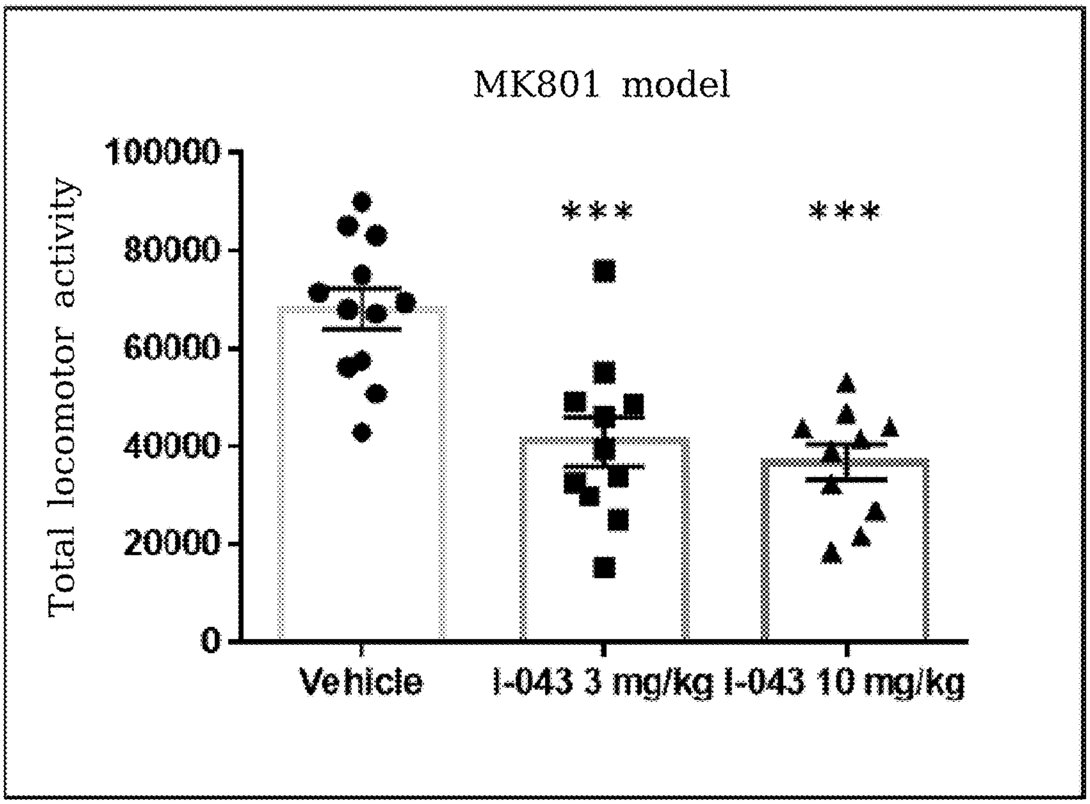
FIG. 2 shows the results of a test for inhibitory effect on rat MK801-induced hyperactivity when a vehicle and Example Compound I-043 were administered.

The results of the above test are shown in FIGS. 1 and 2. In the figures, ● indicates the total locomotor activity of rats upon vehicle administration, ■ indicates the total locomotor activity of rats upon administration of the Example compound of the present application (3 mg/kg), and ▲ indicates the total locomotor activity of rats upon administration of the Example compound of the present application (10 mg/kg).

The following formulation examples are merely examples, and are not intended to limit the scope of the invention.

The compound according to the present invention can be administered as a pharmaceutical composition by any conventional route, in particular enterally, for example, orally, for example, in the form of tablets or capsules, or parenterally, for example, in the form of injectable solutions or suspensions, topically, for example, in the form of lotions, gels, ointments, or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating, or coating methods. For example, oral compositions can be tablets, granules, or capsules containing excipients, disintegrants, binders, lubricants, and the like, and active ingredients. Compositions for injection can be solutions or suspension, may be sterilized, and may contain preservatives, stabilizers, buffering agents, and the like.

INDUSTRIAL APPLICABILITY

The compound according to the present invention has serotonin 5-HT2A receptor antagonism and/or inverse agonism, and the compound is considered to be useful as a therapeutic and/or prophylactic agent for a disease or condition related to a serotonin 5-HT2A receptor.

The invention claimed is:

1. A compound represented by Formula (I):

(I)

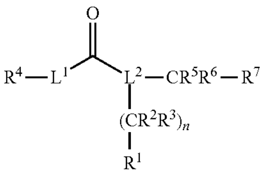

wherein $R^1$ is substituted or unsubstituted 5-membered aromatic heterocyclyl or substituted or unsubstituted 6-membered aromatic heterocyclyl;

$R^2$ is each independently a hydrogen atom, halogen, hydroxy, substituted or unsubstituted alkyl, or substituted or unsubstituted alkyloxy;

$R^3$ is each independently a hydrogen atom, halogen, hydroxy, substituted or unsubstituted alkyl, or substituted or unsubstituted alkyloxy;

n is 1 or 2;

a combination of ($L^1$, $L^2$) is (NH, N) or ($CH_2$, N);

$R^4$ is a group represented by Formula:

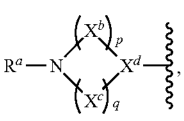
,
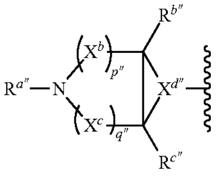
or
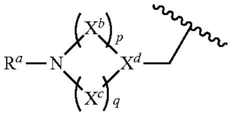

wherein p and q are each 2;

p" and q" are each independently 1 or 2;

$R^a$ is a hydrogen atom, substituted or unsubstituted alkyl, substituted or unsubstituted alkenyl, substituted or unsubstituted alkynyl, substituted or unsubstituted non-aromatic carbocyclyl, or substituted or unsubstituted non-aromatic heterocyclyl;

$R^{a''}$ is a hydrogen atom, substituted or unsubstituted alkyl, substituted or unsubstituted alkenyl, substituted or unsubstituted alkynyl, substituted or unsubstituted non-aromatic carbocyclyl, or substituted or unsubstituted non-aromatic heterocyclyl;

$X^b$ is each independently $CR^bR^{b'}$;

$X^c$ is each independently $CR^cR^{c'}$;

$R^b$ is each independently a hydrogen atom, halogen, substituted or unsubstituted alkyl, or substituted or unsubstituted alkyloxy;

$R^{b'}$ is each independently a hydrogen atom, halogen, substituted or unsubstituted alkyl, or substituted or unsubstituted alkyloxy;

$R^c$ is each independently a hydrogen atom, halogen, substituted or unsubstituted alkyl, or substituted or unsubstituted alkyloxy;

$R^{c'}$ is each independently a hydrogen atom, halogen, substituted or unsubstituted alkyl, or substituted or unsubstituted alkyloxy;

$R^{b''}$ is a hydrogen atom, halogen, substituted or unsubstituted alkyl, or substituted or unsubstituted alkyloxy;

$R^{c''}$ is a hydrogen atom, halogen, substituted or unsubstituted alkyl, or substituted or unsubstituted alkyloxy;

$X^d$ is $CR^d$ or N;

$X^{d''}$ is $CR^d$ or N;

$R^d$ is a hydrogen atom, halogen, cyano, substituted or unsubstituted alkyl, or substituted or unsubstituted carbamoyl;

$R^b$ and $R^{b'}$ and $R^c$ and $R^{c'}$ may be taken together with the same carbon atom to which they are bonded to form a substituted or unsubstituted non-aromatic carbocycle or a substituted or unsubstituted non-aromatic heterocycle;

$R^a$, and $R^b$ bonded to a carbon atom adjacent to a nitrogen atom to which $R^a$ is bonded may be taken together with the nitrogen atom to which $R^a$ is bonded and the carbon atom to which $R^b$ is bonded to form a substituted or unsubstituted non-aromatic heterocycle; or $R^a$, and $R^c$ bonded to a carbon atom adjacent to a nitrogen atom to which $R^a$ is bonded may be taken together with the nitrogen atom to which $R^a$ is bonded and the carbon atom to which $R^c$ is bonded to form a substituted or unsubstituted non-aromatic heterocycle;

$R^b$ and $R^o$ may be taken together to form a (C1-C3) bridge, wherein one of the carbon atoms constituting the bridge may be replaced with an oxygen atom;

$R^a$ and $R^d$ may be taken together to form a (C1-C3) bridge, wherein one of the carbon atoms constituting the bridge may be replaced with an oxygen atom;

$R^5$ and $R^6$ are each independently a hydrogen atom, halogen, hydroxy, substituted or unsubstituted alkyl, or substituted or unsubstituted alkyloxy; or $R^5$ and $R^6$ may be taken together with the same carbon atom to which they are bonded to form a substituted or unsubstituted non-aromatic carbocycle;

$R^7$ is a group represented by Formula:

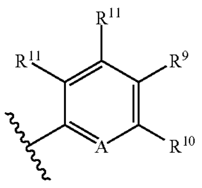

wherein A is $CR^{11}$ or N;

$R^9$ is substituted or unsubstituted alkyloxy, substituted or unsubstituted amino, substituted or unsubstituted aromatic carbocyclyloxy, substituted or unsubstituted alkyl, substituted or unsubstituted non-aromatic carbocyclyl, or cyano;

$R^{10}$ is a hydrogen atom, halogen, hydroxy, substituted or unsubstituted alkyl, or substituted or unsubstituted alkyloxy; or $R^9$ and $R^{10}$ may be taken together to form a substituted or unsubstituted non-aromatic carbocycle or a substituted or unsubstituted non-aromatic heterocycle;

$R^{11}$ is each independently a hydrogen atom, halogen, hydroxy, substituted or unsubstituted alkyl, or substituted or unsubstituted alkyloxy;

provided that the following compounds are excluded:

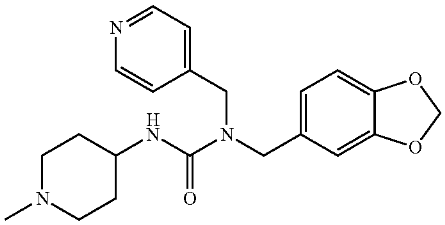

,

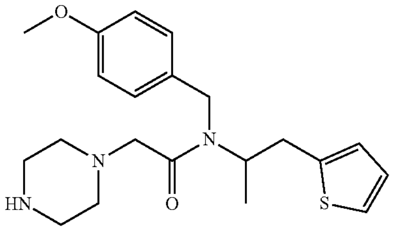

and

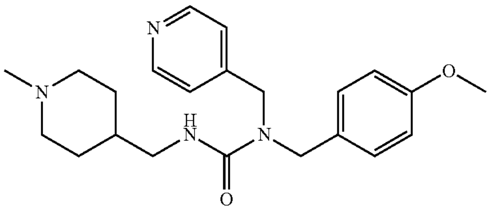

, or a pharmaceutically acceptable salt thereof.

2. The compound according to claim 1, wherein A is $CR^{11}$, or a pharmaceutically acceptable salt thereof.

3. The compound according to claim 1, wherein A is CH, or a pharmaceutically acceptable salt thereof.

4. The compound according to claim 1, wherein $X^d$ is $CR^4$, and $R^d$ is a hydrogen atom or substituted or unsubstituted alkyl, or a pharmaceutically acceptable salt thereof.

5. The compound according to claim 1, wherein $X^d$ is CH, or a pharmaceutically acceptable salt thereof.

6. The compound according to claim 1, wherein $R^2$ is each independently a hydrogen atom or substituted or unsubstituted alkyl, and $R^3$ is each independently a hydrogen atom or substituted or unsubstituted alkyl, or a pharmaceutically acceptable salt thereof.

7. The compound according to claim 1, wherein $R^5$ and $R^6$ are each independently a hydrogen atom or substituted or unsubstituted alkyl, or a pharmaceutically acceptable salt thereof.

8. The compound according to claim 1, wherein $R^1$ is substituted or unsubstituted 5-membered aromatic heterocyclyl, substituted or unsubstituted pyridin-2-yl, substituted or unsubstituted pyridin-3-yl, substituted or unsubstituted pyridazin-3-yl, substituted or unsubstituted pyrimidin-4-yl, or substituted or unsubstituted pyrazinyl, or a pharmaceutically acceptable salt thereof.

9. The compound according to claim 1, wherein $R^1$ is substituted or unsubstituted 5-membered aromatic heterocyclyl, or a pharmaceutically acceptable salt thereof.

10. The compound according to claim 1, wherein the compound is selected from the group consisting of

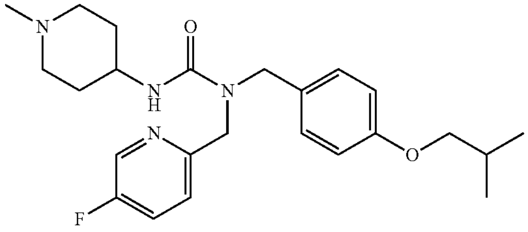

,

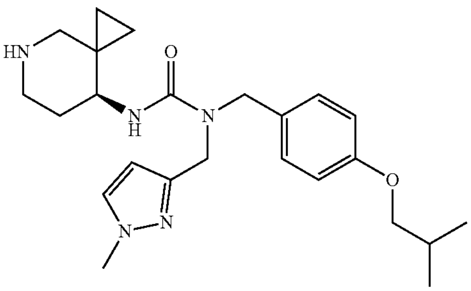

,

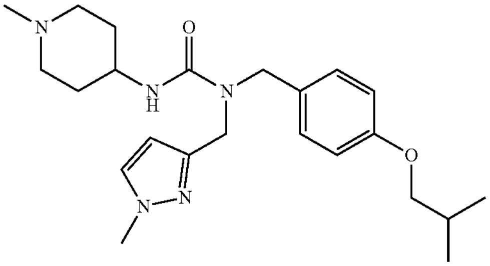

,

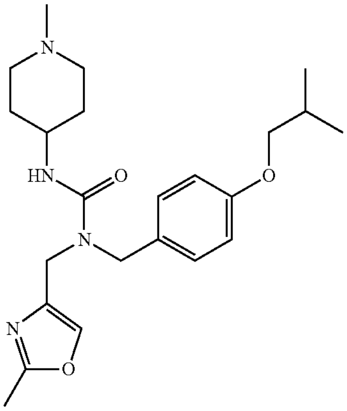

,

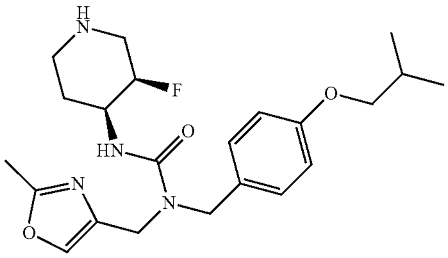

,

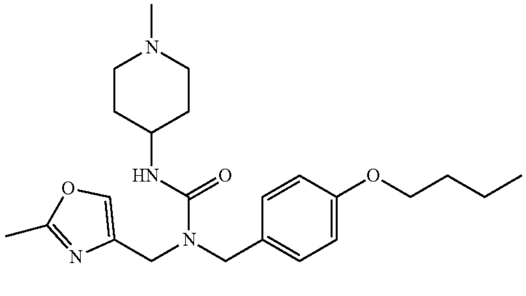

,

-continued
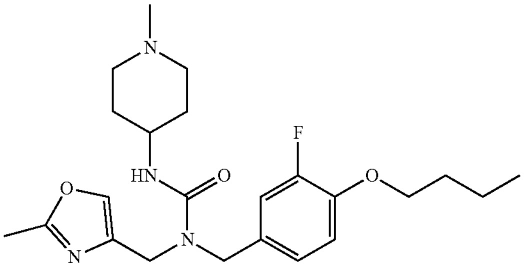
,
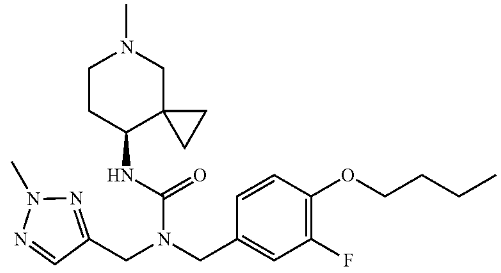
,
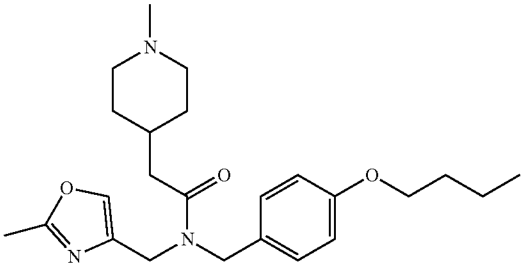
,
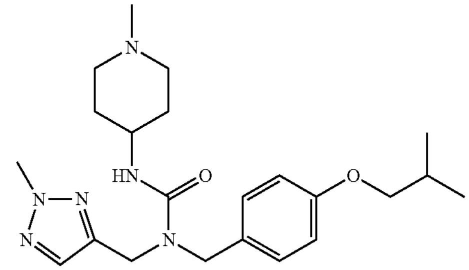
,
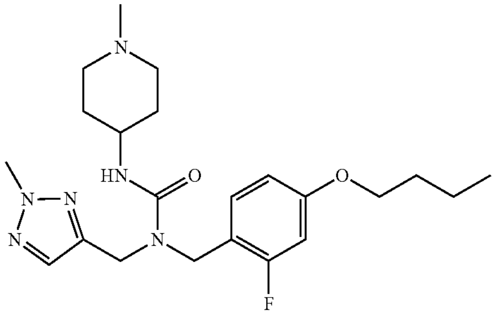
,
-continued
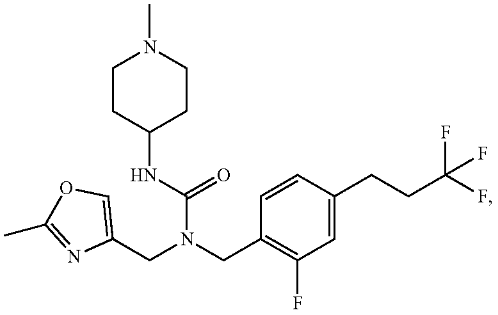
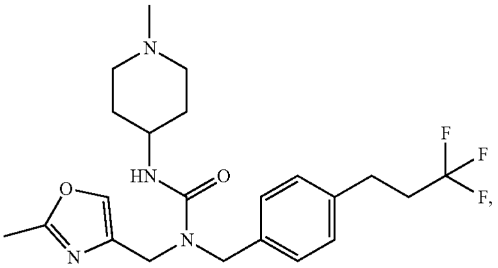
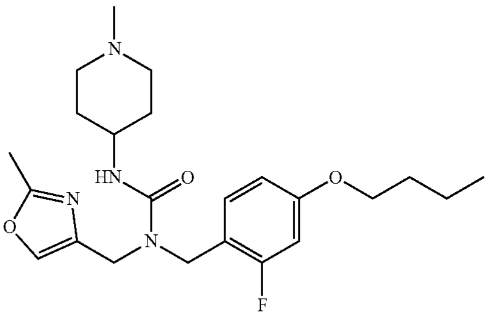
,
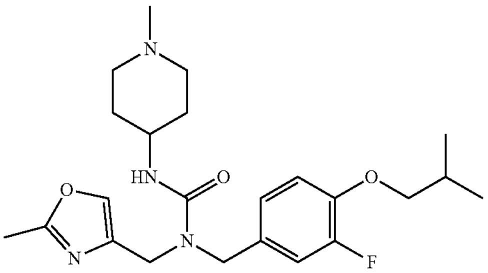
,
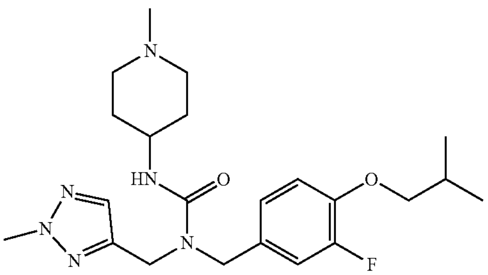
, -continued

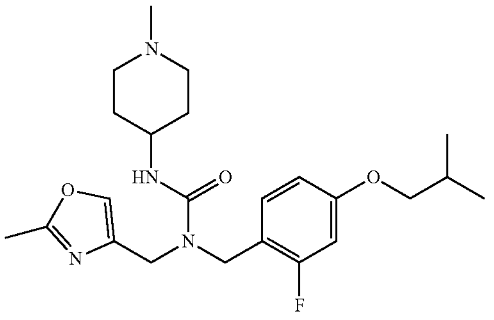

,

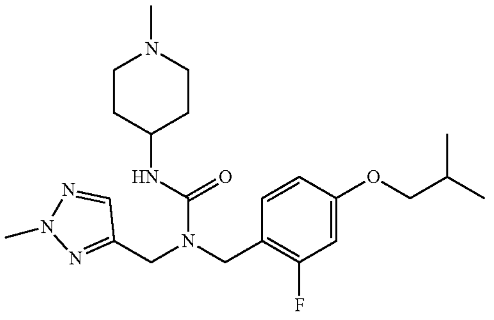

,

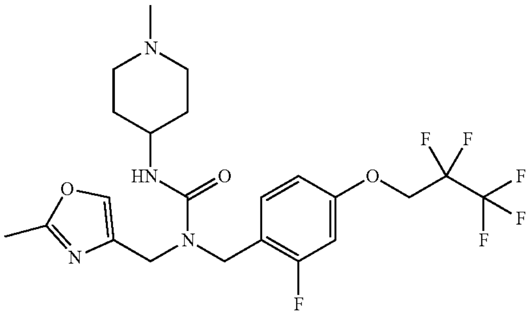

and

-continued

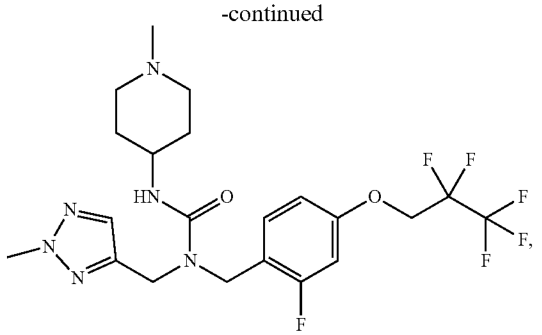

or a pharmaceutically acceptable salt thereof.

11. A pharmaceutical composition comprising the compound according to claim 1 or a pharmaceutically acceptable salt thereof, and a pharmaceutically acceptable carrier or diluent.

12. The pharmaceutical composition according to claim 11, wherein the pharmaceutical composition is a serotonin 5-HT2A receptor antagonist and/or inverse agonist.

13. The pharmaceutical composition according to claim 11, wherein the pharmaceutical composition is a serotonin 5-HT2A receptor antagonist and/or inverse agonist and a 5-HT2C receptor antagonist and/or inverse agonist.

14. A method for treating and/or preventing a disease related to a serotonin 5-HT2A receptor comprising administering an effective amount of the compound according to claim 1, or a pharmaceutically acceptable salt thereof, to a subject in need thereof.

15. A method for treating and/or preventing a disease related to serotonin 5-HT2A and 5-HT2C receptors comprising administering an effective amount of the compound according to claim 1, or a pharmaceutically acceptable salt thereof, to a subject in need thereof.

16. A pharmaceutical composition comprising the compound according to claim 10 or a pharmaceutically acceptable salt thereof, and a pharmaceutically acceptable carrier or diluent.

17. A method for treating and/or preventing a disease related to a serotonin 5-HT2A receptor comprising administering an effective amount of the compound according to claim 10, or a pharmaceutically acceptable salt thereof, to a subject in need thereof.

18. The compound according to claim 1, wherein $R^1$ is substituted or unsubstituted pyrazolyl, substituted or unsubstituted pyrrolyl, substituted or unsubstituted furyl, substituted or unsubstituted thienyl, substituted or unsubstituted oxazolyl, substituted or unsubstituted triazolyl, substituted or unsubstituted isoxazolyl, or substituted or unsubstituted thiazolyl, or a pharmaceutically acceptable salt thereof.

* * * * *